(12) United States Patent
Mazor et al.

(10) Patent No.: US 10,208,108 B2
(45) Date of Patent: *Feb. 19, 2019

(54) ANTIBODIES DIRECTED TO RICIN TOXIN

(71) Applicant: THE ISRAEL INSTITUTE OF BIOLOGICAL RESEARCH (IIBR), Ness-Ziona (IL)

(72) Inventors: Ohad Mazor, Ness-Ziona (IL); Ronit Rosenfeld, Ness Ziona (IL); Arie Ordentlich, Ness-Ziona (IL); Tal Noy-Porat, Ness-Ziona (IL)

(73) Assignee: THE ISRAEL INSTITUTE OF BIOLOGICAL RESEARCH (IIBR), Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,424

(22) Filed: Jan. 4, 2017

(65) Prior Publication Data
US 2017/0174752 A1   Jun. 22, 2017

Related U.S. Application Data

(63) Continuation-in-part of application No. 14/952,283, filed on Nov. 25, 2015.

(60) Provisional application No. 62/085,417, filed on Nov. 28, 2014.

(51) Int. Cl.
| | |
|---|---|
| G01N 33/68 | (2006.01) |
| A61K 39/00 | (2006.01) |
| A61K 45/06 | (2006.01) |
| C07K 16/16 | (2006.01) |
| C07K 16/40 | (2006.01) |
| G01N 33/53 | (2006.01) |

(52) U.S. Cl.
CPC .............. *C07K 16/16* (2013.01); *A61K 45/06* (2013.01); *C07K 16/40* (2013.01); *G01N 33/5308* (2013.01); *G01N 33/6854* (2013.01); *A61K 2039/505* (2013.01); *A61K 2039/507* (2013.01); *A61K 2039/545* (2013.01); *C07K 2317/24* (2013.01); *C07K 2317/76* (2013.01); *G01N 2333/924* (2013.01)

(58) Field of Classification Search
None
See application file for complete search history.

(56) References Cited

U.S. PATENT DOCUMENTS

| | | | |
|---|---|---|---|
| 5,626,844 | A | 5/1997 | Lemley et al. |
| 6,407,213 | B1 | 6/2002 | Carter et al. |
| 6,639,055 | B1 | 10/2003 | Carter et al. |
| 6,780,413 | B2 | 8/2004 | Hott et al. |
| 7,175,845 | B2 | 2/2007 | Dertzbaugh |
| 8,247,186 | B2 | 8/2012 | Grompe et al. |
| 8,344,109 | B2 | 1/2013 | Thullier et al. |
| 8,535,668 | B2 * | 9/2013 | Thullier ............ C07K 16/16 424/133.1 |
| 9,309,305 | B2 | 4/2016 | Hu et al. |
| 2002/0081303 | A1 | 6/2002 | Hott et al. |
| 2005/0266010 | A1 | 12/2005 | Hott et al. |
| 2007/0009510 | A1 | 1/2007 | Dertzbaugh |
| 2010/0240597 | A1 | 9/2010 | Cramer et al. |
| 2012/0121512 | A1 | 5/2012 | Grompe et al. |
| 2012/0258100 | A1 | 10/2012 | Thullier et al. |
| 2014/0050722 | A1 | 2/2014 | Thullier et al. |
| 2014/0093504 | A1 | 4/2014 | Hu et al. |
| 2016/0152732 | A1* | 6/2016 | Mazor .................. C07K 16/40 424/146.1 |
| 2016/0207998 | A1 | 7/2016 | Hu et al. |
| 2016/0280773 | A1 | 9/2016 | Hu et al. |
| 2017/0174752 | A1* | 6/2017 | Mazor .................. C07K 16/16 |

FOREIGN PATENT DOCUMENTS

| | | | | |
|---|---|---|---|---|
| FR | 2922212 A1 * | 4/2009 | ............ | C07K 16/16 |
| FR | 2952059 A1 * | 5/2011 | ............ | C07K 16/16 |
| WO | 03/072018 A2 | 9/2003 | | |
| WO | 2012167346 A1 | 12/2012 | | |
| WO | 2016/069627 A1 | 5/2016 | | |

OTHER PUBLICATIONS

Cohen et al., Characterization and epitope mapping of the polyclonal antibody repertoire elicited by ricin holotoxin-based vaccination, Clinical and Vaccine Immunology p. 1534-1540, vol. 21 No. 11 (2014).

Gal et al, Antibody/doxycycline combined therapy for pulmonary rincinosis: Attenuation of inflammation improves survival of ricin-intoxicated mice, Toxicology Reports, 1:496-504 (2014).

Gal et al, Rapid assessment of antibody-induced ricin neutralization by employing a novel functional cell-based assay, Journal of Immunological Methods 424:136-139 (2015).

Maddaloni et al, Immunological characteristics associated with the protective efficacy of antibody to ricin, J Immunol 2004:172:6221-6228 (2017).

(Continued)

*Primary Examiner* — Nita M. Minnifield
(74) *Attorney, Agent, or Firm* — Browdy and Neimark, PLLC

(57) ABSTRACT

The invention provides a pharmaceutical composition comprising as an active ingredient a combination of three isolated monoclonal antibodies or any antigen-binding fragment thereof which bind ricin toxin and neutralize its toxic effects, and a pharmaceutically acceptable carrier, excipient or diluent. The invention also provides a method of prophylaxis, treatment or amelioration of ricin toxin poisoning including administering to a subject in need thereof a therapeutically effective amount of the pharmaceutical composition.

16 Claims, 12 Drawing Sheets
Specification includes a Sequence Listing.

(56) References Cited

OTHER PUBLICATIONS

McGuiness et al, Characterization of a novel high-affinity monoclonal immunoglobulin G antibody against the ricin B subunit, Infection and Immunity, 74/6:3463-3470 (Jun. 2006).

Noy-Porat et al, Isolation of anti-ricin protective antibodies exhibiting high affinity from immunized non-human primates, Toxins, 8, 64, 15 pages (2016).

Sabo et al, Antibody treatment against pulmonary exposure to abrin confers significantly higher levels of protection than treatment against ricin intoxication, Toxicology Letters 237:72-78 (2015).

Yermakova et al, Protective immunity to ricin toxin conferred by antibodies against the toxin's binding subunit (RTB), Vaccine, 29:7925-7935 (2011).

Sabo et al, "Ricin-Holotoxin-Based Vaccines: Induction of Potent Ricin-Neutralizing Antibodies", Methods in Molecular Biology, 1403(38):683-694 (2016).

Noy-Porat et al, Extended therapeutic window for post-exposure treatment of ricin intoxication conferred by the use of high-affinity antibodies, Toxicon 127:100-105 (2017).

Sandvig, K. and van Deurs, B. (1996) Physiol Rev 76:949-966.

Hu, W. G., et al. "Humanization and Characterization of an Anti-Ricin Neutralization Monoclonal Antibody" Plos One 7 (9): e45595 1-9 (2012).

Luker, G. D., et al. "Imaging 26S proteasome activity and inhibition in living mice" Nature Med 9:969-973 (2003).

* cited by examiner

Fig. 1

```
              1                                                          60
MH74 VH       GAGGTGCAGCTGGTGCAATCTGGAGCAGAGGTGAAAAGGCCCGGGGAGTCACTGAAGATC
MH73 VH       CAGGTGCAGCTGCAGGAGTCGGGCCCAGGACTGGTGAAGCCTTCGGAGACCCTGTCCCTC
MH77 VH       CAGGTGCAGCTGCTCGAGTCGGGCCCAGGACTGGTGAAGCCTTCAGAGACCCTGTCCCTC
MH1  VH       CAGCTGCAGCTGCAGGAGTCGGGCCCAGGACTGGTGAAGCCTTCAGAGACCCTGTCCCTC
MH49 VH       GAGGCGCAGCTCGAGGAGTCGGGCCCAGGACTGGTGAAGCCTTCGGAGACCCTGTCCCTC
MH67 VH       CAGGTGCAGCTCGAGCAGTCGGGCCCAGGACTGGTGAAGCCTTCGGAGACCCTGTCCCTC
MH36 VH       GAAGTGCAGCTGGTGGAGTCTGGGGGAGGCTTGGTCCAGCCTGGGGGGTCCCTGAGGCTC
MH76 VH       CAGGTGCAGCTGCAGGAGTCTGGGGGCGGCTTGGCAAAGCCTGGGGGGTCCCTGAGACTC
MH2  VH       GAGGTTCAGTTGGTGGAATCTGGGGGCGGCTTGGCAAAGCCTGGGGGGTCCCTGAGACTC
MH75 VH       CAGGAGCAGCTGGTGCAGTCTGGGGGCGGCTTGGCAAAGCCTGGGGGGTCCCTGAGACTC
              61                                                         120
MH74 VH       TCCTGTAAGACTTCTGGATACAGCTTTA...CCAGCTACTGGATCAGCTGGGTGCGCCAG
MH73 VH       ACCTGCGCTGTCTCTGGTGGCTCCCTCA...GCAGTAACTACTGGAGCTGGATCCGCCAG
MH77 VH       ACCTGCACTGTCTCTGGTGGCTCTTTCAGTAGTAGTCATTGGTGGAACTGGATCCGCCAG
MH1  VH       ACTTGCGCTGTCTCTGGTGGCTCCATCAGCGGTGGTTATGGCTGGGGCTGGATCCGCCAG
MH49 VH       AGTTGCGCTGTCTCTGGTGGCTCCTTCA...GGAGTTACTGGTGGGGCTGGATCCGCCAG
MH67 VH       AGTTGCGCTGTCTCTGGTGGCTCCTTCA...GGAGTTACTGGTGGGGCTGGATCCGCCAG
MH36 VH       TCCTGTGCAGCCTCTGGATTCACCTTCA...GTAACGTCTGGATGAACTGGGTCCGCCAG
MH76 VH       TCCTGCGCAGCCTCCGGATTCACCTTCA...GTGACTACTACATGGACTGGGTCCGCCAG
MH2  VH       TCCTGCGCAGCCTCCGGATTCACCTTCA...GTGACTACTACATGGACTGGGTCCGCCAG
MH75 VH       TCCTGCGCAGACTCCGGATTCACCTTCA...GTGACCACTACATGGACTGGGTCCGCCAG
              121                                                        180
MH74 VH       ATGCCCGGGAAAGGCCTGGAGTGGATGGGGGCGA......TTGATCCTACTGATTCTGAT
MH73 VH       GCCCCAGGGAAGGGACTGGAGTGGATTGGACATA......TCTTTGGTGGTGGTGGGGGC
MH77 VH       GCCCCAGGGAAAGGGCTGGAGTGGATTGGCTATA......TCACCACTAGTAATGGTGCC
MH1  VH       CCCCCAGGGAAGGGGCTGGAGTGGGTTGGGAGTA......TCTATGGTAGTACTGGGAAC
MH49 VH       CCCCCAGGGAAGGGGCCTGGAGTGGATTGGGAGTA......TCTATGGCAGTAGTGGGAGC
MH67 VH       CCCCCAGGGAAGGGCCTGGAGTGGATTGGGAGTA......TCTATGGCAGTAGTGGGAGC
MH36 VH       ACTCCAGGGAAGGGGCTAGAGTGGGTTGCCCGTATTAAAGTCAAAGCTGACGGTGGAACA
MH76 VH       GCTCCAGGGAAGGGGCTGGATTGGGTCTCACGCA......TTAGTAATGGTGGTGGTACC
MH2  VH       GCTCCAGGGAAGGGGCTGGAGTGGGTCTCACGTA......TTAGTAATGGTGGTGGTAGT
MH75 VH       GCTCCAGGGAAGGGGCTGGAGTGGGTCTCACGTA......TTAGTACTGGTGGTGGAACC
              181                                                        240
MH74 VH       ACCAGATACAACCCGTCCTTCCAAGGCCAGGTCACCATCTCCGCCGACAAGTCCATCAGC
MH73 VH       ACCGACTACAACCCCTCCCTCAAGAGTCGAGTCACCATTTCAACAGACACGTCCAAGAAC
MH77 VH       ACCTACTACAACCCCTCCCTCAAGAGTCGAGTCACCATTTCAACAGACACGTCCAAGAAC
MH1  VH       ACCTACTACAACCCCTCCCTCAAGAGTCGAGTCACCATTTCAACAGACACGTCCAAGAAC
MH49 VH       ACCGAATACAACCCCTCCCTCAAAAGTCGAGCCACCATTTCAAGAGACACGTCCAAGAAC
MH67 VH       ACCGAATACAACCCCTCCCTCAAAAGTCGAGCCACCATTTCAAGAGACACGTCCAAGAAC
MH36 VH       GCAGATTACGCCGCGTCTGTGAAAGGCAGATTCACCATCTCAAGAGACGATTCAAAGAAC
MH76 VH       ACATGGTACGCAGACTCCGTGAAGGGCAGATTCACCATCTCCAGAGAGAACGCCAAGAAC
MH2  VH       AAATGGTACGCAGACTCCGTGAAGGGCAGATTCACCATCTCCAGAGAGAACGCCAAGAAC
MH75 VH       ACATGGTACGCAGACTCCGTGAAGGGCAGATTCACCATCTCCAGAGAGAACGCCAACAAC
              241                                                        300
MH74 VH       ACCGCCTACCTGCAGTGGAGCAGGCTGAAGGCCTCGGACACCGCCACGTATTACTGTGCG
MH73 VH       CAGTTCTCCCTGAAGCTGAGCTCTGTGGCCGCCGCGGACACGGCCGTGTATTACTGTGCG
MH77 VH       CAGTTCTCCCTGAAACTGAGCTCTGTGACCGCCGCGGACTCGGCCGTGTATTTCTGTGCG
MH1  VH       CAGCTCTCCCTGAAGGTGAGCTCTGTGACCGCCGCGGACACGGCCATCTACTACTGTGCG
MH49 VH       CAGTTCTCCCTGAAGCTGAGCTCTGTGACCGCCGCGGACACGGCCGTCTATTACTGTGCG
MH67 VH       CAGTTCTCCCTGAAGCTGAGCTCTGTGACCGCCGCGGACACGGCCGTCTATTACTGTGCG
MH36 VH       ACACTGTATCTGCAAATGAACAGTCTGAAAACCGAGGACACAGGCCGTGTATTACTGTGCAC.
MH76 VH       ACACTGTATCTTCAAATGAACAGCCTGAGACCTGAGGACACGGCTGTCTATTACTGTGCG
MH2  VH       ACACTGTATCTTCAAATGAACAGCCTGAGAGCTGAGGACACGGCTGTATATTACTGTGCG
MH75 VH       ACACTGTATCTTCAAATGAACAGCCTGAGAGGTGAGGACACGGCTGTCTATTACTGTGCG
              301                                                        360
MH74 VH       AAATCAGACTGGAGTGATTATTATGGCAACTCATTGGATGTCTGGGGCCGGGGAGTTCTG
MH73 VH       AGAGCT.GCAATAATGT.....ACCCCAACCGGTTCGATGTCTGGGGCCCGGGAGTCCTG
```

Fig. 1 (continued)

```
MH77 VH      AGGGGATACAGTAACT......GGGACAACTGGTTCGATGTCTGGGGCCCGGGAGTCCTG
MH1  VH      AGAGCCCGCAGTGGTACTTTG.TGGTT.....CCTCGAGTTCTGGGGCCAGGGCGCCCCG
MH49 VH      AG.....GCAGATACAATTTT.TGACTGATGCTTTTGATTTCTGGGGCCAAGGGCTCAGG
MH67 VH      AG.....GCAGATACAATTTT.TGACTGATGCTTTTGATTTCTGGGGCCAAGGGCTCAGG
MH36 VH      ......CACAGAGGAGATTA..CAGTGGCCCGTTATGACTACTGGGGCCAGGGAGTCCTG
MH76 VH      ACGGTGCCCACAG.........CGACATCTGGAATAGGCAACTGGGGCCAGGGAGTCCTG
MH2  VH      GAAGTTCCCA............CGGGATACAGTCAAGGTGTCTGGGGCCCGGGAGTCCTG
MH75 VH      AAAGTTCCCA............CGGGATACAGTCAAGGGGTCTGGGGGCCGGGAGTCCTG
             361          375
MH74 VH      GTCACAGCCTCTTCA
MH73 VH      GTCACAGCCTCTAGC
MH77 VH      GTCACAGTCTCCTCA
MH1  VH      GTCACAGCATCCTCA
MH49 VH      GTCACAGTCTCCTCA
MH67 VH      GTCACAGCCTCCTCA
MH36 VH      GTCACAGTCTCCTCA
MH76 VH      GTCACAGCCTCCTCA
MH2  VH      TTCACAGTCTCCTCA
MH75 VH      GTCACAGCCTCCTCA
```

Fig. 2

```
               1                                                           60
MH67 VK        GACATTCAGCTGACCCAGTCTCCATCCTCCGTGTCTGCTTCTGTGGGAGACAGAGTCACC
MH73 VK        GAGCTCCTGATGACACAGTCTCCATCCTCCCTGTCTGCATCTGTAGGAGACAGAGTCACC
MH77 VK        GACATTCAGATGTCCCAGTCTCCTTCCTCCCTGTCTGCATCTGTGGGAGACAAAGTCACC
MH2  VL        CAGTCTGTGTTGACTCAG...CCACAATCGGTGTCGGTGTCCCCAGGACAGACGGCCAGG
MH75 VL        CAGTCTGTGTTGACTCAG...CCACAATCGGTGTCGGTGTCCCCAGGACAGACGGCCAGG
MH1  VL        CAGCCTGTGCTGACTCAG...CCACGCTCAGTGTCCGTGTCCCCAGGACAGACGGCCAGG
MH76 VL        CAGCCAGGGCTGACTCAG...CCACACTCGGTGTCGGTGTCCCCAGGACAGACGGCCAGG
MH74 VL        CAGTCTGTGTTGACTCAG...CCGCCCTCAGTGTCTGGGGCGCCAGGACAGAGGGTCACC
MH36 VL        CAGTCTGTGTTGACTCAG...CCACCCTCAGCGTCTGGGGCTCCCGGGCAGAGTGTCACC
MH49 VL        CAGCCAGGGCTGACTCAG...CCTCCCTCAGCGTCTGGGGCTCCCGGGCAGAGTGTCACC 61                                                          120
MH67 VK        ATCACTTGTCGGGCGAGTC......AGGCCAT...CAGTACTTATTTAGCCTGGTATCTA
MH73 VK        ATCTCTTGCCGGGCAAGTC...AGAACATTTA......TAGTAATTTAGCGTGGTATCAG
MH77 VK        ATCACTTGCCAGGCAAGTC......AGAGTGT...TAGCAGCTGGTTAGCCTGGTATCGG
MH2  VL        ATCTCCTGTGGGGGAGACA......ACATTGG...AAGTAAAAATGTGCACTGGTACCAG
MH75 VL        ATCACCTGTGGGGGAGACA......ACATTGG...AAGTAAAAATGTGCACTGGTACCAG
MH1  VL        ATCACCTGTGGGGGAGACA......ACATTGG...AAGTAAAAGTGTGCAGTGGTACCAG
MH76 VL        ATCACCTGTGGGGGAGACA......ACATTGG...AAGTAAAAATGTGCACTGGTACCAG
MH74 VL        ATCTCCTGCACTGGGAGTAATTCCAACATCGGGGCGGGTTATTATGTGCAGTGGTACCAG
MH36 VL        ATCTCTTGCTCTGGAAGCAGCTCCAACATCAG...AGGTAATGGTGTACACTGGTACCAG
MH49 VL        ATCTCTTGCTCTGGAAGCAGCTCTGACATTGG...AAGTCATGACGTCTACTGGTACCAG 121                                                         180
MH67 VK        CAGAGGCCGGGGAAAGCCCCTGAACTCCTGATCTATTATGCAACCACTTTACACACTGGG
MH73 VK        CAGAAACCAGGGAAAACTCCTAAGCTCCTGATCTATGCTGCATCCATCTTGCAGAGTGGG
MH77 VK        CAGAAACCAGGGAAGGCCCCTAAGCCCCTGATCTATAAGGCATCCAGTTTGGAAGGTGGG
MH2  VL        CAGAAGCCACCGCAGGCCCCTGTGCTGGTCATCTATGCTGGAACCGAACGGCCCTCAGGG
MH75 VL        CAGAAGCCACCGCAGGCCCCTGTGCTGGTCATCTATGCTGAAACCGAGCGGCCCTCAGGG
MH1  VL        CAGAAGCCACCGCAGGCCCCTGTGCTGGTCATCTATGCTGATAGCGAACGGCCCTCAGGA
MH76 VL        CAGAAGCCACCGCAGGCCCCTGTGCTGGTCATCTATGCTGATAGCGAACGGCCCTCAGGG
MH74 VL        CAGCTTCCAGGAACGGCCCCCAAACTCCTCATCTATGAAAATAATAAGCGACCCTCAGGG
MH36 VL        CAGCTCTCAGGAATGGCCCCCAAACTCCTCATCTATAATAATAATCAGCGACCCTCAGGG
MH49 VL        CAGCTCCCAGGGACGGCCCCCAAGCTCCTCATCTACTACAGTAATCAGCGACCCTCAGGG 181                                                         240
MH67 VK        GTCGCTTCAGGTCTCACTGGCAGTGGATCTGGGACGGATTTCACTCTCACCCTCAGTGCC
MH73 VK        ATTCCCTCTCGGTTCAGCGGCAGCGGATCTGGGACAGATTACACTCTCACCATCACCAAC
MH77 VK        GTCCCCTCAAGGTTCAGCGGCAGTGGATCTGGGACAGATTTCACTCTCACCATCAACAGC
MH2  VL        ATCCCTGAGCGATTCTCTGGCTCCAACTCCGGGAACACGGCCACCCTGACCATCAGCGGG
MH75 VL        ATCCCTGAGCGATTCTCTGGCTCCAACTCCGGGAACACGGCCACCCTGACCATCAGCGGA
MH1  VL        ATCCCTGAGCGATTCTCTGGCTCCAACTCAGGGAACACCGCCACCCTGACCGTCAGCGGG
MH76 VL        ATCCCTGAGCGATTCTCTGGCTCCAACTCCGGGAACACGGCCACCCTGACCATCAGCGGG
MH74 VL        GTTTCTGATCGATTCTCTGGCTCCAAGTCTGGTACCTCAGCCTCCCTGACCATCACTGGA
MH36 VL        GTCCCTGACCGATTCTCTGGCTCCAAGTCTGGCACGTCAGCCTCCCTGGCCATCACTGGT
MH49 VL        GTCCCTGACCGAATCTCTGGCTCCAAGTCTGGCACGTCAGCCTCCCTGACCATCAGCGGT 241                                                         300
MH67 VK        CTGCAACCTGTAGATGTTGGAACTTACTACTGTCAACAGTTTAAAA.....CTTTACCGT
MH73 VK        CTGCAGCCTGAAGATTTTGGAACTTATTACTGTCAGCAAGGTTTTGGTATCCCCTACACT
MH77 VK        CTGCAGCCTGAAGATTTTGCAACTTATTACTGTCAACAGTATAACAGTGTGCCGTACAGT
MH2  VL        GTCGAGGCCGGGGATGAGGCGGACTATTACTGTCAGGTGTGGGACGGTACCCGTGAGCAT
MH75 VL        GTCGAGGCCGGGGATGAGGCGGACTATTACTGTCAGGTGTGGGACGGTAGCAGTGCACAT
MH1  VL        GTCGAGGCCGGGGATGAGGCTGACTATTACTGTCAGGTGTGGGACAGTAGTAGTGATCAT
```

Fig. 2 (continued)

```
MH76 VL    GTCGAGGCCGGGGATGAGGCTGACTATTACTGTCAGGTGTGGGACAGTAGCAGTAATCAT
MH74 VL    CTTCAGTCTGAGGATGAGGCTGACTATTACTGCCAGTCCTATGACAGCAGCCTGAGTGTT
MH36 VL    CTCCAGTCTGAGGATGAGGCCGATTATTACTGCGAGGCATGGGATAACAGCCTGAGCGGT
MH49 VL    CTCCGGTCCGAGGATGAGGCTGATTATTACTGTGAAACATGGGAAAACAGCCTGAGCGGT 301                              336
MH67 VK    ACACT.TTTGGCCAGGGGACCAAAGTGGACATCAAA
MH73 VK    ......TTTGGCCAGGGGACCAAAGTGGAGTTCAAA
MH77 VK    ......TTTGGCCACGGGACCAAGGTGGACATCAAG
MH2  VL    GTATTATTCGGAGGAGGGACCCGGCTCACCGTCCTA
MH75 VL    GTATTATTCGCAGGAGGGACCCGGCTGACCGTCCTA
MH1  VL    GTGTTATTCGGAGGAGGGACCCGGCTGACCGTCCTA
MH76 VL    GTGTTATTCGGAGGAGGGACCCGGCTCACCGTACTA
MH74 VL    GTGTTATTCGGAGGAGGGACCCGGCTCACCGTCCTA
MH36 VL    GGCTTATTCGGAGGAGGGACCCGGCTGACCGTCCTA
MH49 VL    CCGGTCTTCGGCGGAGGGACCCGGCTCACCGTCCTA
```

Figure 3

MH1- QLQLQESGPGLVKPSETLSLTCAVSGGSISGGYGWGWIRQPPGKGLEWVGSIYGSTGNTYYNPSLKSRVTISTDT

MH2- EVQLVESGGGLAKPGGSLRLSCAASGFTFSDYYMDWVRQAPGKGLEWVSRISNGGGSKWYADSVKGRFTISRE

MH36- EVQLVESGGGLVQPGGSLRLSCAASGFTFSNVWMNWVRQTPGKGLEWVARIKVKADGGTADYAASVKGRFTI

MH49- EAQLEESGPGLVKPSETLSLSCAVSGGSFRSYWWGWIRQPPGKGLEWIGSIYGSSGSTEYNPSLKSRATISRDTS

MH67- QVQLEQSGPGLVKPSETLSLSCAVSGGSFRSYWWGWIRQPPGKGLEWIGSIYGSSGSTEYNPSLKSRATISRDTS

MH73- QVQLQESGPGLVKPSETLSLTCAVSGGSLSSNYWSWIRQAPGKGLEWIGHIFGGGGTDYNPSLKSRVTISTDTS

MH74- EVQLVQSGAEVKRPGESLKISCKTSGYSFTSYWISWVRQMPGKGLEWMGAIDPTDSDTRYNPSFQGQVTISAD

MH75- QEQLVQSGGGLAKPGGSLRLSCADSGFTFSDHYMDWVRQAPGKGLEWVSRISTGGGTTWYADSVKGRFTISR

MH76- QVQLQESGGGLAKPGGSLRLSCAASGFTFSDYYMDWVRQAPGKGLDWVSRISNGGGTTWYADSVKGRFTISR

MH77- QVQLLESGPGLVKPSETLSLTCTVSGGSFSSSHWWNWIRQAPGKGLEWIGYITTSNGATYYNPSLKSRVTISTDT

MH1- SKNQLSLKVSSVTAADTAIYYCARARSGTLWFLEFWGQGAPVTASS

MH2- NAKNTLYLQMNSLRAEDTAVYYCAEVPTGYSQGVWGPGVLFTVSS

MH36- SRDDSKNTLYLQMNSLKTEDTAVYYCTTEEITVARYDYWGQGVLVTVSS

MH49- KNQFSLKLSSVTAADTAVYYCARQIQFLTDAFDFWGQGLRVTVSS

MH67- KNQFSLKLSSVTAADTAVYYCARQIQFLTDAFDFWGQGLRVTASS

MH73- KNQFSLKLSSLAAADTAVYYCARAAIMYPNRFDVWGPGVLVTASS

MH74- KSISTAYLQWSRLKASDTATYYCAKSDWSDYYGNSLDVWGRGVLVTASS

MH75- ENANNTLYLQMNSLRGEDTAVYYCAKVPTGYSQGVWGPGVLVTASS

MH76- ENAKNTLYLQMNSLRPEDTAVYYCATVPTATSGIGNWGQGVLVTASS

MH77- SKNQFSLKLSSVTAADSAVYFCARGYSNWDNWFDVWGPGVLVTVSS

Figure 4

MH1- QPVLTQPRSVSVSPGQTARITCGGDNIGSKSVQWYQQKPPQAPVLVIYADSERPSGIPERFSGSNSGNTATLTVS

MH2- QSVLTQPQSVSVSPGQTARISCGGDNIGSKNVHWYQQKPPQAPVLVIYAGTERPSGIPERFSGSNSGNTATLTISG

MH36- QSVLTQPPSASGAPGQSVTISCSGSSSNIRGNGVHWYQQLSGMAPKLLIYNNNQRPSGVPDRFSGSKSGTSASLAI

MH49- QPGLTQPPSASGAPGQSVTISCSGSSSDIGSHDVYWYQQLPGTAPKLLIYYSNQRPSGVPDRISGSKSGTSASLTIS

MH67- DIQLTQSPSSVSASVGDRVTITCRASQAISTYLAWYLQRPGKAPELLIYAATTLHTGVASGLTGSGSGTDFTLTLS

MH73- ELLMTQSPSSLSASVGDRVTISCRASQNIYSNLAWYQQKPGKTPKLLIYAASILQSGIPSRFSGSGSGTDYTLTITN

MH74- QSVLTQPPSVSGAPGQRVTISCTGSNSNIGAGYYVQWYQQLPGTAPKLLIYENNKRPSGVSDRFSGSKSGTSASL

MH75- QSVLTQPQSVSVSPGQTARITCGGDNIGSKNVHWYQQKPPQAPVLVIYAETERPSGIPERFSGSNSGNTATLTIS

MH76- QPGLTQPHSVSVSPGQTARITCGGDNIGSKNVHWYQQKPPQAPVLVIYADSERPSGIPERFSGSNSGNTATLTIS

MH77- DIQMSQSPSSLSASVGDKVTITCQASQSVSSWLAWYRQKPGKAPKPLIYKASSLEGGVPSRFSGSGSGTDFTLTIN

MH1- GVEAGDEADYYCQVWDSSSDHVLFGGGTRLTVLA

MH2- VEAGDEADYYCQVWDGTREHVLFGGGTRLTVLA

MH36- TGLQSEDEADYYCEAWDNSLSGGLFGGGTRLTVLA

MH49- GLRSEDEADYYCETWENSLSGPVFGGGTRLTVLA

MH67- ALQPVDVGTYYCQQFKTLPYTFGQGTKVDIKA

MH73- LQPEDFGTYYCQQGFGIPYTFGQGTKVEFKA

MH74- TITGLQSEDEADYYCQSYDSSLSVVLFGGGTRLTVLA

MH75- GVEAGDEADYYCQVWDGSSAHVLFAGGTRLTVLA

MH76- GVEAGDEADYYCQVWDSSSNHVLFGGGTRLTVL

MH77- SLQPEDFATYYCQQYNSVPYSFGHGTKVDIKA

SEQUENCE LISTING

<160> NUMBER OF SEQ ID NOS: 152

<210> SEQ ID NO 1
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H1 F

<400> SEQUENCE: 1
caggagcagc tggtgcagtc                                                         20

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H2 F

<400> SEQUENCE: 2
caggtccagc tggtgsagwc                                                         20

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H3 F

<400> SEQUENCE: 3
caggtscagc tcgagsagtc                                                         20

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H4 F

<400> SEQUENCE: 4
caggtgcagc tgcaggagtc                                                         20

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H5 F

<400> SEQUENCE: 5
cagctgcagc tgcagsagtc                                                         20

<210> SEQ ID NO 6

```
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H6 F

<400> SEQUENCE: 6
caggtgcagc trctcgagts                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H7 F

<400> SEQUENCE: 7
caggtscagc tggtgcagty                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H8 F

<400> SEQUENCE: 8
caggtsacct tgaaggagtc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H9 F

<400> SEQUENCE: 9
caggtccagc tgcaggaaag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H10 F

<400> SEQUENCE: 10
gaggtgcagy tggtggagwc                                               20

<210> SEQ ID NO 11
<211> LENGTH: 20
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: Primer - Lib-H11 F

<400> SEQUENCE: 11
gaggttcagy tggtkgaatc                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H12 F

<400> SEQUENCE: 12
gaggtgcagc tggtgsartc                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H13 F

<400> SEQUENCE: 13
gaggtgcagc tggyrgagtc                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H14 F

<400> SEQUENCE: 14
gaagtgcagy tggtggagtc                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H15 F

<400> SEQUENCE: 15
gaggtgcagc tcgaggagtc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-H16 F
```

<400> SEQUENCE: 16
gaggtgcagc tgctcgagtc                                               20

<210> SEQ ID NO 17
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - VH Rev1

<400> SEQUENCE: 17
ctgargagrc tgtgacc                                                  17

<210> SEQ ID NO 18
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - VH Rev2

<400> SEQUENCE: 18
ctgaggacac ggcaacc                                                  17

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K1 F

<400> SEQUENCE: 19
gatattgtga tgayccagac                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K2 F

<400> SEQUENCE: 20
gatactgtga tgacccagac                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K3 F

<400> SEQUENCE: 21
gatatygagc tcacbcagtc                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K4 F

<400> SEQUENCE: 22
gatgttgyra tgactcagtc                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer -  Lib-K5 F

<400> SEQUENCE: 23
gacattcagm tgwcccagtc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K6 F

<400> SEQUENCE: 24
gacgttcaga tgacccagtc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer -  Lib-K7 F

<400> SEQUENCE: 25
gacatccaga tgacccagtc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer -  Lib-K8 F

<400> SEQUENCE: 26
gagctccwga tgacmcagtc                                               20

<210> SEQ ID NO 27
<211> LENGTH: 20

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K9 F

<400> SEQUENCE: 27
gaaatwgtra tgacgcagtc                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K10 F

<400> SEQUENCE: 28
gaaatcgagc tcacrcagtc                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K11 F

<400> SEQUENCE: 29
caagttatat tgactcagtc                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K12 F

<400> SEQUENCE: 30
gacatcgagc tcacccagtc                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K13 F

<400> SEQUENCE: 31
gagctcgtgt tgacacagtc                                                20

<210> SEQ ID NO 32
<211> LENGTH: 24
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Primer - Lib-K1 Rev

<400> SEQUENCE: 32
yttgakatcc agtttggtcc cggg                                              24

<210> SEQ ID NO 33
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K2 Rev

<400> SEQUENCE: 33
tttgayctcc accytggtcc ctcc                                              24

<210> SEQ ID NO 34
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K3 Rev

<400> SEQUENCE: 34
tttgatstcc actttggtcc cctg                                              24

<210> SEQ ID NO 35
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K4 Rev

<400> SEQUENCE: 35
tytgatttcc accytggtcc cttg                                              24

<210> SEQ ID NO 36
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-K5 Rev

<400> SEQUENCE: 36
cttgatgtcc accttggtcc cgtg                                              24

<210> SEQ ID NO 37
<211> LENGTH: 24
<212> TYPE: DNA
<213> ORGANISM: Macaca mulatta

<400> SEQUENCE: 37
ttttagtacc accttggtcc cttg                                              24
```

```
<210> SEQ ID NO 38
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L1 F

<400> SEQUENCE: 38
cagccagkgc tgactcagcc                                         20

<210> SEQ ID NO 39
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L2 F

<400> SEQUENCE: 39
cagcctgkgc tgactcagyc                                         20

<210> SEQ ID NO 40
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L3 F

<400> SEQUENCE: 40
cagtctgtgy tgackcagcc                                         20

<210> SEQ ID NO 41
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L4 F

<400> SEQUENCE: 41
cagtctgccc tgactcagcc                                         20

<210> SEQ ID NO 42
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L5 F

<400> SEQUENCE: 42
cagtctgccc cgaytcagyc                                         20

<210> SEQ ID NO 43
<211> LENGTH: 20
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: Primer - Lib-L6 F

<400> SEQUENCE: 43
caggctgccc ygactcagyc                                       20

<210> SEQ ID NO 44
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L7 F

<400> SEQUENCE: 44
caggcagggc tgactcagcc                                       20

<210> SEQ ID NO 45
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L8 F

<400> SEQUENCE: 45
cagactgtgg tgacccagga                                       20

<210> SEQ ID NO 46
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L9 F

<400> SEQUENCE: 46
aagcctatgc tgactcagcc                                       20

<210> SEQ ID NO 47
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L10 F

<400> SEQUENCE: 47
tcttctgrgc tgactcagga                                       20

<210> SEQ ID NO 48
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: Primer - Lib-L11 F

<400> SEQUENCE: 48
tcctatgagc tgacwcagcc                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L12 F

<400> SEQUENCE: 49
cagsctgtgc tgactcagcc                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L13 F

<400> SEQUENCE: 50
cwgcctgtgc tgactcaryc                    20

<210> SEQ ID NO 51
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L1 Rev

<400> SEQUENCE: 51
tagracggts agccgggtc                     19

<210> SEQ ID NO 52
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer - Lib-L2 Rev

<400> SEQUENCE: 52
gaggayggtc aayttggtg                     19

<210> SEQ ID NO 53
<211> LENGTH: 360
<212> TYPE: DNA
<213> ORGANISM: Macaca mulatta

<400> SEQUENCE: 53
gaggcgcagc tcgaggagtc gggcccagga ctggtgaagc cttcggagac cctgtccctc    60
agttgcgctg tctctggtgg ctccttcagg agttactggt ggggctggat ccgccagccc   120
ccagggaagg gcctggagtg gattgggagt atctatggca gtagtgggag caccgaatac   180

```
aacccctccc tcaaaagtcg agccaccatt tcaagagaca cgtccaagaa ccagttctcc    240
ctgaagctga gctctgtgac cgccgcggac acggccgtct attactgtgc gaggcagata    300 caattttga ctgatgcttt tgatttctgg ggccaagggc tcaggtcac agtctcctca    360

<210> SEQ ID NO 54
<211> LENGTH: 360
<212> TYPE: DNA
<213> ORGANISM: Macaca mulatta

<400> SEQUENCE: 54
caggtgcagc tcgagcagtc gggcccagga ctggtgaagc cttcggagac cctgtccctc    60
agttgcgctg tctctggtgg ctccttcagg agttactggt ggggctggat ccgccagccc    120
ccagggaagg gcctggagtg gattgggagt atctatggca gtagtgggag caccgaatac    180
aacccctccc tcaaaagtcg agccaccatt tcaagagaca cgtccaagaa ccagttctcc    240
ctgaagctga gctctgtgac cgccgcggac acggccgtct attactgtgc gaggcagata    300 caattttga ctgatgcttt tgatttctgg ggccaagggc tcaggtcac agcctcctca    360

<210> SEQ ID NO 55
<211> LENGTH: 360
<212> TYPE: DNA
<213> ORGANISM: Macaca mulatta

<400> SEQUENCE: 55
caggtgcagc tgcaggagtc gggcccagga ctggtgaagc cttcggagac cctgtccctc    60
acctgcgctg tctctggtgg ctccctcagc agtaactact ggagctggat ccgccaggcc    120
ccagggaagg gactggagtg gattggacat atctttggtg gtggtggggg caccgactac    180
aacccctccc tcaagagtcg agtcaccatt tcaacagaca cgtccaagaa ccagttctcc    240
ctgaagctga gctctctggc cgccgcggac acggccgtgt attactgtgc gagagctgca    300
ataatgtacc ccaaccggtt cgatgtctgg ggcccgggag tcctggtcac agcctctagc    360

<210> SEQ ID NO 56
<211> LENGTH: 366
<212> TYPE: DNA
<213> ORGANISM: Macaca mulatta

<400> SEQUENCE: 56
gaggtgcagc tggtgcaatc tggagcagag gtgaaaaggc ccggggagtc actgaagatc    60
tcctgtaaga cttctggata cagctttacc agctactgga tcagctgggt cgcgcagatg    120
cccgggaaag gcctggagtg gatggggcg attgatccta ctgattctga taccagatac    180
aacccgtcct tccaaggcca ggtcaccatc tccgccgaca gtccatcag caccgcctac    240 ctgcagtgga gcaggctgaa ggcctcggac accgccacgt attactgtgc gaaatcagac    300
tggagtgatt attatggcaa ctcattggat gtctggggcc ggggagttct ggtcacagcc    360
tcttca                                                              366

<210> SEQ ID NO 57
<211> LENGTH: 354
<212> TYPE: DNA
<213> ORGANISM: Macaca mulatta

<400> SEQUENCE: 57
caggagcagc tggtgcagtc tgggggcggc ttggcaaagc ctgggggtc cctgagactc    60
```

```
tcctgcgcag actccggatt caccttcagt gaccactaca tggactgggt ccgccaggct      120
ccagggaagg ggctggagtg ggtctcacgt attagtactg gtggtggaac cacatggtac      180
gcagactccg tgaagggcag attcaccatc tccagagaga cgccaacaa cacactgtat       240 cttcaaatga acagcctgag aggtgaggac acggctgtct attactgtgc gaaagttccc      300
acgggataca gtcaaggggt ctgggggccg ggagtcctgg tcacagcctc ctca            354
```

<210> SEQ ID NO 58
<211> LENGTH: 357
<212> TYPE: DNA
<213> ORGANISM: Macaca mulatta

<400> SEQUENCE: 58

```
caggtgcagc tgcaggagtc tgggggcggc ttggcaaagc ctgggggtc cctgagactc       60 tcctgcgcag cctccggatt caccttcagt gactactaca tggactgggt ccgccaggct      120
ccagggaagg ggctggattg ggtctcacgc attagtaatg gtggtggtac cacatggtac      180
gcagactccg tgaagggcag attcaccatc tccagagaga cgccaagaa cacactgtat       240 cttcaaatga acagcctgag acctgaggac acggctgtct attactgtgc gacggtgccc      300
acagcgacat ctggaatagg caactggggc cagggagtcc tggtcacagc ctcctca        357
```

<210> SEQ ID NO 59
<211> LENGTH: 363
<212> TYPE: DNA
<213> ORGANISM: Macaca mulatta

<400> SEQUENCE: 59

```
caggtgcagc tgctcgagtc gggcccagga ctggtgaagc cttcagagac cctgtccctc      60
acctgcactg tctctggtgg ctctttcagt agtagtcatt ggtggaactg gatccgccag      120
gccccaggga aagggctgga gtggattggc tatatcacca ctagtaatgg tgccacctac      180
tacaacccct ccctcaagag tcgagtcacc atttcaacag acacgtccaa gaaccagttc      240
tccctgaaac tgagctctgt gaccgccgcg gactcggccg tgtatttctg tgcgagggga      300
tacagtaact gggacaactg gttcgatgtc tggggcccgg gagtcctggt cacagtctcc      360
tca                                                                    363
```

<210> SEQ ID NO 60
<211> LENGTH: 363
<212> TYPE: DNA
<213> ORGANISM: Macaca mulatta

<400> SEQUENCE: 60

```
cagctgcagc tgcaggagtc gggcccagga ctggtgaagc cttcagagac cctgtccctc      60
acttgcgctg tctctggtgg ctccatcagc ggtggttatg gctgggctg gatccgccag       120 cccccaggga aggggctgga gtgggttggg agtatctatg gtagtactgg gaacacctac      180 tacaaccct ccctcaagag tcgagtcacc atttcaacag acacgtccaa gaaccagctc       240
tccctgaagg tgagctctgt gaccgccgcg gacacggcca tctactactg tgcgagagcc     300
cgcagtggta ctttgtggtt cctcgagttc tggggccagg gcgccccggt cacagcatcc      360
tca                                                                    363
```

<210> SEQ ID NO 61
<211> LENGTH: 354
<212> TYPE: DNA
<213> ORGANISM: Macaca mulatta

```
<400> SEQUENCE: 61
gaggttcagt tggtggaatc tgggggcggc ttggcaaagc ctgggggtc cctgagactc    60 tcctgcgcag cctccggatt caccttcagt gactactaca tggactgggt ccgccaggct   120
ccagggaagg ggctggagtg ggtctcacgt attagtaatg gtggtggtag taaatggtac   180
gcagactccg tgaagggcag attcaccatc tccagagaga acgccaagaa cacactgtat   240
cttcaaatga acagcctgag agctgaggac acggctgtat attactgtgc ggaagttccc   300
acgggataca gtcaaggtgt ctggggcccg ggagtcctgt tcacagtctc ctca          354

<210> SEQ ID NO 62
<211> LENGTH: 363
<212> TYPE: DNA
<213> ORGANISM: Macaca mulatta

<400> SEQUENCE: 62
gaagtgcagc tggtggagtc tgggggaggc ttggtccagc ctgggggtc cctgaggctc    60 tcctgtgcag cctctggatt caccttcagt aacgtctgga tgaactgggt ccgccagact   120
ccagggaagg ggctagagtg ggttgcccgt attaaagtca aagctgacgg tggaacagca   180
gattacgccg cgtctgtgaa aggcagattc accatctcaa gagacgattc aaagaacaca   240
ctgtatctgc aaatgaacag tctgaaaacc gaggacacgg ccgtgtatta ctgcaccaca   300
gaggagatta cagtggcccg ttatgactac tggggccagg gagtcctggt cacagtctcc   360
tca                                                                363

<210> SEQ ID NO 63
<211> LENGTH: 324
<212> TYPE: DNA
<213> ORGANISM: Macaca mulatta

<400> SEQUENCE: 63
cagcctgtgc tgactcagcc acgctcagtg tccgtgtccc caggacagac ggccaggatc    60
acctgtgggg gagacaacat tggaagtaaa agtgtgcagt ggtaccagca gaagccaccg   120
caggcccctg tgctggtcat ctatgctgat agcgaacggc cctcaggaat ccctgagcga   180
ttctctggct ccaactcagg gaacaccgcc accctgaccg tcagcggggt cgaggccggg   240
gatgaggctg actattactg tcaggtgtgg gacagtagta gtgatcatgt gttattcgga   300
ggagggaccc ggctgaccgt ccta                                          324

<210> SEQ ID NO 64
<211> LENGTH: 324
<212> TYPE: DNA
<213> ORGANISM: Macaca mulatta

<400> SEQUENCE: 64
cagtctgtgt tgactcagcc acaatcggtg tcggtgtccc caggacagac ggccaggatc    60
tcctgtgggg gagacaacat tggaagtaaa aatgtgcact ggtaccagca gaagccaccg   120
caggcccctg tgctggtcat ctatgctgga accgaacggc cctcagggat ccctgagcga   180
ttctctggct ccaactccgg gaacacgccc accctgacca tcagcggggt cgaggccggg   240
gatgaggcgg actattactg tcaggtgtgg gacggtaccc gtgagcatgt attattcgga   300
ggagggaccc ggctcaccgt ccta                                          324

<210> SEQ ID NO 65
```

```
<211> LENGTH: 330
<212> TYPE: DNA
<213> ORGANISM: Macaca mulatta

<400> SEQUENCE: 65
cagtctgtgt tgactcagcc accctcagcg tctggggctc ccgggcagag tgtcaccatc      60
tcttgctctg gaagcagctc caacatcaga ggtaatggtg tacactggta ccagcagctc     120
tcaggaatgg cccccaaact cctcatctat aataataatc agcgaccctc agggtccct      180 gaccgattct ctggctccaa gtctggcacg tcagcctccc tggccatcac tggtctccag    240
tctgaggatg aggccgatta ttactgcgag catgggata acagcctgag cggtggctta    300
ttcggaggag ggacccggct gaccgtccta                                      330

<210> SEQ ID NO 66
<211> LENGTH: 330
<212> TYPE: DNA
<213> ORGANISM: Macaca mulatta

<400> SEQUENCE: 66
cagccagggc tgactcagcc tccctcagcg tctggggctc ccgggcagag tgtcaccatc      60
tcttgctctg gaagcagctc tgacattgga agtcatgacg tctactggta ccagcagctc    120
ccagggacgg cccccaagct cctcatctac tacagtaatc agcgaccctc agggtccct      180 gaccgaatct ctggctccaa gtctggcacg tcagcctccc tgaccatcag cggtctccgg    240
tccgaggatg aggctgatta ttactgtgaa acatgggaaa acagcctgag cggtccggtc    300
ttcggcggag ggacccggct caccgtccta                                      330

<210> SEQ ID NO 67
<211> LENGTH: 321
<212> TYPE: DNA
<213> ORGANISM: Macaca mulatta

<400> SEQUENCE: 67
gacattcagc tgacccagtc tccatcctcc gtgtctgctt ctgtgggaga cagagtcacc      60
atcacttgtc gggcgagtca ggccatcagt acttatttag cctggtatct acagaggccg    120
gggaaagccc ctgaactcct gatctattat gcaaccactt acacactgg ggtcgcttca    180 ggtctcactg gcagtggatc tgggacggat ttcactctca ccctcagtgc cctgcaacct    240
gtagatgttg aacttacta ctgtcaacag tttaaaactt accgtacac ttttggccag     300 gggaccaaag tggacatcaa a                                               321

<210> SEQ ID NO 68
<211> LENGTH: 321
<212> TYPE: DNA
<213> ORGANISM: Macaca mulatta

<400> SEQUENCE: 68
gagctcctga tgacacagtc tccatcctcc ctgtctgcat ctgtaggaga cagagtcacc      60
atctcttgcc gggcaagtca gaacatttat agtaatttag cgtggtatca gcagaaacca    120
gggaaaactc ctaagctcct gatctatgct gcatccatct gcagagtgg gattccctct    180 cggttcagcg gcagcggatc tgggacagat tacactctca ccatcaccaa cctgcagcct    240 gaagatttg aacttatta ctgtcagcaa ggttttggta tccctacac ttttggccag     300 gggaccaaag tggagttcaa a                                               321
```

<210> SEQ ID NO 69
<211> LENGTH: 333
<212> TYPE: DNA
<213> ORGANISM: Macaca mulatta

<400> SEQUENCE: 69

```
cagtctgtgt tgactcagcc gccctcagtg tctggggcgc caggacagag ggtcaccatc      60
tcctgcactg gagtaattc caacatcggg gcgggttatt atgtgcagtg gtaccagcag     120
cttccaggaa cggcccccaa actcctcatc tatgaaaata taagcgacc ctcagggggtt    180
tctgatcgat tctctggctc caagtctggt acctcagcct ccctgaccat cactggactt    240
cagtctgagg atgaggctga ctattactgc cagtcctatg acagcagcct gagtgttgtg    300
ttattcggag agggacccg gctcaccgtc cta                                   333
```

<210> SEQ ID NO 70
<211> LENGTH: 324
<212> TYPE: DNA
<213> ORGANISM: Macaca mulatta

<400> SEQUENCE: 70

```
cagtctgtgt tgactcagcc acaatcggtg tcggtgtccc caggacagac ggccaggatc      60
acctgtgggg gagacaacat tggaagtaaa aatgtgcact ggtaccagca gaagccaccg     120
caggccctg tgctggtcat ctatgctgaa accgagcggc cctcagggat ccctgagcga     180
ttctctggct ccaactccgg gaacacggcc accctgacca tcagcggagt cgaggccggg     240
gatgaggcgg actattactg tcaggtgtgg gacggtagca gtgcacatgt attattcgca     300
ggagggaccc ggctgaccgt ccta                                            324
```

<210> SEQ ID NO 71
<211> LENGTH: 324
<212> TYPE: DNA
<213> ORGANISM: Macaca mulatta

<400> SEQUENCE: 71

```
cagccagggc tgactcagcc acactcggtg tcggtgtccc caggacagac ggccaggatc      60
acctgtgggg gagacaacat tggaagtaaa aatgtgcact ggtaccagca gaagccaccg     120
caggccctg tgctggtcat ctatgctgat agcgaacggc cctcagggat ccctgagcga     180
ttctctggct ccaactccgg gaacacggcc accctgacca tcagcggggt cgaggccggg     240
gatgaggctg actattactg tcaggtgtgg gacagtagca gtaatcatgt gttattcgga     300
ggagggaccc ggctcaccgt acta                                            324
```

<210> SEQ ID NO 72
<211> LENGTH: 321
<212> TYPE: DNA
<213> ORGANISM: Macaca mulatta

<400> SEQUENCE: 72

```
gacattcaga tgtcccagtc tccttcctcc ctgtctgcat ctgtgggaga caaagtcacc      60
atcacttgcc aggcaagtca gagtgttagc agctggttag cctggtatcg gcagaaacca     120
gggaaggccc ctaagcccct gatctataag gcatccagtt tggaaggtgg ggtcccctca     180
aggttcagcg gcagtggatc tgggacagat ttcactctca ccatcaacag cctgcagcct     240
gaagattttg caacttatta ctgtcaacag tataacagtg tgccgtacag ttttggccac     300
gggaccaagg tggacatcaa g                                               321
```

<210> SEQ ID NO 73
<211> LENGTH: 121
<212> TYPE: PRT
<213> ORGANISM: Macaca mulatta

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Gly Trp Gly Trp Ile Arg Gln Pro Pro Gly Lys Gly Leu Glu Trp
        35                  40                  45

Val Gly Ser Ile Tyr Gly Ser Thr Gly Asn Thr Tyr Tyr Asn Pro Ser
    50                  55                  60

Leu Lys Ser Arg Val Thr Ile Ser Thr Asp Thr Ser Lys Asn Gln Leu
65                  70                  75                  80

Ser Leu Lys Val Ser Ser Val Thr Ala Ala Asp Thr Ala Ile Tyr Tyr
                85                  90                  95

Cys Ala Arg Ala Arg Ser Gly Thr Leu Trp Phe Leu Glu Phe Trp Gly
            100                 105                 110

Gln Gly Ala Pro Val Thr Ala Ser Ser
            115                 120

<210> SEQ ID NO 74
<211> LENGTH: 118
<212> TYPE: PRT
<213> ORGANISM: Macaca mulatta

<400> SEQUENCE: 74

Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Glu Trp Val
        35                  40                  45

Ser Arg Ile Ser Asn Gly Gly Ser Lys Trp Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Val Pro Thr Gly Tyr Ser Gln Gly Val Trp Gly Pro Gly Val
            100                 105                 110

Leu Phe Thr Val Ser Ser
            115

<210> SEQ ID NO 75
<211> LENGTH: 121
<212> TYPE: PRT
<213> ORGANISM: Macaca mulatta

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Val
            20                  25                  30

Trp Met Asn Trp Val Arg Gln Thr Pro Gly Lys Gly Leu Glu Trp Val

```
                35                  40                  45
Ala Arg Ile Lys Val Lys Ala Asp Gly Gly Thr Ala Asp Tyr Ala Ala
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Glu Glu Ile Thr Val Ala Arg Tyr Asp Tyr Trp Gly
            100                 105                 110
Gln Gly Val Leu Val Thr Val Ser Ser
        115                 120

<210> SEQ ID NO 76
<211> LENGTH: 120
<212> TYPE: PRT
<213> ORGANISM: Macaca mulatta

<400> SEQUENCE: 76

Glu Ala Gln Leu Glu Glu Ser Gly Pro Gly Leu Val Lys Pro Ser Glu
1               5                   10                  15
Thr Leu Ser Leu Ser Cys Ala Val Ser Gly Gly Ser Phe Arg Ser Tyr
            20                  25                  30
Trp Trp Gly Trp Ile Arg Gln Pro Pro Gly Lys Gly Leu Glu Trp Ile
        35                  40                  45
Gly Ser Ile Tyr Gly Ser Ser Gly Ser Thr Glu Tyr Asn Pro Ser Leu
    50                  55                  60
Lys Ser Arg Ala Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gln Ile Gln Phe Leu Thr Asp Ala Phe Asp Phe Trp Gly Gln
            100                 105                 110
Gly Leu Arg Val Thr Val Ser Ser
        115                 120

<210> SEQ ID NO 77
<211> LENGTH: 120
<212> TYPE: PRT
<213> ORGANISM: Macaca mulatta

<400> SEQUENCE: 77

Gln Val Gln Leu Glu Gln Ser Gly Pro Gly Leu Val Lys Pro Ser Glu
1               5                   10                  15
Thr Leu Ser Leu Ser Cys Ala Val Ser Gly Gly Ser Phe Arg Ser Tyr
            20                  25                  30
Trp Trp Gly Trp Ile Arg Gln Pro Pro Gly Lys Gly Leu Glu Trp Ile
        35                  40                  45
Gly Ser Ile Tyr Gly Ser Ser Gly Ser Thr Glu Tyr Asn Pro Ser Leu
    50                  55                  60
Lys Ser Arg Ala Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gln Ile Gln Phe Leu Thr Asp Ala Phe Asp Phe Trp Gly Gln
            100                 105                 110
Gly Leu Arg Val Thr Ala Ser Ser
```

<210> SEQ ID NO 78
<211> LENGTH: 120
<212> TYPE: PRT
<213> ORGANISM: Macaca mulatta

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Leu Ser Ser Asn
            20                  25                  30

Tyr Trp Ser Trp Ile Arg Gln Ala Pro Gly Lys Gly Leu Glu Trp Ile
        35                  40                  45

Gly His Ile Phe Gly Gly Gly Gly Thr Asp Tyr Asn Pro Ser Leu
    50                  55                  60

Lys Ser Arg Val Thr Ile Ser Thr Asp Thr Ser Lys Asn Gln Phe Ser
65                  70                  75                  80

Leu Lys Leu Ser Ser Leu Ala Ala Asp Thr Ala Val Tyr Tyr Cys
                85                  90                  95

Ala Arg Ala Ala Ile Met Tyr Pro Asn Arg Phe Asp Val Trp Gly Pro
            100                 105                 110

Gly Val Leu Val Thr Ala Ser Ser
        115                 120

<210> SEQ ID NO 79
<211> LENGTH: 122
<212> TYPE: PRT
<213> ORGANISM: Macaca mulatta

<400> SEQUENCE: 79

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ala Ile Asp Pro Thr Asp Ser Asp Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Arg Leu Lys Ala Ser Asp Thr Ala Thr Tyr Tyr Cys
                85                  90                  95

Ala Lys Ser Asp Trp Ser Asp Tyr Tyr Gly Asn Ser Leu Asp Val Trp
            100                 105                 110

Gly Arg Gly Val Leu Val Thr Ala Ser Ser
        115                 120

<210> SEQ ID NO 80
<211> LENGTH: 118
<212> TYPE: PRT
<213> ORGANISM: Macaca mulatta

<400> SEQUENCE: 80

Gln Glu Gln Leu Val Gln Ser Gly Gly Gly Leu Ala Lys Pro Gly Gly
1               5                   10                  15

Ser Leu Arg Leu Ser Cys Ala Asp Ser Gly Phe Thr Phe Ser Asp His
            20                  25                  30

Tyr Met Asp Trp Val Arg Gln Ala Pro Gly Lys Gly Leu Glu Trp Val
            35                  40                  45

Ser Arg Ile Ser Thr Gly Gly Thr Thr Trp Tyr Ala Asp Ser Val
    50                  55                  60

Lys Gly Arg Phe Thr Ile Ser Arg Glu Asn Ala Asn Asn Thr Leu Tyr
65                  70                  75                  80

Leu Gln Met Asn Ser Leu Arg Gly Glu Asp Thr Ala Val Tyr Tyr Cys
                85                  90                  95

Ala Lys Val Pro Thr Gly Tyr Ser Gln Gly Val Trp Gly Gln Gly Val
                100                 105                 110

Leu Val Thr Ala Ser Ser
            115

<210> SEQ ID NO 81
<211> LENGTH: 119
<212> TYPE: PRT
<213> ORGANISM: Macaca mulatta

<400> SEQUENCE: 81

Gln Val Gln Leu Gln Glu Ser Gly Gly Gly Leu Ala Lys Pro Gly Gly
1               5                   10                  15

Ser Leu Arg Leu Ser Cys Ala Ala Ser Gly Phe Thr Phe Ser Asp Tyr
                20                  25                  30

Tyr Met Asp Trp Val Arg Gln Ala Pro Gly Lys Gly Leu Asp Trp Val
            35                  40                  45

Ser Arg Ile Ser Asn Gly Gly Thr Thr Trp Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Thr Val Pro Thr Ala Thr Ser Gly Ile Gly Asn Trp Gly Gln Gly
                100                 105                 110

Val Leu Val Thr Ala Ser Ser
            115

<210> SEQ ID NO 82
<211> LENGTH: 121
<212> TYPE: PRT
<213> ORGANISM: Macaca mulatta

<400> SEQUENCE: 82

Gln Val Gln Leu Leu Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
                20                  25                  30

His Trp Trp Asn Trp Ile Arg Gln Ala Pro Gly Lys Gly Leu Glu Trp
            35                  40                  45

Ile Gly Tyr Ile Thr Thr Ser Asn Gly Ala Thr Tyr Tyr Asn Pro Ser
    50                  55                  60

Leu Lys Ser Arg Val Thr Ile Ser Thr Asp Thr Ser Lys Asn Gln Phe
65                  70                  75                  80

Ser Leu Lys Leu Ser Ser Val Thr Ala Ala Asp Ser Ala Val Tyr Phe
                85                  90                  95

Cys Ala Arg Gly Tyr Ser Asn Trp Asp Asn Trp Phe Asp Val Trp Gly
                100                 105                 110

-continued

Pro Gly Val Leu Val Thr Val Ser Ser
        115                 120

<210> SEQ ID NO 83
<211> LENGTH: 109
<212> TYPE: PRT
<213> ORGANISM: Macaca mulatta

<400> SEQUENCE: 83

Gln Pro Val Leu Thr Gln Pro Arg Ser Val Ser Val Ser Pro Gly Gln
1               5                   10                  15

Thr Ala Arg Ile Thr Cys Gly Gly Asp Asn Ile Gly Ser Lys Ser Val
            20                  25                  30

Gln Trp Tyr Gln Gln Lys Pro Pro Gln Ala Pro Val Leu Val Ile Tyr
        35                  40                  45

Ala Asp Ser Glu Arg Pro Ser Gly Ile Pro Glu Arg Phe Ser Gly Ser
    50                  55                  60

Asn Ser Gly Asn Thr Ala Thr Leu Thr Val Ser Gly Val Glu Ala Gly
65                  70                  75                  80

Asp Glu Ala Asp Tyr Tyr Cys Gln Val Trp Asp Ser Ser Ser Asp His
                85                  90                  95

Val Leu Phe Gly Gly Gly Thr Arg Leu Thr Val Leu Ala
            100                 105

<210> SEQ ID NO 84
<211> LENGTH: 109
<212> TYPE: PRT
<213> ORGANISM: Macaca mulatta

<400> SEQUENCE: 84

Gln Ser Val Leu Thr Gln Pro Gln Ser Val Ser Val Ser Pro Gly Gln
1               5                   10                  15

Thr Ala Arg Ile Ser Cys Gly Gly Asp Asn Ile Gly Ser Lys Asn Val
            20                  25                  30

His Trp Tyr Gln Gln Lys Pro Pro Gln Ala Pro Val Leu Val Ile Tyr
        35                  40                  45

Ala Gly Thr Glu Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Gly Thr Arg Glu His
                85                  90                  95

Val Leu Phe Gly Gly Gly Thr Arg Leu Thr Val Leu Ala
            100                 105

<210> SEQ ID NO 85
<211> LENGTH: 111
<212> TYPE: PRT
<213> ORGANISM: Macaca mulatta

<400> SEQUENCE: 85

Gln Ser Val Leu Thr Gln Pro Pro Ser Ala Ser Gly Ala Pro Gly Gln
1               5                   10                  15

Ser Val Thr Ile Ser Cys Ser Gly Ser Ser Asn Ile Arg Gly Asn
            20                  25                  30

Gly Val His Trp Tyr Gln Gln Leu Ser Gly Met Ala Pro Lys Leu Leu
        35                  40                  45

```
Ile Tyr Asn Asn Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Glu Ala Trp Asp Asn Ser Leu
                 85                  90                  95

Ser Gly Gly Leu Phe Gly Gly Gly Thr Arg Leu Thr Val Leu Ala
            100                 105                 110

<210> SEQ ID NO 86
<211> LENGTH: 111
<212> TYPE: PRT
<213> ORGANISM: Macaca mulatta

<400> SEQUENCE: 86

Gln Pro Gly Leu Thr Gln Pro Pro Ser Ala Ser Gly Ala Pro Gly Gln
 1               5                  10                  15

Ser Val Thr Ile Ser Cys Ser Gly Ser Ser Asp Ile Gly Ser His
             20                  25                  30

Asp Val Tyr Trp Tyr Gln Gln Leu Pro Gly Thr Ala Pro Lys Leu Leu
             35                  40                  45

Ile Tyr Tyr Ser Asn Gln Arg Pro Ser Gly Val Pro Asp Arg Ile Ser
 50                  55                  60

Gly Ser Lys Ser Gly Thr Ser Ala Ser Leu Thr Ile Ser Gly Leu Arg
 65                  70                  75                  80

Ser Glu Asp Glu Ala Asp Tyr Tyr Cys Glu Thr Trp Glu Asn Ser Leu
                 85                  90                  95

Ser Gly Pro Val Phe Gly Gly Gly Thr Arg Leu Thr Val Leu Ala
            100                 105                 110

<210> SEQ ID NO 87
<211> LENGTH: 108
<212> TYPE: PRT
<213> ORGANISM: Macaca mulatta

<400> SEQUENCE: 87

Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Ala Ile Ser Thr Tyr
             20                  25                  30

Leu Ala Trp Tyr Leu Gln Arg Pro Gly Lys Ala Pro Glu Leu Leu Ile
             35                  40                  45

Tyr Tyr Ala Thr Thr Leu His Thr Gly Val Ala Ser Gly Leu Thr Gly
 50                  55                  60

Ser Gly Ser Gly Thr Asp Phe Thr Leu Thr Leu Ser Ala Leu Gln Pro
 65                  70                  75                  80

Val Asp Val Gly Thr Tyr Tyr Cys Gln Gln Phe Lys Thr Leu Pro Tyr
                 85                  90                  95

Thr Phe Gly Gln Gly Thr Lys Val Asp Ile Lys Ala
            100                 105

<210> SEQ ID NO 88
<211> LENGTH: 108
<212> TYPE: PRT
<213> ORGANISM: Macaca mulatta

<400> SEQUENCE: 88

Glu Leu Leu Met Thr Gln Ser Pro Ser Ser Leu Ser Ala Ser Val Gly
```

```
                1               5                  10                 15
          Asp Arg Val Thr Ile Ser Cys Arg Ala Ser Gln Asn Ile Tyr Ser Asn
                            20                  25                 30

Leu Ala Trp Tyr Gln Gln Lys Pro Gly Lys Thr Pro Lys Leu Leu Ile
                      35                  40                  45

Tyr Ala Ala Ser Ile Leu Gln Ser Gly Ile Pro Ser Arg Phe Ser Gly
                      50                  55                  60

Ser Gly Ser Gly Thr Asp Tyr Thr Leu Thr Ile Thr Asn Leu Gln Pro
          65                  70                  75                  80

Glu Asp Phe Gly Thr Tyr Tyr Cys Gln Gln Gly Phe Gly Ile Pro Tyr
                          85                  90                  95

Thr Phe Gly Gln Gly Thr Lys Val Glu Phe Lys Ala
                          100                 105
```

<210> SEQ ID NO 89
<211> LENGTH: 112
<212> TYPE: PRT
<213> ORGANISM: Macaca mulatta

<400> SEQUENCE: 89

```
          Gln Ser Val Leu Thr Gln Pro Pro Ser Val Ser Ala Pro Gly Gln
          1               5                   10                  15

Arg Val Thr Ile Ser Cys Thr Gly Ser Asn Ser Asn Ile Gly Ala Gly
                          20                  25                  30

Tyr Tyr Val Gln Trp Tyr Gln Gln Leu Pro Gly Thr Ala Pro Lys Leu
                      35                  40                  45

Leu Ile Tyr Glu Asn Asn Lys Arg Pro Ser Gly Val Ser Asp Arg Phe
                      50                  55                  60

Ser Gly Ser Lys Ser Gly Thr Ser Ala Ser Leu Thr Ile Thr Gly Leu
          65                  70                  75                  80

Gln Ser Glu Asp Glu Ala Asp Tyr Tyr Cys Gln Ser Tyr Asp Ser Ser
                          85                  90                  95

Leu Ser Val Val Leu Phe Gly Gly Gly Thr Arg Leu Thr Val Leu Ala
                          100                 105                 110
```

<210> SEQ ID NO 90
<211> LENGTH: 109
<212> TYPE: PRT
<213> ORGANISM: Macaca mulatta

<400> SEQUENCE: 90

```
          Gln Ser Val Leu Thr Gln Pro Gln Ser Val Ser Pro Gly Gln
          1               5                   10                  15

Thr Ala Arg Ile Thr Cys Gly Gly Asp Asn Ile Gly Ser Lys Asn Val
                          20                  25                  30

His Trp Tyr Gln Gln Lys Pro Pro Gln Ala Pro Val Leu Val Ile Tyr
                      35                  40                  45

Ala Glu Thr Glu Arg Pro Ser Gly Ile Pro Glu Arg Phe Ser Gly Ser
                      50                  55                  60

Asn Ser Gly Asn Thr Ala Thr Leu Thr Ile Ser Gly Val Glu Ala Gly
          65                  70                  75                  80

Asp Glu Ala Asp Tyr Tyr Cys Gln Val Trp Asp Gly Ser Ser Ala His
                          85                  90                  95

Val Leu Phe Ala Gly Gly Thr Arg Leu Thr Val Leu Ala
                          100                 105
```

```
<210> SEQ ID NO 91
<211> LENGTH: 107
<212> TYPE: PRT
<213> ORGANISM: Macaca mulatta

<400> SEQUENCE: 91

Gln Pro Gly Leu Thr Gln Pro His Ser Val Ser Val Ser Pro Gly Gln
1               5                   10                  15

Thr Ala Arg Ile Thr Cys Gly Gly Asp Asn Ile Gly Ser Lys Asn Val
            20                  25                  30

His Trp Tyr Gln Gln Lys Pro Pro Gln Ala Pro Val Leu Val Ile Tyr
        35                  40                  45

Ala Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Asn His
                85                  90                  95

Val Leu Phe Gly Gly Gly Thr Arg Leu Thr Val
            100                 105

<210> SEQ ID NO 92
<211> LENGTH: 108
<212> TYPE: PRT
<213> ORGANISM: Macaca mulatta

<400> SEQUENCE: 92

Asp Ile Gln Met Ser Gln Ser Pro Ser Ser Leu Ser Ala Ser Val Gly
1               5                   10                  15

Asp Lys Val Thr Ile Thr Cys Gln Ala Ser Gln Ser Val Ser Ser Trp
            20                  25                  30

Leu Ala Trp Tyr Arg Gln Lys Pro Gly Lys Ala Pro Lys Pro Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Tyr Asn Ser Val Pro Tyr
                85                  90                  95

Ser Phe Gly His Gly Thr Lys Val Asp Ile Lys Ala
            100                 105

<210> SEQ ID NO 93
<211> LENGTH: 7
<212> TYPE: PRT
<213> ORGANISM: Macaca mulatta

<400> SEQUENCE: 93

Ser Gly Gly Tyr Gly Trp Gly
1               5

<210> SEQ ID NO 94
<211> LENGTH: 17
<212> TYPE: PRT
<213> ORGANISM: Macaca mulatta

<400> SEQUENCE: 94

Ser Ile Tyr Gly Ser Thr Gly Asn Thr Tyr Tyr Asn Pro Ser Leu Lys
1               5                   10                  15
```

Ser

<210> SEQ ID NO 95
<211> LENGTH: 11
<212> TYPE: PRT
<213> ORGANISM: Macaca mulatta

<400> SEQUENCE: 95

Ala Arg Ser Gly Thr Leu Trp Phe Leu Glu Phe
1               5                   10

<210> SEQ ID NO 96
<211> LENGTH: 6
<212> TYPE: PRT
<213> ORGANISM: Macaca mulatta

<400> SEQUENCE: 96

Ser Asp Tyr Tyr Met Asp
1               5

<210> SEQ ID NO 97
<211> LENGTH: 17
<212> TYPE: PRT
<213> ORGANISM: Macaca mulatta

<400> SEQUENCE: 97

Arg Ile Ser Asn Gly Gly Gly Ser Lys Trp Tyr Ala Asp Ser Val Lys
1               5                   10                  15

Gly

<210> SEQ ID NO 98
<211> LENGTH: 9
<212> TYPE: PRT
<213> ORGANISM: Macaca mulatta

<400> SEQUENCE: 98

Val Pro Thr Gly Tyr Ser Gln Gly Val
1               5

<210> SEQ ID NO 99
<211> LENGTH: 6
<212> TYPE: PRT
<213> ORGANISM: Macaca mulatta

<400> SEQUENCE: 99

Ser Asn Val Trp Met Asn
1               5

<210> SEQ ID NO 100
<211> LENGTH: 19
<212> TYPE: PRT
<213> ORGANISM: Macaca mulatta

<400> SEQUENCE: 100

Arg Ile Lys Val Lys Ala Asp Gly Gly Thr Ala Asp Tyr Ala Ala Ser
1               5                   10                  15

Val Lys Gly

<210> SEQ ID NO 101
<211> LENGTH: 10
<212> TYPE: PRT
<213> ORGANISM: Macaca mulatta

<400> SEQUENCE: 101

```
Glu Glu Ile Thr Val Ala Arg Tyr Asp Tyr
1               5                   10
```

<210> SEQ ID NO 102
<211> LENGTH: 6
<212> TYPE: PRT
<213> ORGANISM: Macaca mulatta

<400> SEQUENCE: 102

```
Arg Ser Tyr Trp Trp Gly
1               5
```

<210> SEQ ID NO 103
<211> LENGTH: 17
<212> TYPE: PRT
<213> ORGANISM: Macaca mulatta

<400> SEQUENCE: 103

```
Ser Ile Tyr Gly Ser Ser Gly Ser Thr Glu Tyr Asn Pro Ser Leu Lys
1               5                   10                  15

Ser
```

<210> SEQ ID NO 104
<211> LENGTH: 11
<212> TYPE: PRT
<213> ORGANISM: Macaca mulatta

<400> SEQUENCE: 104

```
Gln Ile Gln Phe Leu Thr Asp Ala Phe Asp Phe
1               5                   10
```

<210> SEQ ID NO 105
<211> LENGTH: 6
<212> TYPE: PRT
<213> ORGANISM: Macaca mulatta

<400> SEQUENCE: 105

```
Arg Ser Tyr Trp Trp Gly
1               5
```

<210> SEQ ID NO 106
<211> LENGTH: 17
<212> TYPE: PRT
<213> ORGANISM: Macaca mulatta

<400> SEQUENCE: 106

```
Ser Ile Tyr Gly Ser Ser Gly Ser Thr Glu Tyr Asn Pro Ser Leu Lys
1               5                   10                  15

Ser
```

<210> SEQ ID NO 107
<211> LENGTH: 11
<212> TYPE: PRT
<213> ORGANISM: Macaca mulatta

<400> SEQUENCE: 107

```
Gln Ile Gln Phe Leu Thr Asp Ala Phe Asp Phe
1               5                   10
```

<210> SEQ ID NO 108
<211> LENGTH: 6
<212> TYPE: PRT
<213> ORGANISM: Macaca mulatta

```
<400> SEQUENCE: 108

Ser Ser Asn Tyr Trp Ser
1               5

<210> SEQ ID NO 109
<211> LENGTH: 17
<212> TYPE: PRT
<213> ORGANISM: Macaca mulatta

<400> SEQUENCE: 109

His Ile Phe Gly Gly Gly Gly Thr Asp Tyr Asn Pro Ser Leu Lys
1               5                   10                  15

Ser

<210> SEQ ID NO 110
<211> LENGTH: 11
<212> TYPE: PRT
<213> ORGANISM: Macaca mulatta

<400> SEQUENCE: 110

Ala Ala Ile Met Tyr Pro Asn Arg Phe Asp Val
1               5                   10

<210> SEQ ID NO 111
<211> LENGTH: 6
<212> TYPE: PRT
<213> ORGANISM: Macaca mulatta

<400> SEQUENCE: 111

Thr Ser Tyr Trp Ile Ser
1               5

<210> SEQ ID NO 112
<211> LENGTH: 17
<212> TYPE: PRT
<213> ORGANISM: Macaca mulatta

<400> SEQUENCE: 112

Ala Ile Asp Pro Thr Asp Ser Asp Thr Arg Tyr Asn Pro Ser Phe Gln
1               5                   10                  15

Gly

<210> SEQ ID NO 113
<211> LENGTH: 13
<212> TYPE: PRT
<213> ORGANISM: Macaca mulatta

<400> SEQUENCE: 113

Ser Asp Trp Ser Asp Tyr Tyr Gly Asn Ser Leu Asp Val
1               5                   10

<210> SEQ ID NO 114
<211> LENGTH: 6
<212> TYPE: PRT
<213> ORGANISM: Macaca mulatta

<400> SEQUENCE: 114

Ser Asp His Tyr Met Asp
1               5

<210> SEQ ID NO 115
<211> LENGTH: 17
```

```
<212> TYPE: PRT
<213> ORGANISM: Macaca mulatta

<400> SEQUENCE: 115

Arg Ile Ser Thr Gly Gly Gly Thr Thr Trp Tyr Ala Asp Ser Val Lys
1               5                   10                  15

Gly

<210> SEQ ID NO 116
<211> LENGTH: 9
<212> TYPE: PRT
<213> ORGANISM: Macaca mulatta

<400> SEQUENCE: 116

Val Pro Thr Gly Tyr Ser Gln Gly Val
1               5

<210> SEQ ID NO 117
<211> LENGTH: 6
<212> TYPE: PRT
<213> ORGANISM: Macaca mulatta

<400> SEQUENCE: 117

Ser Asp Tyr Tyr Met Asp
1               5

<210> SEQ ID NO 118
<211> LENGTH: 17
<212> TYPE: PRT
<213> ORGANISM: Macaca mulatta

<400> SEQUENCE: 118

Arg Ile Ser Asn Gly Gly Gly Thr Thr Trp Tyr Ala Asp Ser Val Lys
1               5                   10                  15

Gly

<210> SEQ ID NO 119
<211> LENGTH: 10
<212> TYPE: PRT
<213> ORGANISM: Macaca mulatta

<400> SEQUENCE: 119

Val Pro Thr Ala Thr Ser Gly Ile Gly Asn
1               5                   10

<210> SEQ ID NO 120
<211> LENGTH: 7
<212> TYPE: PRT
<213> ORGANISM: Macaca mulatta

<400> SEQUENCE: 120

Ser Ser Ser His Trp Trp Asn
1               5

<210> SEQ ID NO 121
<211> LENGTH: 17
<212> TYPE: PRT
<213> ORGANISM: Macaca mulatta

<400> SEQUENCE: 121

Tyr Ile Thr Thr Ser Asn Gly Ala Thr Tyr Tyr Asn Pro Ser Leu Lys
1               5                   10                  15

Ser
```

```
<210> SEQ ID NO 122
<211> LENGTH: 11
<212> TYPE: PRT
<213> ORGANISM: Macaca mulatta

<400> SEQUENCE: 122

Gly Tyr Ser Asn Trp Asp Asn Trp Phe Asp Val
1               5                   10

<210> SEQ ID NO 123
<211> LENGTH: 10
<212> TYPE: PRT
<213> ORGANISM: Macaca mulatta

<400> SEQUENCE: 123

Gly Asp Asn Ile Gly Ser Lys Ser Val Gln
1               5                   10

<210> SEQ ID NO 124
<211> LENGTH: 7
<212> TYPE: PRT
<213> ORGANISM: Macaca mulatta

<400> SEQUENCE: 124

Ala Asp Ser Glu Arg Pro Ser
1               5

<210> SEQ ID NO 125
<211> LENGTH: 14
<212> TYPE: PRT
<213> ORGANISM: Macaca mulatta

<400> SEQUENCE: 125

Gln Val Trp Asp Ser Ser Ser Asp His Val Leu Phe Gly Gly
1               5                   10

<210> SEQ ID NO 126
<211> LENGTH: 10
<212> TYPE: PRT
<213> ORGANISM: Macaca mulatta

<400> SEQUENCE: 126

Gly Asp Asn Ile Gly Ser Lys Asn Val His
1               5                   10

<210> SEQ ID NO 127
<211> LENGTH: 7
<212> TYPE: PRT
<213> ORGANISM: Macaca mulatta

<400> SEQUENCE: 127

Ala Gly Thr Glu Arg Pro Ser
1               5

<210> SEQ ID NO 128
<211> LENGTH: 14
<212> TYPE: PRT
<213> ORGANISM: Macaca mulatta

<400> SEQUENCE: 128

Gln Val Trp Asp Gly Thr Arg Glu His Val Leu Phe Gly Gly
1               5                   10
```

```
<210> SEQ ID NO 129
<211> LENGTH: 12
<212> TYPE: PRT
<213> ORGANISM: Macaca mulatta

<400> SEQUENCE: 129

Gly Ser Ser Ser Asn Ile Arg Gly Asn Gly Val His
1               5                   10

<210> SEQ ID NO 130
<211> LENGTH: 7
<212> TYPE: PRT
<213> ORGANISM: Macaca mulatta

<400> SEQUENCE: 130

Asn Asn Asn Gln Arg Pro Ser
1               5

<210> SEQ ID NO 131
<211> LENGTH: 14
<212> TYPE: PRT
<213> ORGANISM: Macaca mulatta

<400> SEQUENCE: 131

Glu Ala Trp Asp Asn Ser Leu Ser Gly Gly Leu Phe Gly Gly
1               5                   10

<210> SEQ ID NO 132
<211> LENGTH: 12
<212> TYPE: PRT
<213> ORGANISM: Macaca mulatta

<400> SEQUENCE: 132

Gly Ser Ser Ser Asp Ile Gly Ser His Asp Val Tyr
1               5                   10

<210> SEQ ID NO 133
<211> LENGTH: 7
<212> TYPE: PRT
<213> ORGANISM: Macaca mulatta

<400> SEQUENCE: 133

Tyr Ser Asn Gln Arg Pro Ser
1               5

<210> SEQ ID NO 134
<211> LENGTH: 14
<212> TYPE: PRT
<213> ORGANISM: Macaca mulatta

<400> SEQUENCE: 134

Glu Thr Trp Glu Asn Ser Leu Ser Gly Pro Val Phe Gly Gly
1               5                   10

<210> SEQ ID NO 135
<211> LENGTH: 10
<212> TYPE: PRT
<213> ORGANISM: Macaca mulatta

<400> SEQUENCE: 135

Ala Ser Gln Ala Ile Ser Thr Tyr Leu Ala
1               5                   10

<210> SEQ ID NO 136
<211> LENGTH: 7
```

<212> TYPE: PRT
<213> ORGANISM: Macaca mulatta

<400> SEQUENCE: 136

Tyr Ala Thr Thr Leu His Thr
1               5

<210> SEQ ID NO 137
<211> LENGTH: 12
<212> TYPE: PRT
<213> ORGANISM: Macaca mulatta

<400> SEQUENCE: 137

Gln Gln Phe Lys Thr Leu Pro Tyr Thr Phe Gly Gln
1               5                   10

<210> SEQ ID NO 138
<211> LENGTH: 10
<212> TYPE: PRT
<213> ORGANISM: Macaca mulatta

<400> SEQUENCE: 138

Ala Ser Gln Asn Ile Tyr Ser Asn Leu Ala
1               5                   10

<210> SEQ ID NO 139
<211> LENGTH: 7
<212> TYPE: PRT
<213> ORGANISM: Macaca mulatta

<400> SEQUENCE: 139

Ala Ala Ser Ile Leu Gln Ser
1               5

<210> SEQ ID NO 140
<211> LENGTH: 12
<212> TYPE: PRT
<213> ORGANISM: Macaca mulatta

<400> SEQUENCE: 140

Gln Gln Gly Phe Gly Ile Pro Tyr Thr Phe Gly Gln
1               5                   10

<210> SEQ ID NO 141
<211> LENGTH: 13
<212> TYPE: PRT
<213> ORGANISM: Macaca mulatta

<400> SEQUENCE: 141

Gly Ser Asn Ser Asn Ile Gly Ala Gly Tyr Tyr Val Gln
1               5                   10

<210> SEQ ID NO 142
<211> LENGTH: 7
<212> TYPE: PRT
<213> ORGANISM: Macaca mulatta

<400> SEQUENCE: 142

Glu Asn Asn Lys Arg Pro Ser
1               5

<210> SEQ ID NO 143
<211> LENGTH: 14
<212> TYPE: PRT
<213> ORGANISM: Macaca mulatta

<400> SEQUENCE: 143

Gln Ser Tyr Asp Ser Ser Leu Ser Val Val Leu Phe Gly Gly
1               5                   10

<210> SEQ ID NO 144
<211> LENGTH: 10
<212> TYPE: PRT
<213> ORGANISM: Macaca mulatta

<400> SEQUENCE: 144

Gly Asp Asn Ile Gly Ser Lys Asn Val His
1               5                   10

<210> SEQ ID NO 145
<211> LENGTH: 7
<212> TYPE: PRT
<213> ORGANISM: Macaca mulatta

<400> SEQUENCE: 145

Ala Glu Thr Glu Arg Pro Ser
1               5

<210> SEQ ID NO 146
<211> LENGTH: 14
<212> TYPE: PRT
<213> ORGANISM: Macaca mulatta

<400> SEQUENCE: 146

Gln Val Trp Asp Gly Ser Ser Ala His Val Leu Phe Ala Gly
1               5                   10

<210> SEQ ID NO 147
<211> LENGTH: 10
<212> TYPE: PRT
<213> ORGANISM: Macaca mulatta

<400> SEQUENCE: 147

Gly Asp Asn Ile Gly Ser Lys Asn Val His
1               5                   10

<210> SEQ ID NO 148
<211> LENGTH: 7
<212> TYPE: PRT
<213> ORGANISM: Macaca mulatta

<400> SEQUENCE: 148

Ala Asp Ser Glu Arg Pro Ser
1               5

<210> SEQ ID NO 149
<211> LENGTH: 14
<212> TYPE: PRT
<213> ORGANISM: Macaca mulatta

<400> SEQUENCE: 149

Gln Val Trp Asp Ser Ser Ser Asn His Val Leu Phe Gly Gly
1               5                   10

<210> SEQ ID NO 150
<211> LENGTH: 10
<212> TYPE: PRT
<213> ORGANISM: Macaca mulatta

<400> SEQUENCE: 150

```
Ala Ser Gln Ser Val Ser Ser Trp Leu Ala
1               5                   10

<210> SEQ ID NO 151
<211> LENGTH: 7
<212> TYPE: PRT
<213> ORGANISM: Macaca mulatta

<400> SEQUENCE: 151

Lys Ala Ser Ser Leu Glu Gly
1               5

<210> SEQ ID NO 152
<211> LENGTH: 12
<212> TYPE: PRT
<213> ORGANISM: Macaca mulatta

<400> SEQUENCE: 152

Gln Gln Tyr Asn Ser Val Pro Tyr Ser Phe Gly His
1               5                   10
```

ANTIBODIES DIRECTED TO RICIN TOXIN

TECHNOLOGICAL FIELD

This invention generally relates to therapeutic antibodies for treating ricin toxin poisoning.

BACKGROUND ART

References considered to be relevant as background to the presently disclosed subject matter are listed below:
[1] Sandvig, K. and van Deurs, B. (1996) Physiol Rev 76:949-966
[2] U.S. Pat. No. 5,626,844
[3] U.S. Pat. No. 8,344,109
[4] U.S. Pat. No. 8,535,668
[5] WO 2012/167346
[6] Hu, W. G., et al. (2012) Plos One 7(9): e45595
[7] Luker, G. D., et al. (2003) Nature Med 9:969-973
[8] Gal Y., et al. Toxicol Rep. 2014; 1:496-504
[9] Pratt T S, et al. Exp Lung Res. 2007; 33:459-81
[10] Respaud R, et al. J Cont release. 2016; 234:21-32
[11] Gal Y, et al. J Immunol Methods. 2015; 424:136-9
[12] Cohen O, et al. Clin Vaccine Immunol 2014; 21:1534-40
[13] Sapoznikov A., et al. Toxins. 2015; 7:4817-31.
[14] Noy-Porat T, et al. Toxins. 2016; 8:64
[15] Griffiths G D, et al. Inhal Toxicol. 2007; 19:873-87.

Acknowledgement of the above references herein is not to be inferred as meaning that these are in any way relevant to the patentability of the presently disclosed subject matter.

BACKGROUND

Ricin is a toxic glycoprotein found in the seeds of *Ricinus communis* and is composed of two polypeptide chains, A and B, joined together by a disulfide bond. Ricin was shown to inhibit protein translation in vitro by damaging the ribosome and was named "Type II ribosome inactivating protein" (Type II RIP).

The B-chain of ricin (RTB) is approximately 33 kDa and is a galactose specific lectin that is responsible for binding ricin to glycoproteins or glycolipids on the surface of cells, facilitating the entry of ricin into the cytosol. The A chain of ricin (RTA), which is the catalytic subunit of ricin, is approximately 30 kDa in size and inhibits protein synthesis irreversibly by inactivating the 28S ribosomal subunit.

Ricin comprising both A and B chains (ricin "holotoxin") is enzymatically inactive and is activated only after reduction of the disulfide bond, which allows release of the catalytically active A chain into the cytoplasm (1).

Ricin is very poisonous if inhaled, injected, or ingested and is considered as a powerful agent of bioterrorism. Ricin toxicity varies according to its penetration route, where inhalation or injection of ricin toxin is more deleterious than ingestion thereof. After ingestion and inhalation, the clinical course typically progresses over 4-36 hours. In humans, the estimated lethal dose of inhaled ricin is in the range of 1 to 10 µg/kg.

Currently, there is no specific treatment for ricin poisoning. Following exposure to ricin, treatment is mainly supportive and may include administering analogues of sugar that prevent ricin binding to its target or inhibitors of the catalytic subunit, such as azidothymidine.

In addition, various antibodies directed against ricin toxin were developed (2-6, 14). However, reportedly when antibody-based treatment was initiated 24 hours post pulmonary ricin-exposure, only 30-60% of the intoxicated animals survived (8-10).

GENERAL DESCRIPTION

By one of its aspects the present invention provides an isolated monoclonal antibody or any antigen-binding fragment thereof which binds to ricin toxin, wherein said antibody is selected from a group consisting of:

a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125, or a variant thereof;

b. a monoclonal antibody comprising a CDRH1 denoted by SEQ ID NO. 96, CDRH2 denoted by SEQ ID NO. 97, CDRH3 denoted by SEQ ID NO. 98, and a CDRL1 denoted by SEQ ID NO. 126, a CDRL2 denoted by SEQ ID NO. 127, and a CDRL3 denoted by SEQ ID NO. 128, or a variant thereof;

c. a monoclonal antibody comprising the CDRH1 denoted by SEQ ID NO. 99, CDRH2 denoted by SEQ ID NO. 100, CDRH3 denoted by SEQ ID NO. 101, and a CDRL1 denoted by SEQ ID NO. 129, a CDRL2 denoted by SEQ ID NO. 130, and a CDRL3 denoted by SEQ ID NO. 131, or a variant thereof;

d. a monoclonal antibody comprising the CDRH1 denoted by SEQ ID NO. 102, CDRH2 denoted by SEQ ID NO. 103, CDRH3 denoted by SEQ ID NO. 104, and a CDRL1 denoted by SEQ ID NO. 132, a CDRL2 denoted by SEQ ID NO. 133, and a CDRL3 denoted by SEQ ID NO. 134, or a variant thereof;

e. a monoclonal antibody comprising the CDRH1 denoted by SEQ ID NO. 105, CDRH2 denoted by SEQ ID NO. 106, CDRH3 denoted by SEQ ID NO. 107, and a CDRL1 denoted by SEQ ID NO. 135, a CDRL2 denoted by SEQ ID NO. 136, and a CDRL3 denoted by SEQ ID NO. 137, or a variant thereof;

f. a monoclonal antibody comprising the CDRH1 denoted by SEQ ID NO. 108, CDRH2 denoted by SEQ ID NO. 109, CDRH3 denoted by SEQ ID NO. 110, and a CDRL1 denoted by SEQ ID NO. 138, a CDRL2 denoted by SEQ ID NO. 139, and a CDRL3 denoted by SEQ ID NO. 140, or a variant thereof;

g. a monoclonal antibody comprising the CDRH1 denoted by SEQ ID NO. 111, CDRH2 denoted by SEQ ID NO. 112, CDRH3 denoted by SEQ ID NO. 113, and a CDRL1 denoted by SEQ ID NO. 141, a CDRL2 denoted by SEQ ID NO. 142, and a CDRL3 denoted by SEQ ID NO. 143, or a variant thereof;

h. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146, or a variant thereof;

i. a monoclonal antibody comprising the CDRH1 denoted by SEQ ID NO. 117, CDRH2 denoted by SEQ ID NO. 118, CDRH3 denoted by SEQ ID NO. 119, and a CDRL1 denoted by SEQ ID NO. 147, a CDRL2 denoted by SEQ ID NO. 148, and a CDRL3 denoted by SEQ ID NO. 149, or a variant thereof; and j. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152, or a variant thereof.

By another one of its aspects the present invention provides an isolated monoclonal antibody or any antigen-binding fragment thereof which binds to ricin toxin, wherein said antibody comprises a heavy chain variable region and a light chain variable region, wherein said heavy chain variable region is encoded by a nucleic acid sequence which is at least 70% identical to the nucleic acid sequence denoted by SEQ ID NO. 60, SEQ ID NO. 61, SEQ ID NO. 62, SEQ ID NO. 53, SEQ ID NO. 54, SEQ ID NO. 55, SEQ ID NO. 56, SEQ ID NO. 57, SEQ ID NO. 58, or SEQ ID NO. 59 and wherein said light chain variable region is encoded by a nucleic acid sequence which is at least 70% identical to SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72.

In some embodiments the isolated monoclonal antibody according to the invention comprises a heavy chain variable region comprising the amino acid sequence denoted by SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82 or a variant thereof and a light chain variable region comprising the amino acid sequence denoted by SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, or a variant thereof.

In other embodiments the isolated monoclonal antibody according to the invention is selected from a group consisting of:
a. a monoclonal antibody comprising a heavy chain variable region comprising the amino acid sequence denoted by SEQ ID NO. 73 or a variant thereof and a light chain variable region comprising the amino acid sequence denoted by SEQ ID NO. 83 or a variant thereof;
b. a monoclonal antibody comprising a heavy chain variable region comprising the amino acid sequence denoted by SEQ ID NO. 74 or a variant thereof and a light chain variable region comprising the amino acid sequence denoted by SEQ ID NO. 84 or a variant thereof;
c. a monoclonal antibody comprising a heavy chain variable region comprising the amino acid sequence denoted by SEQ ID NO. 75 or a variant thereof and a light chain variable region comprising the amino acid sequence denoted by SEQ ID NO. 85 or a variant thereof;
d. a monoclonal antibody comprising a heavy chain variable region comprising the amino acid sequence denoted by SEQ ID NO. 76 or a variant thereof and a light chain variable region comprising the amino acid sequence denoted by SEQ ID NO. 86 or a variant thereof;
e. a monoclonal antibody comprising a heavy chain variable region comprising the amino acid sequence denoted by SEQ ID NO. 77 or a variant thereof and a light chain variable region comprising the amino acid sequence denoted by SEQ ID NO. 87 or a variant thereof;
f. a monoclonal antibody comprising a heavy chain variable region comprising the amino acid sequence denoted by SEQ ID NO. 78 or a variant thereof and a light chain variable region comprising the amino acid sequence denoted by SEQ ID NO. 88 or a variant thereof;
g. a monoclonal antibody comprising a heavy chain variable region comprising the amino acid sequence denoted by SEQ ID NO. 79 or a variant thereof and a light chain variable region comprising the amino acid sequence denoted by SEQ ID NO. 89 or a variant thereof;
h. a monoclonal antibody comprising a heavy chain variable region comprising the amino acid sequence denoted by SEQ ID NO. 80 or a variant thereof and a light chain variable region comprising the amino acid sequence denoted by SEQ ID NO. 90 or a variant thereof;
i. a monoclonal antibody comprising a heavy chain variable region comprising the amino acid sequence denoted by SEQ ID NO. 81 or a variant thereof and a light chain variable region comprising the amino acid sequence denoted by SEQ ID NO. 91 or a variant thereof; and
j. a monoclonal antibody comprising a heavy chain variable region comprising the amino acid sequence denoted by SEQ ID NO. 82 or a variant thereof and a light chain variable region comprising the amino acid sequence denoted by SEQ ID NO. 92 or a variant thereof.

In further embodiments the isolated monoclonal antibody according to the invention binds to ricin A chain.

In specific embodiments the isolated monoclonal antibody according to the invention comprises a heavy chain variable region comprising the amino acid sequence denoted by SEQ ID NO. 73, SEQ ID NO. 75, SEQ ID NO. 76, SEQ ID NO. 77 or SEQ ID NO. 79 and a light chain variable region denoted by SEQ ID NO. 83, SEQ ID NO. 85, SEQ ID NO. 86, SEQ ID NO. 87 or SEQ ID NO. 89.

In still further embodiments the isolated monoclonal antibody according to the invention binds to ricin B chain.

In further specific embodiments the isolated monoclonal antibody according to the invention comprises a heavy chain variable region comprising the amino acid sequence denoted by SEQ ID NO. 74, SEQ ID NO. 78, SEQ ID NO. 80, SEQ ID NO. 81 or SEQ ID NO. 82 and a light chain variable region denoted by SEQ ID NO. 84, SEQ ID NO. 88, SEQ ID NO. 90, SEQ ID NO. 91 or SEQ ID NO. 92.

In further specific embodiments the isolated monoclonal antibody according to the invention is a highly neutralizing anti ricin antibody selected from the group consisting of:
a. the monoclonal antibody denoted MH1 comprising a heavy chain variable region comprising the amino acid sequence denoted by SEQ ID NO. 73 and a light chain variable region denoted by SEQ ID NO. 83;
b. the monoclonal antibody denoted MH36 comprising a heavy chain variable region comprising the amino acid sequence denoted by SEQ ID NO. 75 and a light chain variable region denoted by SEQ ID NO. 85;
c. the monoclonal antibody denoted MH75 comprising a heavy chain variable region comprising the amino acid sequence denoted by SEQ ID NO. 80 and a light chain variable region denoted by SEQ ID NO. 90; and
d. the monoclonal antibody denoted MH77 comprising a heavy chain variable region comprising the amino acid sequence denoted by SEQ ID NO. 82 and a light chain variable region denoted by SEQ ID NO. 92.

In some embodiments the isolated monoclonal antibody as herein defined is a chimeric, a humanized or a human antibody. In other embodiments, the isolated monoclonal antibody as herein defined is a chimeric antibody.

In other embodiments the isolated monoclonal antibody according to the invention is an antibody fragment selected from the group consisting of Fv, single chain Fv (scFv), heavy chain variable region, light chain variable region, Fab, F(ab)₂' and any combination thereof.

In further embodiments the isolated monoclonal antibody as herein defined is a neutralizing antibody.

By another one of its aspects the present invention provides a bispecific molecule comprising the antibody as herein defined.

By yet another one of its aspects the present invention provides an isolated nucleic acid molecule comprising a nucleotide sequence encoding an antibody or any antigen-binding fragment thereof according to the invention.

The present invention further provides an expression vector comprising the isolated nucleic acid molecule according to the invention and a host cell transfected with said isolated nucleic acid molecule or with the expression vector as herein defined.

By yet another one of its aspects the present invention provides an immunoconjugate comprising the antibody or any antigen-binding fragment thereof as herein defined and an additional anti-ricin agent.

In some embodiments the additional anti-ricin agent is selected from the group consisting of a sugar analogue, an inhibitor of the catalytic subunit of ricin toxin and an additional antibody.

By still another one of its aspects the present invention provides a pharmaceutical composition comprising as an active ingredient the isolated monoclonal antibody or any antigen-binding fragment thereof, the bispecific molecule or the immunoconjugate according to the invention and a pharmaceutically acceptable carrier, excipient or diluent.

In some embodiments the pharmaceutical composition according to the invention further comprises an adjuvant and/or an additional anti-ricin agent.

By yet another one of its aspects, the present invention provides the isolated monoclonal antibody or any antigen-binding fragment thereof, the bispecific molecule, the immunoconjugate or the pharmaceutical composition according to the invention for use in a method of prophylaxis, treatment or amelioration of ricin toxin poisoning.

The present invention further provides a method of prophylaxis, treatment or amelioration of ricin toxin poisoning comprising administering to a subject in need thereof a therapeutically effective amount of the isolated monoclonal antibody or any antigen-binding fragment thereof, the bispecific molecule, the immunoconjugate or the pharmaceutical composition according to the invention.

In some embodiments the method of prophylaxis, treatment or amelioration of ricin toxin poisoning as herein defined further comprises administering to a subject in need thereof an additional anti-ricin agent.

In the above and other embodiments the isolated monoclonal antibody or any antigen-binding fragment thereof, bispecific molecule, immunoconjugate or pharmaceutical composition is administered to said subject prior to or after exposure to ricin toxin.

In some embodiments the isolated monoclonal antibody or any antigen-binding fragment thereof, bispecific molecule, immunoconjugate or pharmaceutical composition according to the invention is administered to said subject immediately after exposure to ricin toxin or between about 1 to about 96 hours after exposure to ricin toxin.

In other embodiments the antibody as herein defined is administered at a therapeutically effective amount. The treating physician would be able to determine the appropriate therapeutic dosage depending on various clinical parameters of the patient as is well known in the art. A therapeutically effective amount of the antibody is for example between about 10 µg/kg to about 50 mg/kg. Non-limiting examples of dosage forms include 1 mg/kg, 2 mg/kg, 3 mg/kg, 3.3 mg/kg, 5 mg/kg, 10 mg/kg, 20 mg/kg, 30 mg/kg, 40 mg/kg and 50 mg/kg.

In further embodiments the isolated monoclonal antibody or any antigen-binding fragment thereof, bispecific molecule, immunoconjugate or pharmaceutical composition as herein defined is administered to said subject as a single dose or as multiple doses.

The present invention further provides a method of neutralizing ricin poisoning comprising administering to a subject in need thereof a therapeutically effective amount of the isolated monoclonal antibody or any antigen-binding fragment thereof, the bispecific molecule, the immunoconjugate or the pharmaceutical composition according to the invention.

By still another one of its aspects the present invention provides a method of detecting ricin toxin in a biological sample obtained from a subject, said method comprising:
  (a) contacting said biological sample with the isolated monoclonal antibody or any antigen-binding fragment thereof according to the invention, wherein said monoclonal antibody is labeled with a detectable marker; and
  (b) detecting said isolated monoclonal antibody or any antigen-binding fragment thereof;
  wherein the presence of said isolated monoclonal antibody or any antigen-binding fragment thereof indicates the presence of ricin toxin in said biological sample.

The present invention further provides a kit for detecting ricin toxin comprising:
  (c) at least one labeled isolated monoclonal antibody or any antigen-binding fragment thereof according to the invention;
  (d) means for detection of said labeled isolated monoclonal antibody; and optionally
  (e) instructions for use of said kit.

In another aspect, the present invention provides a pharmaceutical composition comprising as an active ingredient a combination of at least two isolated monoclonal antibodies or any antigen-binding fragment thereof which bind to ricin toxin, and a pharmaceutically acceptable carrier, excipient or diluent, wherein said antibodies are selected from the group consisting of:
  a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125, or a variant thereof;
  b. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146, or a variant thereof; and
  c. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152, or a variant thereof.

In another aspect, the present invention provides a pharmaceutical composition comprising as an active ingredient a combination of at least two isolated monoclonal antibodies or any antigen-binding fragment thereof which bind to ricin toxin, and a pharmaceutically acceptable carrier, excipient or diluent, wherein said isolated monoclonal antibodies comprise a heavy chain variable region and a light chain variable region, wherein said heavy chain variable region is encoded by a nucleic acid sequence which is at least 70% identical to a nucleic acid sequence selected from the group consisting of SEQ ID NO. 60, SEQ ID NO. 57, or SEQ ID NO. 59 and wherein said light chain variable region is encoded by a nucleic acid sequence which is at least 70% identical to a nucleic acid sequence selected from the group consisting of SEQ ID NO. 63, SEQ ID NO. 70, or SEQ ID NO. 72.

In one embodiment, said isolated monoclonal antibodies comprise a heavy chain variable region selected from the group consisting of the amino acid sequences denoted by SEQ ID NO. 73, SEQ ID NO. 80, SEQ ID NO. 82 or a variant thereof and a light chain variable region selected from the group consisting of the amino acid sequences denoted by SEQ ID NO. 83, SEQ ID NO. 90, SEQ ID NO. 92, or a variant thereof.

In one embodiment, said isolated monoclonal antibodies are selected from a group consisting of:
a. a monoclonal antibody comprising a heavy chain variable region comprising the amino acid sequence denoted by SEQ ID NO. 73 or a variant thereof and a light chain variable region comprising the amino acid sequence denoted by SEQ ID NO. 83, denoted MH1, or a variant thereof;
b. a monoclonal antibody comprising a heavy chain variable region comprising the amino acid sequence denoted by SEQ ID NO. 80 or a variant thereof and a light chain variable region comprising the amino acid sequence denoted by SEQ ID NO. 90, denoted MH75, or a variant thereof; and
c. a monoclonal antibody comprising a heavy chain variable region comprising the amino acid sequence denoted by SEQ ID NO. 82 or a variant thereof and a light chain variable region comprising the amino acid sequence denoted by SEQ ID NO. 92, denoted MH77, or a variant thereof.

In a specific embodiment, said composition comprises the isolated monoclonal antibodies denoted MH1, MH75 and MH77 and a pharmaceutically acceptable carrier, excipient or diluent.

In another specific embodiment, said composition consists of the isolated monoclonal antibodies denoted MH1, MH75 and MH77 and a pharmaceutically acceptable carrier, excipient or diluent.

In one embodiment, said isolated monoclonal antibodies are chimeric, humanized or human antibodies.

In one embodiment, said isolated monoclonal antibodies are chimeric antibodies.

In one embodiment, said isolated monoclonal antibodies are antibody fragments selected from the group consisting of Fv, single chain Fv (scFv), heavy chain variable region, light chain variable region, Fab, F(ab)$_2$' and any combination thereof.

In one embodiment, said isolated monoclonal antibodies are neutralizing antibodies.

In one embodiment, said composition further comprising an adjuvant.

In one embodiment, said composition further comprises an additional anti-ricin agent.

In another aspect, the present invention provides a method of prophylaxis, treatment or amelioration of ricin toxin poisoning comprising administering to a subject in need thereof a therapeutically effective amount of the pharmaceutical composition of the invention.

In one embodiment, said method further comprises administering to a subject in need thereof an additional anti-ricin agent.

In one embodiment, said pharmaceutical composition is administered to said subject prior to or after exposure to ricin toxin.

In one embodiment, said pharmaceutical composition is administered to said subject immediately after exposure to ricin toxin or between about 1 to about 96 hours after exposure to ricin toxin.

In one embodiment, said isolated monoclonal antibodies in the pharmaceutical composition are administered at a therapeutically effective amount of 10-50,000 µg/kg.

In one embodiment, said pharmaceutical composition is administered to said subject as a single dose or as multiple doses.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 Multiple Alignment of the heavy chain nucleic acid sequences of the antibodies MH1, MH2, MH36, MH49, MH67, MH73, MH74, MH75, MH76, and MH77. Nucleic acid sequences of the heavy chains of the indicated antibodies are shown as a multiple alignment.

FIG. 2 Multiple Alignment of the light chain nucleic acid sequences of the antibodies MH1, MH2, MH36, MH49, MH67, MH73, MH74, MH75, MH76, and MH77. Nucleic acid sequences of the light chains of the indicated antibodies are shown as a multiple alignment.

FIG. 3 Amino acid sequences of the heavy chain variable domains of the antibodies MH1, MH2, MH36, MH49, MH67, MH73, MH74, MH75, MH76, and MH77 Amino acid sequences of the heavy chains of the indicated antibodies are shown as a multiple alignment. The complementarity determining regions (CDRs) are shown in grey boxes.

FIG. 4 Amino acid sequences of the light chain variable domains of the antibodies MH1, MH2, MH36, MH49, MH67, MH73, MH74, MH75, MH76, and MH77 Amino acid sequences of the light chains of the indicated antibodies are shown as a multiple alignment. The CDRs are shown in grey boxes.

FIGS. 5A and 5B Screening the binding activity of antibodies MH1, MH2, MH36, MH49, MH67, MH73, MH74, MH75, MH76, and MH77 to Ricin. FIG. 5A shows a bar graph showing the binding of the indicated antibodies to Ricin, Ricin A chain (RTA) and Ricin B chain (RTB), using an ELISA assay. FIG. 5B shows a graph showing the binding of antibody MH73 to Ricin, RTA and RTB, using Biolayer Interferometry. Abbreviations: RTA, Ricin A chain; RTB, Ricin B chain; O.D., optical density.

FIGS. 9A, 9B and 9C Epitope binning. The ability of anti-ricin antibodies to bind the toxin, simultaneously, was evaluated using the Octet Red system. Following immobilization of the first antibody (A) MH1, (B) MH77 or (C) MH73, ricin was loaded and following a short wash the complex was immersed in a well containing the indicated antibody (indicated by the dashed line), washed again and immersed with the next antibody as indicated.

DETAILED DESCRIPTION OF EMBODIMENTS

Figure 6:
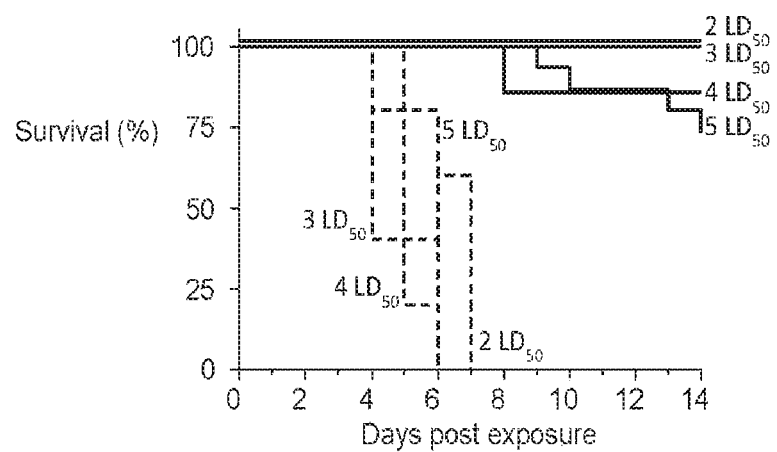
FIG. 6 Post-exposure treatment of ricin-intoxicated mice. Mice were intra-nasally instilled with the indicated doses of ricin. Six hours later, the ricin-intoxicated mice were either treated by intravenous administration of the four antibody cocktail (solid lines, n=10 for 2LD$_{50}$, n=5 for 3LD$_{50}$, n=7 for 4 LD$_{50}$, and n=15 for 5LD$_{50}$) or left untreated (dashed lines, n=5 for each ricin dose). Animal survival was monitored for 14 days.

The present disclosure is based on the preparation of monoclonal antibodies directed against the ricin toxin that are able to neutralize the activity of the toxin, as described below and demonstrated in the Examples.

Therefore the present disclosure provides an isolated monoclonal antibody or any antigen-binding fragment thereof which binds to ricin toxin, wherein said antibody is selected from a group consisting of:
  a. a monoclonal antibody, comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125, or a variant thereof;
  b. a monoclonal antibody comprising a CDRH1 denoted by SEQ ID NO. 96, CDRH2 denoted by SEQ ID NO. 97, CDRH3 denoted by SEQ ID NO. 98, and a CDRL1 denoted by SEQ ID NO. 126, a CDRL2 denoted by SEQ ID NO. 127, and a CDRL3 denoted by SEQ ID NO. 128, or a variant thereof;
  c. a monoclonal antibody comprising the CDRH1 denoted by SEQ ID NO. 99, CDRH2 denoted by SEQ ID NO. 100, CDRH3 denoted by SEQ ID NO. 101, and a CDRL1 denoted by SEQ ID NO. 129, a CDRL2 denoted by SEQ ID NO. 130, and a CDRL3 denoted by SEQ ID NO. 131, or a variant thereof;
  d. a monoclonal antibody comprising the CDRH1 denoted by SEQ ID NO. 102, CDRH2 denoted by SEQ ID NO. 103, CDRH3 denoted by SEQ ID NO. 104, and a CDRL1 denoted by SEQ ID NO. 132, a CDRL2 denoted by SEQ ID NO. 133, and a CDRL3 denoted by SEQ ID NO. 134, or a variant thereof;
  e. a monoclonal antibody comprising the CDRH1 denoted by SEQ ID NO. 105, CDRH2 denoted by SEQ ID NO. 106, CDRH3 denoted by SEQ ID NO. 107, and a CDRL1 denoted by SEQ ID NO. 135, a CDRL2 denoted by SEQ ID NO. 136, and a CDRL3 denoted by SEQ ID NO. 137, or a variant thereof;
  f. a monoclonal antibody comprising the CDRH1 denoted by SEQ ID NO. 108, CDRH2 denoted by SEQ ID NO. 109, CDRH3 denoted by SEQ ID NO. 110, and a CDRL1 denoted by SEQ ID NO. 138, a CDRL2 denoted by SEQ ID NO. 139, and a CDRL3 denoted by SEQ ID NO. 140, or a variant thereof;
  g. a monoclonal antibody comprising the CDRH1 denoted by SEQ ID NO. 111, CDRH2 denoted by SEQ ID NO. 112, CDRH3 denoted by SEQ ID NO. 113, and a CDRL1 denoted by SEQ ID NO. 141, a CDRL2 denoted by SEQ ID NO. 142, and a CDRL3 denoted by SEQ ID NO. 143, or a variant thereof;
  h. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146, or a variant thereof;
  i. a monoclonal antibody comprising the CDRH1 denoted by SEQ ID NO. 117, CDRH2 denoted by SEQ ID NO. 118, CDRH3 denoted by SEQ ID NO. 119, and a CDRL1 denoted by SEQ ID NO. 147, a CDRL2 denoted by SEQ ID NO. 148, and a CDRL3 denoted by SEQ ID NO. 149, or a variant thereof; and
  j. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152, or a variant thereof.

The term "ricin toxin" refers to a glycoprotein found in the seeds of *Ricinus communis* (*R. communis*, also known as castor oil plant). These seeds are also referred to herein as "castor beans". Ricin toxin is composed of two polypeptide chains, A and B, joined together by a disulfide bond. The ricin toxin may be prepared using any method known in the art, for example by extraction from seeds of *R. communis*, as described in the Examples below.

As indicated above, the present invention provides isolated monoclonal antibodies that bind to ricin toxin. The term "antibody" refers to a polypeptide encoded by an immunoglobulin gene or functional fragments thereof that specifically binds and recognizes an antigen, namely ricin toxin.

The term "monoclonal antibody", "monoclonal antibodies" or "mAb" as herein defined refers to a population of substantially homogenous antibodies, i.e., the individual antibodies comprising the population are identical except for possibly naturally occurring mutations that may be present in minor amounts. Monoclonal antibodies are directed against a single antigenic site (epitope).

Monoclonal antibodies may be prepared and purified by any method known in the art. For example, monoclonal antibodies may be prepared from B cells taken from the spleen or lymph nodes of immunized animals (e.g. rats, mice or monkeys), by fusion with immortalized B cells under conditions which favor the growth of hybrid cells.

Immunization of animals may be carried out by any method known in the art, for example by immunizing monkeys, as described below. The immunized monkeys are then sacrificed and samples are taken from their blood and lymphatic nodes in order to isolate mRNA that will be used for variable heavy and variable light (VH/VL) chain amplification and further used for example for constructing a phage display library, in order to select active antibodies. Based on the results obtained from a phage display library, full length antibodies are produced, as known in the art and as described below.

Purification of monoclonal antibodies may be performed using any method known in the art, for example by affinity chromatography, namely, by using an affinity column to which a specific epitope (or antigen) is conjugated. Alternatively purification of antibodies may be based on using protein A column chromatography, as described below.

An exemplary antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition.

Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarity determining regions", or "CDRs", the CDRs are positioned either at the heavy chain of the antibody ("a heavy chain complementarity determining region") or at the light chain of the antibody (a "light chain complementarity determining region").

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, the complementarity determining regions CDRH1, CDRH2 and CDRH3 refer to the three complementarity determining regions starting from the N-terminus of the antibody's heavy chain (also referred to herein as heavy chain complementarity determining region) and the complementarity determining regions CDRL1, CDRL2 and CDRL3 refer to the three complementarity determining regions starting from the N-terminus of the antibody's light chain (also referred to herein as light chain complementarity determining region).

For example, as demonstrated in FIG. 3 in the context of the heavy chain of the antibody referred to herein as "MH1", CDRH1, CDRH2 and CDRH3 appear as grey boxes in the amino acid sequence of the heavy chain of the antibody. The respective CDRL1, CDRL2 and CDRL3 of the antibody referred to herein as MH1, appear in FIG. 4 in the context of the light chain of the antibody.

Binding of antibodies or antigen-binding fragments thereof to ricin toxin may be determined using any method known in the art, for example using an ELISA assay as described below or BIAcore analysis.

In some embodiments the isolated monoclonal antibody according to the invention comprises the CDRH1 denoted by SEQ ID NO. 93, CDRH2 denoted by SEQ ID NO. 94, and CDRH3 denoted by SEQ ID NO. 95, and the CDRL1 denoted by SEQ ID NO. 123, CDRL2 denoted by SEQ ID NO. 124, and the CDRL3 denoted by SEQ ID NO. 125, or a variant thereof.

In other embodiments the isolated monoclonal antibody as herein defined comprises the CDRH1 denoted by SEQ ID NO. 96, CDRH2 denoted by SEQ ID NO. 97, and the CDRH3 denoted by SEQ ID NO. 98, and the CDRL1 denoted by SEQ ID NO. 126, CDRL2 denoted by SEQ ID NO. 127, and the CDRL3 denoted by SEQ ID NO. 128, or a variant thereof.

In further embodiments the isolated monoclonal antibody as herein defined comprises the CDRH1 denoted by SEQ ID NO. 99, CDRH2 denoted by SEQ ID NO. 100, and the CDRH3 denoted by SEQ ID NO. 101, and the CDRL1 denoted by SEQ ID NO. 129, CDRL2 denoted by SEQ ID NO. 130, and the CDRL3 denoted by SEQ ID NO. 131, or a variant thereof.

In still further embodiments the isolated monoclonal antibody as herein defined comprises the CDRH1 denoted by SEQ ID NO. 102, CDRH2 denoted by SEQ ID NO. 103, and the CDRH3 denoted by SEQ ID NO. 104, and the CDRL1 denoted by SEQ ID NO. 132, CDRL2 denoted by SEQ ID NO. 133, and the CDRL3 denoted by SEQ ID NO. 134, or a variant thereof.

In some embodiments the isolated monoclonal antibody as herein defined comprises the CDRH1 denoted by SEQ ID NO. 105, CDRH2 denoted by SEQ ID NO. 106, and the CDRH3 denoted by SEQ ID NO. 107, and the CDRL1 denoted by SEQ ID NO. 135, CDRL2 denoted by SEQ ID NO. 136, and the CDRL3 denoted by SEQ ID NO. 137, or a variant thereof.

In other embodiments the isolated monoclonal antibody as herein defined comprises the CDRH1 denoted by SEQ ID NO. 108, CDRH2 denoted by SEQ ID NO. 109, and the CDRH3 denoted by SEQ ID NO. 110, and the CDRL1 denoted by SEQ ID NO. 138, CDRL2 denoted by SEQ ID NO. 139, and the CDRL3 denoted by SEQ ID NO. 140, or a variant thereof.

In further embodiments the isolated monoclonal antibody according to the invention comprises the CDRH1 denoted by SEQ ID NO. 111, CDRH2 denoted by SEQ ID NO. 112, and the CDRH3 denoted by SEQ ID NO. 113, and the CDRL1 denoted by SEQ ID NO. 141, CDRL2 denoted by SEQ ID NO. 142, and the CDRL3 denoted by SEQ ID NO. 143, or a variant thereof.

In still further embodiments the isolated monoclonal antibody as herein defined comprises the CDRH1 denoted by SEQ ID NO. 114, CDRH2 denoted by SEQ ID NO. 115, and the CDRH3 denoted by SEQ ID NO. 116, and the CDRL1 denoted by SEQ ID NO. 144, CDRL2 denoted by SEQ ID NO. 145, and the CDRL3 denoted by SEQ ID NO. 146, or a variant thereof.

In yet further embodiments the isolated monoclonal antibody as herein defined comprises the CDRH1 denoted by SEQ ID NO. 117, CDRH2 denoted by SEQ ID NO. 118, and the CDRH3 denoted by SEQ ID NO. 119, and the CDRL1 denoted by SEQ ID NO. 147, CDRL2 denoted by SEQ ID NO. 148, and the CDRL3 denoted by SEQ ID NO. 149, or a variant thereof.

In some embodiments the isolated monoclonal antibody as herein defined comprises the CDRH1 denoted by SEQ ID NO. 120, CDRH2 denoted by SEQ ID NO. 121, and the CDRH3 denoted by SEQ ID NO. 122, and the CDRL1 denoted by SEQ ID NO. 150, CDRL2 denoted by SEQ ID NO. 151, and the CDRL3 denoted by SEQ ID NO. 152, or a variant thereof.

The CDRs of the antibodies referred to herein are presented in Table 4 as well as in the context of their respective heavy and light chain sequences, e.g. in FIG. 3 and in FIG. 4, respectively.

By the term "variant" it is meant sequences of amino acids or nucleotides that are different from the sequences specifically identified herein, namely, in which one or more amino acid residues or nucleotides are deleted, substituted or added.

It should be appreciated that by the term "added", as used herein it is meant any addition(s) of amino acid residues to the sequences described herein. For example, the variant antibodies of the invention may be extended at their N-terminus and/or C-terminus with various identical or different amino acid residues.

Variants also encompass various amino acid substitutions. An amino acid "substitution" is the result of replacing one amino acid with another amino acid which has similar or different structural and/or chemical properties Amino acid substitutions may be made on the basis of similarity in polarity, charge, solubility, hydrophobicity, hydrophilicity, and/or the amphipathic nature of the residues involved.

Variants further encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences, respectively, with the amino acid or nucleotide sequences described herein (namely the amino acid or nucleotide sequences of the heavy and light chains of the antibodies herein described).

Therefore in some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

In some embodiments the isolated monoclonal antibody or any antigen-binding fragment thereof according to the invention is wherein said antibody comprises a heavy chain variable region and a light chain variable region, wherein said heavy chain variable region is encoded by a nucleic acid sequence which is at least 70% identical to the nucleic acid sequence denoted by SEQ ID NO. 60, SEQ ID NO. 61, SEQ ID NO. 62, SEQ ID NO. 53, SEQ ID NO. 54, SEQ ID NO. 55, SEQ ID NO. 56, SEQ ID NO. 57, SEQ ID NO. 58, or SEQ ID NO. 59 and wherein said light chain variable region is encoded by a nucleic acid sequence which is at least 70% identical to SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 60 and wherein the light chain variable region of the antibody is encoded by a nucleic acid sequence which is at least 70% identical to SEQ ID NO. 63.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 61 and wherein the light chain variable region of the antibody is encoded by a nucleic acid sequence which is at least 70% identical to SEQ ID NO. 64.

In still further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 62 and wherein the light chain variable region of the antibody is encoded by a nucleic acid sequence which is at least 70% identical to SEQ ID NO. 65.

In some embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 53 and wherein the light chain variable region of the antibody is encoded by a nucleic acid sequence which is at least 70% identical to SEQ ID NO. 66.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 54 and wherein the light chain variable region of the antibody is encoded by a nucleic acid sequence which is at least 70% identical to SEQ ID NO. 67.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 55 and wherein the light chain variable region of the antibody is encoded by a nucleic acid sequence which is at least 70% identical to SEQ ID NO. 68.

In still further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 56 and wherein the light chain variable region of the antibody is encoded by a nucleic acid sequence which is at least 70% identical to SEQ ID NO. 69.

In some embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 57 and wherein the light chain variable region of the antibody is encoded by a nucleic acid sequence which is at least 70% identical to SEQ ID NO. 70.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 58 and wherein the light chain variable region of the antibody is encoded by a nucleic acid sequence which is at least 70% identical to SEQ ID NO. 71.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 59 and wherein the light chain variable region of the antibody is encoded by a nucleic acid sequence which is at least 70% identical to SEQ ID NO. 72.

In further embodiments the isolated monoclonal antibody according to the invention is wherein said antibody comprises a heavy chain variable region comprising the amino acid sequence denoted by SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82 or a variant thereof and a light chain variable region comprising the amino acid sequence denoted by SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, or a variant thereof.

In specific embodiments the isolated monoclonal antibody according to the invention comprises a heavy chain variable region comprising the amino acid sequence denoted by SEQ ID NO. 73 or a variant thereof and a light chain variable region comprising the amino acid sequence denoted by SEQ ID NO. 83, or a variant thereof.

In other embodiments the isolated monoclonal antibody according to the invention comprises a heavy chain variable region comprising the amino acid sequence denoted by SEQ ID NO. 74 or a variant thereof and a light chain variable region comprising the amino acid sequence denoted by SEQ ID NO. 84, or a variant thereof.

In further embodiments the isolated monoclonal antibody according to the invention comprises a heavy chain variable region comprising the amino acid sequence denoted by SEQ ID NO. 75 or a variant thereof and a light chain variable region comprising the amino acid sequence denoted by SEQ ID NO. 85, or a variant thereof.

In still further embodiments the isolated monoclonal antibody according to the invention comprises a heavy chain variable region comprising the amino acid sequence denoted by SEQ ID NO. 76 or a variant thereof and a light chain variable region comprising the amino acid sequence denoted by SEQ ID NO. 86, or a variant thereof.

In some embodiments the isolated monoclonal antibody according to the invention comprises a heavy chain variable region comprising the amino acid sequence denoted by SEQ ID NO. 77 or a variant thereof and a light chain variable region comprising the amino acid sequence denoted by SEQ ID NO. 87, or a variant thereof.

In other embodiments the isolated monoclonal antibody according to the invention comprises a heavy chain variable region comprising the amino acid sequence denoted by SEQ ID NO. 78 or a variant thereof and a light chain variable region comprising the amino acid sequence denoted by SEQ ID NO. 88, or a variant thereof.

In further embodiments the isolated monoclonal antibody according to the invention comprises a heavy chain variable region comprising the amino acid sequence denoted by SEQ ID NO. 79 or a variant thereof and a light chain variable region comprising the amino acid sequence denoted by SEQ ID NO. 89, or a variant thereof.

In still further embodiments the isolated monoclonal antibody according to the invention comprises a heavy chain variable region comprising the amino acid sequence denoted by SEQ ID NO. 80 or a variant thereof and a light chain variable region comprising the amino acid sequence denoted by SEQ ID NO. 90, or a variant thereof.

In yet further embodiments the isolated monoclonal antibody according to the invention comprises a heavy chain variable region comprising the amino acid sequence denoted by SEQ ID NO. 81 or a variant thereof and a light chain variable region comprising the amino acid sequence denoted by SEQ ID NO. 91, or a variant thereof.

In some specific embodiments the isolated monoclonal antibody according to the invention comprises a heavy chain variable region comprising the amino acid sequence denoted by SEQ ID NO. 82 or a variant thereof and a light chain variable region comprising the amino acid sequence denoted by SEQ ID NO. 92, or a variant thereof.

Figures 5A, 5B:
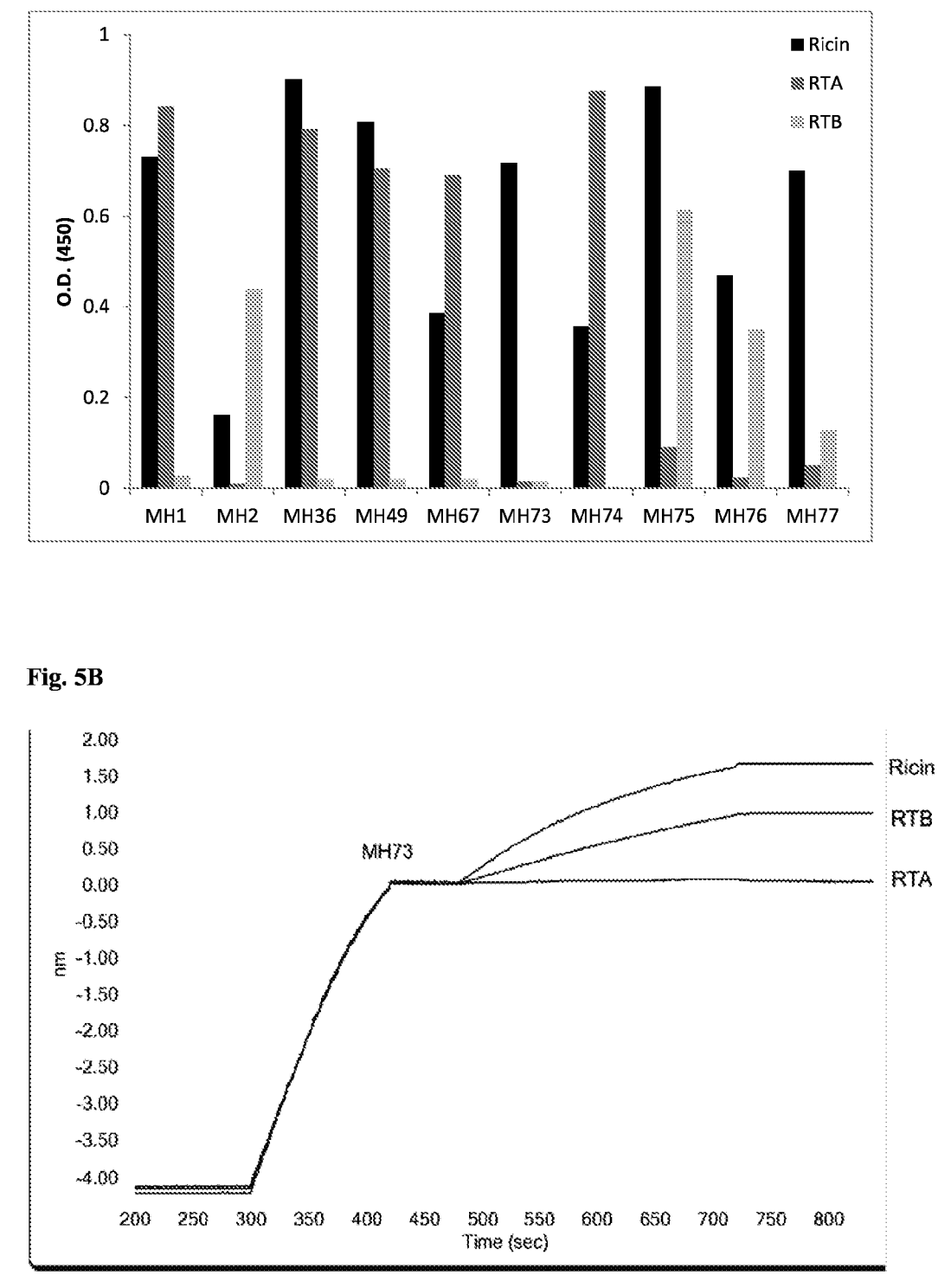

As demonstrated in FIG. 5, all of the monoclonal antibodies prepared as described herein showed high binding affinity to ricin toxin, five of which (namely the antibodies referred to herein as MH1, MH36, MH49, MH67 and MH74) were shown to bind the RTA subunit; five of which (namely the antibodies referred to herein as MH2, MH75, MH76 and MH77 and MH73) were shown to bind the RTB subunit.

As demonstrated in Example 4, antibodies of the invention exhibited a substantial efficacy with regard to protection from ricin intoxication, further resulting in very high percentages of mice survival after ricin intoxication (83% to 100% survival). Therefore, in a specific embodiment the invention provides an isolated monoclonal antibody or any antigen-binding fragment thereof which binds to ricin toxin, wherein administration of said antibody results in significant protection of the infected subjects against ricin intoxication. The protective effect can be measured for example in animal models of ricin intoxication as shown in Example 4 below. Significant protection is understood as survival of at least about 80%, or at least about 83%, or at least about 85%, or at least about 90% of infected animals. It should be noted that administration of certain antibodies results in between 95% and 100% survival of infected animals (namely, 95%, 96%, 97%, 98%, 99% or 100% survival of the animals).

Specifically, the antibodies designated MH73, MH36, MH75, MH1 and MH77 showed significant protection of infected mice against ricin intoxication in an in vivo protection model. All these antibodies showed protection percentage higher than 83%. More specifically, each of the antibodies MH36, MH75, MH1 and MH77 showed protection percentage higher than 95%.

Therefore, in a specific embodiment, the present invention provides an isolated monoclonal antibody or any antigen-binding fragment thereof which binds to ricin toxin, selected from the group consisting of the antibodies designated MH73, MH36, MH75, MH1 and MH77. In another specific embodiment, the present invention provides an isolated monoclonal antibody or any antigen-binding fragment thereof which binds to ricin toxin, selected from the group consisting of the antibodies designated MH36, MH75, MH1 and MH77. The amino acid sequences of the heavy chain variable region and the light chain variable region of each of these antibodies are specified below.

As indicated above, the ricin toxin is composed of two polypeptide chains, A and B, joined together by a disulfide bond.

Therefore the term "ricin A chain" as used herein and as known in the art, refers to the A chain of ricin (RTA), which is the catalytic subunit of the glycoprotein. RTA is approximately 30 kDa in size. In some embodiments RTA may be prepared for example by extracting the toxin from seeds of *R. communis* and subjecting the obtained extract to reducing conditions and further separation steps, thereby separating the A chain from the B chain, as described for example below.

Therefore in some embodiments the isolated monoclonal antibody according to the invention binds to ricin A chain.

In specific embodiments the isolated monoclonal antibody as herein defined comprises a heavy chain variable region comprising the amino acid sequence denoted by SEQ ID NO. 73, SEQ ID NO. 75, SEQ ID NO. 76, SEQ ID NO. 77, or SEQ ID NO. 79 and a light chain variable region comprising the amino acid sequence denoted by SEQ ID NO. 83, SEQ ID NO. 85, SEQ ID NO. 86, SEQ ID NO. 87, or SEQ ID NO. 89.

In other words, in some embodiments the isolated monoclonal antibody according to the invention is the antibody also referred to herein as "MH1", namely an antibody comprising a heavy chain variable region comprising the amino acid sequence denoted by SEQ ID NO. 73 and a light chain variable region comprising the amino acid sequence denoted by SEQ ID NO. 83.

In other embodiments the isolated monoclonal antibody according to the invention is the antibody also referred to herein as "MH36", namely an antibody comprising a heavy chain variable region comprising the amino acid sequence denoted by SEQ ID NO. 75 and a light chain variable region comprising the amino acid sequence denoted by SEQ ID NO. 85.

In further embodiments the isolated monoclonal antibody according to the invention is the antibody also referred to herein as "MH49", namely an antibody comprising a heavy chain variable region comprising the amino acid sequence denoted by SEQ ID NO. 76 and a light chain variable region comprising the amino acid sequence denoted by SEQ ID NO. 86.

In still further embodiments the isolated monoclonal antibody according to the invention is the antibody also referred to herein as "MH67", namely an antibody comprising a heavy chain variable region comprising the amino acid sequence denoted by SEQ ID NO. 77 and a light chain variable region comprising the amino acid sequence denoted by SEQ ID NO. 87.

In yet further embodiments the isolated monoclonal antibody according to the invention is the antibody also referred to herein as "MH74", namely an antibody comprising a heavy chain variable region comprising the amino acid sequence denoted by SEQ ID NO. 79 and a light chain variable region comprising the amino acid sequence denoted by SEQ ID NO. 89.

As indicated above, five antibodies, namely the antibodies referred to herein as MH2, MH73, MH75, MH76 and MH77 were shown to bind the RTB subunit.

As used herein, the term "ricin B chain" refers to the B chain of ricin (RTB), which is a galactose specific lectin. RTB is approximately 33 kDa.

In some embodiments RTB may be prepared for example by extracting the toxin from seeds of *R. communis*, and subjecting the extract to reducing conditions and to further separation steps, thereby separating the A chain from the B chain, for example as shown below.

Therefore in some embodiments the isolated monoclonal antibody according to the invention binds to ricin B chain.

In specific embodiments the isolated monoclonal antibody according to the invention comprises a heavy chain variable region comprising the amino acid sequence denoted by SEQ ID NO. 74, SEQ ID NO. 78, SEQ ID NO. 80, SEQ ID NO. 81, or SEQ ID NO. 82 and a light chain variable region denoted by SEQ ID NO. 84, SEQ ID NO. 88, SEQ ID NO. 90, SEQ ID NO. 91, or SEQ ID NO. 92.

In further embodiments the isolated monoclonal antibody according to the invention is the antibody also referred to herein as "MH2", namely an antibody comprising a heavy chain variable region comprising the amino acid sequence denoted by SEQ ID NO. 74 and a light chain variable region comprising the amino acid sequence denoted by SEQ ID NO. 84.

In further specific embodiments the isolated monoclonal antibody according to the invention is the antibody also referred to herein as "MH73", namely an antibody comprising a heavy chain variable region comprising the amino acid sequence denoted by SEQ ID NO. 78 and a light chain variable region comprising the amino acid sequence denoted by SEQ ID NO. 88.

In yet further embodiments the isolated monoclonal antibody according to the invention is the antibody also referred to herein as "MH75", namely an antibody comprising a heavy chain variable region comprising the amino acid sequence denoted by SEQ ID NO. 80 and a light chain variable region comprising the amino acid sequence denoted by SEQ ID NO. 90.

In some embodiments the isolated monoclonal antibody according to the invention is the antibody also referred to herein as "MH76", namely an antibody comprising a heavy chain variable region comprising the amino acid sequence denoted by SEQ ID NO. 81 and a light chain variable region comprising the amino acid sequence denoted by SEQ ID NO. 91.

In yet further embodiments the isolated monoclonal antibody according to the invention is the antibody also referred to herein as "MH77", namely an antibody comprising a heavy chain variable region comprising the amino acid sequence denoted by SEQ ID NO. 82 and a light chain variable region comprising the amino acid sequence denoted by SEQ ID NO. 92.

The isolated monoclonal antibody according to the invention may be a chimeric, a humanized or a human antibody.

As described in the appended Examples, chimeric macaque-human antibodies were raised against the ricin toxin, in which portions of the heavy and light chains were derived from rhesus macaque and the remainder of the chain(s) was derived from a human antibody sequence.

The term "chimeric" antibodies as herein defined refers to antibodies in which a portion of the heavy and/or light chain is derived from a particular species, while the remainder of the chain(s) is derived from another species, as well as fragments of such antibodies, which exhibit the same biological activity (namely biding to the ricin toxin). Chimeric antibodies may be prepared by any method known in the art, for example as described below.

Therefore in some embodiments the isolated monoclonal antibody according to the invention is a chimeric antibody.

It is appreciated that "humanized" forms of non-human (for example, murine) antibodies are antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

The term "human antibody" as used herein refers to an antibody that possesses an amino acid sequence corresponding to that of an antibody produced by a human and/or has been made using any of the techniques for making human antibodies disclosed herein. This definition specifically excludes a humanized antibody that comprises non-human antigen-binding residues.

Preparation of humanized and human antibodies is well known in the art.

The present invention further encompasses any antigen-binding fragments of the isolated monoclonal antibody of the invention. Such antigen-binding fragments may be for example Fab and F(ab')$_2$, which are capable of binding antigen. Such fragments may be produced by any method known in the art, for example by proteolytic cleavage, using enzymes such as papain (to produce Fab fragments) or pepsin (to produce F(ab')$_2$ fragments).

Therefore in some embodiments the isolated monoclonal antibody according to the invention is wherein said antibody is an antibody fragment selected from the group consisting of Fv, single chain Fv (scFv), heavy chain variable region, light chain variable region, Fab, F(ab)$_2$' and any combination thereof.

As exemplified below, the chimeric antibodies prepared in accordance with the present disclosure were shown to neutralize the ricin toxin using an in vitro neutralization assay in Hela Ub-FL cells. The amount of antibody required to neutralize 50% of the toxin is shown in Table 5 below.

Thus in some embodiments the isolated monoclonal antibody according to the invention is wherein said antibody is a neutralizing antibody.

The term "Neutralizing antibody" (or Nab) as herein defined refers to an antibody which defends a cell from an antigen or infectious body by inhibiting or neutralizing the biological effect of the antigen or infectious body. Neutralizing antibodies are mainly defined by their in vitro activity, which in the present case may be assessed for example by the antibody amount that is required to neutralize 50% of the ricin toxin. As used herein the term "highly neutralizing anti ricin antibody" refers to an antibody that is capable of neutralizing the toxin and protecting between about 95% and 100% of animals exposed to ricin toxin in an in vivo protection model, when the antibody is given post-exposure, for example, six hours post exposure.

In another one of its aspects the present invention provides a bispecific molecule comprising the antibody as herein defined.

By the term "bispecific molecule" as herein defined it is meant a molecule comprising a first entity being an antibody or any antigen binding fragment thereof as herein defined and a second entity. The second entity may be a second antibody or antigen binding fragment thereof that specifically binds to a different target, such as but not limited to an epitope in ricin toxin that is different from the epitope recognized by the antibodies in accordance with the invention. The second antibody or antigen binding fragment thereof may also target other toxins, any other protein of a pathogen, a host-related protein, or a host cell, as non-limiting examples. Bispecific antibodies include cross-linked or "heteroconjugate" antibodies and can be made using any convenient cross-linking or recombinant methods.

In yet another one of its aspects the present invention provides an isolated nucleic acid molecule comprising a nucleotide sequence encoding an antibody or any antigen-binding fragment thereof as herein defined.

The term "nucleic acid" or "nucleic acid molecule" as herein defined refers to polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

In still another one of its aspects the present invention provides an expression vector comprising the isolated nucleic acid molecule as herein defined.

The term "Expression vector" sometimes referred to as "expression vehicle" or "expression construct", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

The present invention further provides a host cell transfected with the isolated nucleic acid molecule or with the expression vector as herein defined.

The term "host cells" as used herein refers to cells which are susceptible to the introduction of the isolated nucleic acid molecule according to the invention or with the expression vector according to the invention. Preferably, said cells are mammalian cells, for example CHO cells or HEK 293 (which were used in the present disclosure). Transfection of the isolated nucleic acid molecule or the expression vector according to the invention to the host cell may be performed by any method known in the art.

In yet another one of its aspects the present invention provides an immunoconjugate comprising the antibody or any antigen-binding fragment thereof as herein defined and an additional anti-ricin agent.

The term "immunoconjugate" as herein defined refers to an antibody or any antigen-binding fragment thereof according to the invention that is conjugated (linked or joined) to an additional agent Immunoconjugates may be prepared by any method known to a person skilled in the art, for example, by cross-linking the additional agent to the antibody according to the invention or by recombinant DNA methods.

The term "additional anti-ricin agent" as herein defined refers to any agent known in the art for the treatment of ricin poisoning. In some embodiments the additional anti-ricin agent in accordance with the invention is a sugar analogue (that prevents ricin binding to its target), an inhibitor of the catalytic subunit of ricin toxin (for example azidothymidine) and an additional antibody.

The term "additional antibody" as herein defined refers to an antibody, which is not the antibody according to the invention, which may be used in combination with any one of the antibodies of the invention. Such antibody may be directed against ricin, against a different antigen or toxin of *Ricinus communis*, against a different pathogen or against a host-related moiety.

The present invention further provides a pharmaceutical composition comprising as an active ingredient the isolated monoclonal antibody or any antigen-binding fragment thereof as herein defined, the bispecific molecule or the immunoconjugate according to the invention and a pharmaceutically acceptable carrier, excipient or diluent.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art. Supplementary active ingredients can also be incorporated into the compositions, e.g. antibiotics.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In some embodiments the pharmaceutical composition as herein defined further comprises an adjuvant.

An "adjuvant" as herein defined refers to a pharmacological and/or immunological agent that modifies the effect of other agents. Adjuvants are inorganic or organic chemicals, macromolecules or entire cells of certain killed bacteria, which enhance the immune response to an antigen. Examples of adjuvants include, but are not limited to Freund's adjuvant, aluminium hydroxide etc.

In some further embodiments the pharmaceutical composition according to the invention further comprises an additional anti-ricin agent.

In yet another one of its aspects, the present invention provides the isolated monoclonal antibody or any antigen-binding fragment thereof according to the invention, the bispecific molecule, the immunoconjugate or the pharmaceutical composition as herein defined for use in a method of prophylaxis, treatment or amelioration of ricin toxin poisoning.

Further provided is a method of prophylaxis, treatment or amelioration of ricin toxin poisoning comprising administering to a subject in need thereof a therapeutically effective amount of the isolated monoclonal antibody or any antigen-binding fragment thereof according to the invention, the bispecific molecule, the immunoconjugate or the pharmaceutical composition as herein defined.

By the term "prophylaxis" as herein defined it is meant to provide a preventive or prophylactic treatment, namely acting in a protective manner, to defend against or prevent ricin poisoning, namely before exposure to ricin toxin.

The terms "treatment","treating","treat" or forms thereof as used herein, mean preventing, ameliorating or delaying the onset of one or more clinical indications of poisoning or disease activity resulting from exposure to ricin toxin in a subject at risk of being poisoned by or exposed to ricin toxin or in a subject that was exposed to ricin toxin.

Administration according to the present invention may be performed by any of the following routes: oral administration, intravenous, intramuscular, intraperitoneal, intratechal or subcutaneous injection; intrarectal administration; intranasal administration, ocular administration or topical administration.

In specific embodiments administration according to the present invention may be performed intravenously.

In some embodiments the method according to the invention is further comprises administering to a subject in need thereof an additional anti-ricin agent.

The term "subject in need thereof" as herein defined means warm-blooded animals, such as for example rats, mice, dogs, cats, guinea pigs, primates and humans at risk of being exposed to ricin toxin or anyone who has come in contact with ricin toxin, for example mail handlers, military personnel, laboratory workers and people who may be exposed to ricin toxin during a bio-terror event.

The method according to the invention may be applied where the isolated monoclonal antibody or any antigen-binding fragment thereof, bispecific molecule, immunoconjugate or pharmaceutical composition as herein defined is administered to the subject prior to or after exposure to ricin toxin.

In some embodiments the isolated monoclonal antibody or any antigen-binding fragment thereof, bispecific molecule, immunoconjugate or pharmaceutical composition as herein defined is administered to the subject immediately after exposure to ricin toxin or between about 1 to about 72 hours after exposure to ricin toxin.

As used herein the term "immediately" encompasses the instant time frame following detection of ricin poisoning, e.g. minutes after detection.

By way of a non-limiting example, the isolated monoclonal antibody or any antigen-binding fragment thereof, bispecific molecule, immunoconjugate or pharmaceutical composition as herein defined is administered to the subject about 1, 6, 12, 18, 24, 30, 36, 42, 48, 54, 60, 66 or about 72 hours after exposure to ricin toxin.

The term "therapeutically effective amount" for purposes herein defined is determined by such considerations as are known in the art in order to cure, arrest or at least alleviate or ameliorate the medical conditions associated with ricin poisoning. For any preparation used in the methods of the invention, the dosage or the therapeutically effective amount can be estimated initially from in vitro cell culture assays or based on animal models known in the art.

In the above and other embodiments the isolated monoclonal antibody or any antigen-binding fragment thereof is administered at a therapeutically effective amount. The treating physician would be able to determine the appropriate therapeutic dosage depending on various clinical parameters of the patient as is well known in the art. A therapeutically effective amount of the antibody is for example between about 10 μg/kg to about 50 mg/kg. Non-limiting examples of dosage forms include 1 mg/kg, 2 mg/kg, 3 mg/kg, 3.3 mg/kg, 5 mg/kg, 10 mg/kg, 20 mg/kg, 30 mg/kg, 40 mg/kg and 50 mg/kg.

It should be appreciated that the therapeutically effective amount as herein defined refers to the isolated monoclonal antibody or any antigen-binding fragment per se, as the active ingredient of a pharmaceutical composition, or as a component of a bispecific molecule or an immunoconjugate.

In some further embodiments the isolated monoclonal antibody or any antigen-binding fragment thereof, bispecific molecule, immunoconjugate or pharmaceutical composition as herein defined is administered to the subject as a single dose or as multiple doses.

As demonstrated in the appended examples, the antibodies described herein, in particular the antibodies referred to as MH75, MH1, MH77, MH73, MH2, MH76, MH49, MH36, MH67 and MH74 were shown to neutralize the ricin toxin in an in vitro assay, by measuring the translation capacity of a cell that was exposed to ricin toxin.

Specifically, using mice in vivo protection model the antibodies designated MH73, MH36, MH75, MH1 and MH77 yielded extremely high survival rates of 83%, 95%, 96%, 100% and 100%, respectively.

Thus in still another one of its aspects the present invention provides a method of neutralizing ricin poisoning comprising administering to a subject in need thereof a therapeutically effective amount of the isolated monoclonal antibody or any antigen-binding fragment thereof, the bispecific molecule, the immunoconjugate or the pharmaceutical composition as herein defined.

By the term "neutralizing" it is meant blocking, preventing or at least reducing the biological activity of ricin toxin, namely blocking, preventing or at least reducing its ability to inactivate the 28S ribosomal subunit.

The ability of the antibody to neutralize the toxicity of ricin toxin may be monitored by any method known in the art, in particular, using the neutralization assay described herein below or using a viability assay, for example by following the survival of cells that were exposed to ricin toxin and incubated in the presence of the antibody as herein defined, or using a standard animal model, for example as shown in the examples.

In certain embodiments the anti-ricin antibodies of the invention can serve as an effective post-exposure therapy for ricin intoxication at early as well as at late time-points after exposure. While each of the antibodies MH73, MH75, MH1 and MH77 is capable of providing high protection rate by itself, combinations of these highly neutralizing antibodies could also be therapeutically effective.

For example, a combination of the antibodies MH1 and MH75, or a combination of the antibodies MH1 and MH77, or a combination of the antibodies MH75 and MH77. Also contemplated are combinations of at least three of these antibodies, for example a combination of MH75, MH1 and MH77. Also contemplated are combinations of at least four of these antibodies, for example a combination of MH73, MH75, MH1 and MH77.

For example, as detailed in the Examples section below a composition comprising the antibodies MH75, MH1 and MH77 (also referred to as the "antibody cocktail therapy") was highly effective, its administration resulting in very high cure rates (>70%) when animals were treated as late as 48 hours post exposure and significant protection (>30%) even at 72 hours. The present invention thus discloses for the first time that a composition comprising several anti-ricin antibodies can serve as a highly effective antidote at such late time-points after exposure. From the clinical point of view, this extended therapeutic window is of high importance, allowing adequate time to accurately identify the causative agent and may permit initiation of life-saving treatment with these antibodies even after the onset of clinical signs.

The present invention thus provides a pharmaceutical composition comprising a combination of two or more of the antibodies of the invention and a pharmaceutically acceptable carrier, excipient or diluent, wherein the antibodies of the invention are the antibodies referred to as MH75, MH1, MH77, MH73, MH2, MH76, MH49, MH36, MH67 and MH74. In particular, the antibodies referred to as MH73, MH75, MH1 and MH77. In certain embodiments the pharmaceutical composition comprises a combination of two, three or four antibodies. In particular, a combination of two, three or four of the antibodies referred to as MH73, MH75, MH1 and MH77.

In one embodiment, the present invention provides a pharmaceutical composition comprising a combination of at least two anti-ricin antibodies, wherein said the antibodies are selected from the group consisting of antibodies MH75, MH1 and MH77, and a pharmaceutically acceptable carrier, excipient or diluent.

In a preferred embodiment, the present invention provides a pharmaceutical composition comprising the antibodies MH75, MH1 and MH77 and a pharmaceutically acceptable carrier, excipient or diluent. In another embodiment the present invention provides a pharmaceutical composition consisting of the antibodies MH75, MH1 and MH77, and a pharmaceutically acceptable carrier, excipient or diluent.

By way of a non-limiting example, the pharmaceutical composition comprising the combination of antibodies as herein defined is administered to the subject about 1, 6, 12, 18, 24, 30, 36, 42, 48, 54, 60, 66, 72 or about 96 hours after exposure to ricin toxin.

The pharmaceutical composition comprising the combination of antibodies as herein defined is administered to the subject at a therapeutically effective amount. The treating physician would be able to determine the appropriate therapeutic dosage depending on various clinical parameters of the patient as is well known in the art. A therapeutically effective amount of the antibody is for example between about 10 μg/kg to about 50 mg/kg. Non-limiting examples of dosage forms include 1 mg/kg, 2 mg/kg, 3 mg/kg, 3.3 mg/kg, 5 mg/kg, 10 mg/kg, 20 mg/kg, 30 mg/kg, 40 mg/kg and 50 mg/kg.

As shown in the Examples below an amount of 300 μg per mouse of the antibody combination comprising MH1, MH75 and MH77 was effective in ameliorating ricin intoxication in mouse models. This amount is equal to a dose of 10 mg/kg. The corresponding effective dose in humans may even be slightly lower, e.g. 1-10 mg/kg.

The present invention further provides a method of detecting ricin toxin in a biological sample obtained from a subject, said method comprising:
  (a) contacting said biological sample with the isolated monoclonal antibody or any antigen-binding fragment thereof according to the invention, wherein said monoclonal antibody is labeled with a detectable marker; and (b) detecting said isolated monoclonal antibody or any antigen-binding fragment thereof;

wherein the presence of said isolated monoclonal antibody or any antigen-binding fragment thereof indicates the presence of ricin toxin in said biological sample.

Detecting the isolated monoclonal antibody may be performed by any method known to a person skilled in the art based on the detectable marker present on the antibody.

The term "detectable marker" refers to any atom, molecule or a portion thereof, the presence, absence or level of which is directly or indirectly monitorable. Labeling of the antibodies as herein defined may be performed by any method known in the art.

The term "biological sample" as herein defined encompasses fluids, solids and tissues obtained from the subject. The term biological sample also refers to forensic samples.

In another one of its aspects the present invention provides a kit for detecting ricin toxin comprising:

(a) at least one labeled isolated monoclonal antibody or any antigen-binding fragment thereof according to the invention;

(b) means for detection of said labeled isolated monoclonal antibody; and optionally (c) instructions for use of said kit.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody. As used herein, the term "purified" or "to purify" also refers to the removal of contaminants from a sample.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures
Immunization

Crude ricin was prepared from seeds of endemic *Ricinus communis* (*R. communis*) that were homogenized in a Waring blender in 5% acetic acid/phosphate buffer ($Na_2HPO_4$, pH 7.4). The homogenate was centrifuged and the clarified supernatant containing the toxin was subjected to ammonium sulphate precipitation (60% saturation). The precipitate was dissolved in PBS and dialyzed extensively against the same buffer. The crude ricin preparation was loaded onto a gel-filtration column (Superdex 200HR 16/60 Hiload) and washed out with PBS to yield two well-separated protein peaks corresponding to RCA (*Ricinus communis* agglutinin, another toxic protein found in the castor bean) and ricin. Ricin was further reduced in the presence of DTT in pH 9.0 followed by the addition of Iodoacetamide (IAA, added in order to block cysteines and prevent disulfide bond formation) and dialysis in PBS.

Two rhesus macaques (*Macaca Mulata*) were used for eliciting antibodies against ricin. The first rhesus macaque was injected with 100 μg of reduced ricin, prepared as described above, mixed with complete Freund's adjuvant followed by two monthly booster injections of 100 μg reduced ricin mixed with incomplete Freund's adjuvant. The second rhesus macaque was injected with 2 μg of purified ricin mixed with complete Freund's adjuvant followed by three monthly booster injections of 5, 80 and 80 μg purified ricin mixed with incomplete Freud adjuvant. Seven days after the last boost, the monkeys were sacrificed and samples were taken from their blood and lymphatic nodes in order to isolate mRNA that was subsequently used for variable heavy and variable light (VH/VL) chain amplification.

Phage Library Construction mRNA was extracted from lymph nodes and peripheral blood of the immunized Macaques, and was reverse-transcribed into cDNA. The heavy and light chains variable regions (VH and VL, respectively) were amplified from the cDNA, using a set of primers designed to cover all known antibody families of Monkeys. The nucleic acid sequences of these primers (synthesized by Integrated DNA Technologies, IDT) are detailed in Table 1 below (SEQ ID NO. 1 to SEQ ID NO. 52). VH and VL were randomly assembled by PCR to construct a combinatorial single-chain (scFv) library, which was then cloned into phagmid vector to create a phage-display library.

TABLE 1

Primers designed for the amplification of antibodies variable regions

| SEQ ID NO. | Primer | Sequence |
| --- | --- | --- |
| 1 | Lib-H1 F | CAGGAGCAGCTGGTGCAGTC |
| 2 | Lib-H2 F | CAGGTCCAGCTGGTGSAGWC |
| 3 | Lib-H3 F | CAGGTSCAGCTCGAGSAGTC |
| 4 | Lib-H4 F | CAGGTGCAGCTGCAGGAGTC |
| 5 | Lib-H5 F | CAGCTGCAGCTGCAGSAGTC |
| 6 | Lib-H6 F | CAGGTGCAGCTRCTCGAGTS |
| 7 | Lib-H7 F | CAGGTSCAGCTGGTGCAGTY |
| 8 | Lib-H8 F | CAGGTSACCTTGAAGGAGTC |
| 9 | Lib-H9 F | CAGGTCCAGCTGCAGGAAAG |
| 10 | Lib-H10 F | GAGGTGCAGYTGGTGGAGWC |
| 11 | Lib-H11 F | GAGGTTCAGYTGGTKGAATC |
| 12 | Lib-H12 F | GAGGTGCAGCTGGTGSARTC |
| 13 | Lib-H13 F | GAGGTGCAGCTGGYRGAGTC |
| 14 | Lib-H14 F | GAAGTGCAGYTGGTGGAGTC |
| 15 | Lib-H15 F | GAGGTGCAGCTCGAGGAGTC |
| 16 | Lib-H16 F | GAGGTGCAGCTGCTCGAGTC |
| 17 | VH Rev1 | CTGARGAGRCTGTGACC |

TABLE 1-continued

Primers designed for the amplification of antibodies variable regions

| SEQ ID NO. | Primer | Sequence |
|---|---|---|
| 18 | VH Rev2 | CTGAGGACACGGCAACC |
| 19 | Lib-K1 F | GATATTGTGATGAYCCAGAC |
| 20 | Lib-K2 F | GATACTGTGATGACCCAGAC |
| 21 | Lib-K3 F | GATATYGAGCTCACBCAGTC |
| 22 | Lib-K4 F | GATGTTGYRATGACTCAGTC |
| 23 | Lib-K5 F | GACATTCAGMTGWCCCAGTC |
| 24 | Lib-K6 F | GACGTTCAGATGACCCAGTC |
| 25 | Lib-K7 F | GACATCCAGATGACCCAGTC |
| 26 | Lib-K8 F | GAGCTCCWGATGACMCAGTC |
| 27 | Lib-K9 F | GAAATWGTRATGACGCAGTC |
| 28 | Lib-K10 F | GAAATCGAGCTCACRCAGTC |
| 29 | Lib-K11 F | CAAGTTATATTGACTCAGTC |
| 30 | Lib-K12 F | GACATCGAGCTCACCCAGTC |
| 31 | Lib-K13 F | GAGCTCGTGTTGACACAGTC |
| 32 | Lib-K1 Rev | YTTGAKATCCAGTTTGGTCCCGGG |
| 33 | Lib-K2 Rev | TTTGAYCTCCACCYTGGTCCCTCC |
| 34 | Lib-K3 Rev | TTTGATSTCCACTTTGGTCCCCTG |
| 35 | Lib-K4 Rev | TYTGATTTCCACCYTGGTCCCTTG |
| 36 | Lib-K5 Rev | CTTGATGTCCACCTTGGTCCCGTG |
| 37 | Lib-K6 Rev | TTTTAGTACCACCTTGGTCCCTTG |
| 38 | Lib-L1 F | CAGCCAGKGCTGACTCAGCC |
| 39 | Lib-L2 F | CAGCCTGKGCTGACTCAGYC |
| 40 | Lib-L3 F | CAGTCTGTGYTGACKCAGCC |
| 41 | Lib-L4 F | CAGTCTGCCCTGACTCAGCC |
| 42 | Lib-L5 F | CAGTCTGCCCCGAYTCAGYC |
| 43 | Lib-L6 F | CAGGCTGCCCYGACTCAGYC |
| 44 | Lib-L7 F | CAGGCAGGGCTGACTCAGCC |
| 45 | Lib-L8 F | CAGACTGTGGTGACCCAGGA |
| 46 | Lib-L9 F | AAGCCTATGCTGACTCAGCC |
| 47 | Lib-L10 F | TCTTCTGRGCTGACTCAGGA |
| 48 | Lib-L11 F | TCCTATGAGCTGACWCAGCC |
| 49 | Lib-L12 F | CAGSCTGTGCTGACTCAGCC |
| 50 | Lib-L13 F | CWGCCTGTGCTGACTCARYC |
| 51 | Lib-L1 Rev | TAGRACGGTSAGCCGGGTC |
| 52 | Lib-L2 Rev | GAGGAYGGTCAAYTTGGTG |

Phage Particle Amplification

The *E. coli* TG1 strain (Lucigen #60502) was infected with the desired phages, in the presence of a helper phage, M13KO7 (NEB #N0315S). The infected culture was centrifuged and the pellet was eluted with 2YT medium containing Ampicilin (100 μg/ml) and Kanamicin (50 μg/ml), and incubated over-night (o.n.) in 30° C. Following a further centrifugation step, the supernatant was passed over 0.45 μm filter and the phage particles were incubated in the presence of 2.5M NaCl, 20% PEG 6000 for 2 hours on ice. After an additional centrifugation step of 1 hr at 9000 g, the pellet containing the phage particles was eluted with PBS and stored at 4° C.

Panning

The process of selecting antibodies against a specific antigen from a phage display library is called "panning". In one cycle of panning, the library is incubated with the antigen, to allow binding. The unbound phages are then eliminated by washing, while those phages displaying scFv that is bound to the antigen are eluted and enriched. The eluted and enriched phages obtained in the first panning cycle may be subjected to additional panning cycles for screening of specific clones. Several consecutive panning cycles usually allow the selection of high affinity antibodies.

Biotinylated ricin, namely pure ricin that was biotinylated using a commercial kit (EZ-Link sulfo-NHS-biotin, pierce) was first incubated with Streptavidin (SA) beads (Dynabeads M-280, Invitrogen #11206D) for 30 minutes (min). The phage display library was added to the beads and the mixture was incubated for an additional 90 min The beads were then washed with 3% bovine serum albumin (BSA) in phosphate buffered saline (PBS), followed by washing with phosphate buffered saline Tween-20 (PBST) and PBS. The bound phages were eluted from the beads by incubation in 100 mM Triethylamine for 30 min, followed by neutralization with 200 μl Tris-HCl pH 7.5 (1M). The resulting phages were used to infect TG1 cells and grown over night for phage enrichment. The culture was then collected and 100 μl were used for phage rescue, to prepare the input for the next round of panning. In total, three rounds of selection were used for isolating the anti-ricin antibodies.

Screening

Individual clones were obtained by performing three rounds of selection (three panning cycles) as described above and grown in 96-well plates. Each clone was then tested for its ability to specifically bind ricin, and each of its subunits, namely ricin chain A and ricin chain B in an ELISA assay as described below. Maxisorp 96-well microtiter plates were coated overnight with 5 μg/ml of ricin (50 μl/well) in NaHCO$_3$ buffer (50 mM, pH 9.6), then washed and blocked with PBST buffer (0.05% Tween 20, 2% BSA in PBS) at room temperature for one hour. Clone samples were added to the ricin-coated plates for an incubation of one hour, the plates were then washed with PBST, incubated with the detecting horseradish peroxidase (HRP)-conjugated anti-M13 antibody and then developed using Tetramethylbenzidine (TMB/E). Single-stranded DNA of phage clones was prepared using Big Dye (Applied Biosystems) and the PCR products were analyzed with ABI PRISM 310 Genetic Analyzer (Applied Biosystems).

Producing Full Length Antibodies

Each single chain variable fragment (scFv) isolated from the phage display library was cloned into a mammalian full-length Immunoglobulin expression vector, providing each chain with the corresponding signal-peptide and constant gene, and resulting in IgG1/κ/λ chimeric macaque-human antibody expression.

Antibody Sequencing

The plasmids encoding the chimeric antibodies were sequenced using ABI PRISM 310 Genetic Analyzer (Applied Biosystems). The plasmids were transiently transfected to HEK293 cells, and antibodies were purified from the culture media using Protein A columns.

In vitro Neutralization Assay

Hela Ub-FL cells (7) were cultured in Dulbecco's modified Eagle's medium (DMEM, Biological Industrial, Beit Haemek, Israel) supplemented with 10% fetal calf serum (FCS). For cytotoxicity studies (i.e. the neutralization assays), cells were seeded in 96-well plates ($1 \times 10^5$ cells/well) in medium containing ricin (at 2 ng/ml, prepared as described above) and incubated at 37° C. in the presence or absence of the anti-ricin antibodies prepared as discussed above. Sixteen hours later the medium was removed, and the cells were subjected to a protein translation assay, in order to determine the neutralizing effect of the antibody. Briefly, the cells were lysed and the residual intracellular ubiquitin-luciferase fusion protein activity was determined using D-luciferin as a substrate (measured in luminometer; Victor3, PerkinElmer) and expressed as percent activity determined for untreated cells.

In vivo Protection Assay

Female out bred ICR mice (Charles River Laboratories) were maintained at 20-22° C. and a relative humidity of 50±10% on a 12-h light/dark cycle, fed with commercial rodent chow (Koffolk Inc.) and provided with tap water ad libitum. Treatment of animals was in accordance with regulations outlined in the USDA Animal Welfare Act and the conditions specified in Guide for Care and Use of Laboratory Animals (National Institute of Health, 1996). Animal studies were approved by the local ethical committee on animal experiments.

Mice, 27-32 gr, were intranasaly intoxicated with $2LD_{50}$ of ricin (5 μg/Kg, 50 μl/mice) and six hours later were treated with 100 μg of anti-ricin antibody which was injected intravenously. The mice were monitored for 14 days and the protection conferred by each antibody was calculated as percent of surviving mice. Mice intoxicated with ricin without antibody treatment, were used as control.

Example 1

Preparation of Chimeric Antibodies Directed to Ricin

Rhesus macaques were immunized against ricin and mRNA was extracted from the immunized macaques and reverse-transcribed into cDNA, as described above. The cDNA was further used for construction of a phage-display library and individual phage clones were selected as described above.

After panning and screening of the phage display library, 10 different antibodies, termed MH1, MH2, MH36, MH49, MH67, MH73, MH74, MH75, MH76 and MH77, were isolated and sequenced, as described above. The nucleic acid sequences of the heavy and the light chains of the antibodies are shown in Table 2 below. A sequence alignment of the nucleic acid sequences of the above isolated antibodies is shown in FIG. 1 for the heavy chain sequences and in FIG. 2 for the light chain sequences of the above antibodies.

TABLE 2

Nucleic acid sequences of the antibodies heavy and light chains

| SEQ ID NO. | Sequence | Description |
|---|---|---|
| 53 | GAGGCGCAGCTCGAGGAGTCGGGCCCAGGACTGGTGAAGCCTTCGGAGACC CTGTCCCTCAGTTGCGCTGTCTCTGGTGGCTCCTTCAGGAGTTACTGGTGG GGCTGGATCCGCCAGCCCCAGGGAAGGGCCTGGAGTGGATTGGGAGTATC TATGGCAGTAGTGGGAGCACCGAATACAACCCCTCCCTCAAAAGTCGAGCC ACCATTTCAAGAGACACGTCCAAGAACCAGTTCTCCCTGAAGCTGAGCTCT GTGACCGCCGCGGACACGGCCGTCTATTACTGTGCGAGGCAGATACAATTT TTGACTGATGCTTTTGATTTCTGGGGCCAAGGGCTCAGGGTCACAGTCTCC TCA | Heavy chain of MH49 |
| 54 | CAGGTGCAGCTCGAGCAGTCGGGCCCAGGACTGGTGAAGCCTTCGGAGACC CTGTCCCTCAGTTGCGCTGTCTCTGGTGGCTCCTTCAGGAGTTACTGGTGG GGCTGGATCCGCCAGCCCCAGGGAAGGGCCTGGAGTGGATTGGGAGTATC TATGGCAGTAGTGGGAGCACCGAATACAACCCCTCCCTCAAAAGTCGAGCC ACCATTTCAAGAGACACGTCCAAGAACCAGTTCTCCCTGAAGCTGAGCTCT GTGACCGCCGCGGACACGGCCGTCTATTACTGTGCGAGGCAGATACAATTT TTGACTGATGCTTTTGATTTCTGGGGCCAAGGGCTCAGGGTCACAGCCTCC TCA | Heavy chain of MH67 |
| 55 | CAGGTGCAGCTGCAGGAGTCGGGCCCAGGACTGGTGAAGCCTTCGGAGACC CTGTCCCTCACCTGCGCTGTCTCTGGTGGCTCCCTCAGCAGTAACTACTGG AGCTGGATCCGCCAGGCCCCAGGGAAGGGACTGGAGTGGATTGGACATATC TTTGGTGGTGGTGGGGGCACCGACTACAACCCCTCCCTCAAGAGTCGAGTC ACCATTTCAACAGACACGTCCAAGAACCAGTTCTCCCTGAAGCTGAGCTCT CTGGCCGCCGCGGACACGGCCGTGTATTACTGTGCGAGAGCTGCAATAATG TACCCCAACCGGTTCGATGTCTGGGGCCCGGGAGTCCTGGTCACAGCCTCT AGC | Heavy chain of MH73 |
| 56 | GAGGTGCAGCTGGTGCAATCTGGAGCAGAGGTGAAAAGGCCCGGGGAGTCA CTGAAGATCTCCTGTAAGACTTCTGGATACAGCTTTACCAGCTACTGGATC AGCTGGGTGCGCCAGATGCCCGGGAAAGGCCTGGAGTGGATGGGGGCGATT GATCCTACTGATTCTGATACCAGATACAACCCGTCCTTCCAAGGCCAGGTC ACCATCTCCGCCGACAAGTCCATCAGCACCGCCTACCTGCAGTGGAGCAGG CTGAAGGCCTCGGACACCGCCACGTATTACTGTGCGAAATCAGACTGGAGT GATTATTATGGCAACTCATTGGATGTCTGGGGCCGGGGAGTTCTGGTCACA GCCTCTTCA | Heavy chain of MH74 |

TABLE 2-continued

Nucleic acid sequences of the
antibodies heavy and light chains

| SEQ ID NO. | Sequence | Description |
| --- | --- | --- |
| 57 | CAGGAGCAGCTGGTGCAGTCTGGGGGCGGCTTGGCAAAGCCTGGGGGGTCC CTGAGACTCTCCTGCGCAGACTCCGGATTCACCTTCAGTGACCACTACATG GACTGGGTCCGCCAGGCTCCAGGGAAGGGGCTGGAGTGGGTCTCACGTATT AGTACTGGTGGTGGAACCACATGGTACGCAGACTCCGTGAAGGGCAGATTC ACCATCTCCAGAGAGAACGCCAACAACACACTGTATCTTCAAATGAACAGC CTGAGAGGTGAGGACACGGCTGTCTATTACTGTGCGAAAGTTCCCACGGGA TACAGTCAAGGGGTCTGGGGGCCGGGAGTCCTGGTCACAGCCTCCTCA | Heavy chain of MH75 |
| 58 | CAGGTGCAGCTGCAGGAGTCTGGGGGCGGCTTGGCAAAGCCTGGGGGGTCC CTGAGACTCTCCTGCGCAGCCTCCGGATTCACCTTCAGTGACTACTACATG GACTGGGTCCGCCAGGCTCCAGGGAAGGGGCTGGATTGGGTCTCACGCATT AGTAATGGTGGTGGTACCACATGGTACGCAGACTCCGTGAAGGGCAGATTC ACCATCTCCAGAGAGAACGCCAAGAACACACTGTATCTTCAAATGAACAGC CTGAGACCTGAGGACACGGCTGTCTATTACTGTGCGACGGTGCCCACAGCG ACATCTGGAATAGGCAACTGGGGCCAGGGAGTCCTGGTCACAGCCTCCTCA | Heavy chain of MH76 |
| 59 | CAGGTGCAGCTGCTCGAGTCGGGCCCAGGACTGGTGAAGCCTTCAGAGACC CTGTCCCTCACCTGCACTGTCTCTGGTGGCTCTTTCAGTAGTAGTCATTGG TGGAACTGGATCCGCCAGGCCCAGGGAAAGGGCTGGAGTGGATTGGCTAT ATCACCACTAGTAATGGTGCCACCTACTACAACCCCTCCCTCAAGAGTCGA GTCACCATTTCAACAGACACGTCCAAGAACCAGTTCTCCCTGAAACTGAGC TCTGTGACCGCCGCGGACTCGGCCGTGTATTTCTGTGCGAGGGGATACAGT AACTGGGACAACTGGTTCGATGTCTGGGGCCCGGGAGTCCTGGTCACAGTC TCCTCA | Heavy chain of MH77 |
| 60 | CAGCTGCAGCTGCAGGAGTCGGGCCCAGGACTGGTGAAGCCTTCAGAGACC CTGTCCCTCACTTGCGCTGTCTCTGGTGGCTCCATCAGCGGTGGTTATGGC TGGGGCTGGATCCGCCAGCCCCCAGGGAAGGGGCTGGAGTGGGTTGGGAGT ATCTATGGTAGTACTGGGAACACCTACTACAACCCCTCCCTCAAGAGTCGA GTCACCATTTCAACAGACACGTCCAAGAACCAGCTCTCCCTGAAGGTGAGC TCTGTGACCGCCGCGGACACGGCCATCTACTACTGTGCGAGAGCCCGCAGT GGTACTTTGTGGTTCCTCGAGTTCTGGGGCCAGGGCGCCCCGGTCACAGCA TCCTCA | Heavy chain of MH1 |
| 61 | GAGGTTCAGTTGGTGGAATCTGGGGGCGGCTTGGCAAAGCCTGGGGGGTCC CTGAGACTCTCCTGCGCAGCCTCCGGATTCACCTTCAGTGACTACTACATG GACTGGGTCCGCCAGGCTCCAGGGAAGGGGCTGGAGTGGGTCTCACGTATT AGTAATGGTGGTGGTAGTAAATGGTACGCAGACTCCGTGAAGGGCAGATTC ACCATCTCCAGAGAGAACGCCAAGAACACACTGTATCTTCAAATGAACAGC CTGAGAGCTGAGGACACGGCTGTATATTACTGTGCGGAAGTTCCCACGGGA TACAGTCAAGGTGTCTGGGGCCCGGGAGTCCTGTTCACAGTCTCCTCA | Heavy chain of MH2 |
| 62 | GAAGTGCAGCTGGTGGAGTCTGGGGGAGGCTTGGTCCAGCCTGGGGGGTCC CTGAGGCTCTCCTGTGCAGCCTCTGGATTCACCTTCAGTAACGTCTGGATG AACTGGGTCCGCCAGACTCCAGGGAAGGGGCTAGAGTGGGTTGCCCGTATT AAAGTCAAAGCTGACGGTGGAACAGCAGATTACGCCGCGTCTGTGAAAGGC AGATTCACCATCTCAAGAGACGATTCAAAGAACACACTGTATCTGCAAATG AACAGTCTGAAAACCGAGGACACGGCCGTGTATTACTGCACCACAGAGGAG ATTACAGTGGCCCGTTATGACTACTGGGGCCAGGGAGTCCTGGTCACAGTC TCCTCA | Heavy chain of MH36 |
| 63 | CAGCCTGTGCTGACTCAGCCACGCTCAGTGTCCGTGTCCCCAGGACAGACG GCCAGGATCACCTGTGGGGGAGACAACATTGGAAGTAAAAGTGTGCAGTGG TACCAGCAGAAGCCACCGCAGGCCCCTGTGCTGGTCATCTATGCTGATAGC GAACGGCCCTCAGGAATCCCTGAGCGATTCTCTGGCTCCAACTCAGGGAAC ACCGCCACCCTGACCGTCAGCGGGGTCGAGGCCGGGGATGAGGCTGACTAT TACTGTCAGGTGTGGGACAGTAGTAGTGATCATGTGTTATTCGGAGGAGGG ACCCGGCTGACCGTCCTA | Light chain of MH1 |
| 64 | CAGTCTGTGTTGACTCAGCCACAATCGGTGTCGGTGTCCCCAGGACAGACG GCCAGGATCTCCTGTGGGGGAGACAACATTGGAAGTAAAAATGTGCACTGG TACCAGCAGAAGCCACCGCAGGCCCCTGTGCTGGTCATCTATGCTGGAACC GAACGGCCCTCAGGGATCCCTGAGCGATTCTCTGGCTCCAACTCCGGGAAC ACGGCCACCCTGACCATCAGCGGGGTCGAGGCCGGGGATGAGGCGGACTAT TACTGTCAGGTGTGGACGGTACCCGTGAGCATGTATTATTCGGAGGAGGG ACCCGGCTCACCGTCCTA | Light chain of MH2 |

TABLE 2-continued

Nucleic acid sequences of the
antibodies heavy and light chains

| SEQ ID NO. | Sequence | Description |
|---|---|---|
| 65 | CAGTCTGTGTTGACTCAGCCACCCTCAGCGTCTGGGGCTCCCGGGCAGAGT GTCACCATCTCTTGCTCTGGAAGCAGCTCCAACATCAGAGGTAATGGTGTA CACTGGTACCAGCAGCTCTCAGGAATGGCCCCCAAACTCCTCATCTATAAT AATAATCAGCGACCCTCAGGGGTCCCTGACCGATTCTCTGGCTCCAAGTCT GGCACGTCAGCCTCCCTGGCCATCACTGGTCTCCAGTCTGAGGATGAGGCC GATTATTACTGCGAGGCATGGGATAACAGCCTGAGCGGTGGCTTATTCGGA GGAGGGACCCGGCTGACCGTCCTA | Light chain of MH36 |
| 66 | CAGCCAGGGCTGACTCAGCCTCCCTCAGCGTCTGGGGCTCCCGGGCAGAGT GTCACCATCTCTTGCTCTGGAAGCAGCTCTGACATTGGAAGTCATGACGTC TACTGGTACCAGCAGCTCCCAGGGACGGCCCCCAAGCTCCTCATCTACTAC AGTAATCAGCGACCCTCAGGGGTCCCTGACCGAATCTCTGGCTCCAAGTCT GGCACGTCAGCCTCCCTGACCATCAGCGGTCTCCGGTCCGAGGATGAGGCT GATTATTACTGTGAAACATGGGAAAACAGCCTGAGCGGTCCGGTCTTCGGC GGAGGGACCCGGCTCACCGTCCTA | Light chain of MH49 |
| 67 | GACATTCAGCTGACCCAGTCTCCATCCTCCGTGTCTGCTTCTGTGGGAGAC AGAGTCACCATCACTTGTCGGGCGAGTCAGGCCATCAGTACTTATTTAGCC TGGTATCTACAGAGGCCGGGGAAAGCCCCTGAACTCCTGATCTATTATGCA ACCACTTTACACACTGGGGTCGCTTCAGGTCTCACTGGCAGTGGATCTGGG ACGGATTTCACTCTCACCCTCAGTGCCCTGCAACCTGTAGATGTTGGAACT TACTACTGTCAACAGTTTAAAACTTTACCGTACACTTTTGGCCAGGGGACC AAAGTGGACATCAAA | Light chain of MH67 |
| 68 | GAGCTCCTGATGACACAGTCTCCATCCTCCCTGTCTGCATCTGTAGGAGAC AGAGTCACCATCTCTTGCCGGGCAAGTCAGAACATTTATAGTAATTTAGCG TGGTATCAGCAGAAACAGGGAAAACTCCTAAGCTCCTGATCTATGCTGCA TCCATCTTGCAGAGTGGGATTCCCTCTCGGTTCAGCGGCAGCGGATCTGGG ACAGATTACACTCTCACCATCACCAACCTGCAGCCTGAAGATTTTGGAACT TATTACTGTCAGCAAGGTTTTGGTATCCCCTACACTTTTGGCCAGGGGACC AAAGTGGAGTTCAAA | Light chain of MH73 |
| 69 | CAGTCTGTGTTGACTCAGCCGCCCTCAGTGTCTGGGGCGCCAGGACAGAGG GTCACCATCTCCTGCACTGGGAGTAATTCCAACATCGGGGCGGGTTATTAT GTGCAGTGGTACCAGCAGCTTCCAGGAACGGCCCCCAAACTCCTCATCTAT GAAAATAATAAGCGACCCTCAGGGGTTTCTGATCGATTCTCTGGCTCCAAG TCTGGTACCTCAGCCTCCCTGACCATCACTGGACTTCAGTCTGAGGATGAG GCTGACTATTACTGCCAGTCCTATGACAGCAGCCTGAGTGTTGTGTTATTC GGAGGAGGGACCCGGCTCACCGTCCTA | Light chain of MH74 |
| 70 | CAGTCTGTGTTGACTCAGCCACAATCGGTGTCGGTGTCCCCAGGACAGACG GCCAGGATCACCTGTGGGGGAGACAACATTGGAAGTAAAAATGTGCACTGG TACCAGCAGAAGCCACCGCAGGCCCCTGTGCTGGTCATCTATGCTGAAACC GAGCGGCCCTCAGGGATCCCTGAGCGATTCTCTGGCTCCAACTCCGGGAAC ACGGCCACCCTGACCATCAGCGGAGTCGAGGCCGGGGATGAGGCGGACTAT TACTGTCAGGTGTGGGACGGTAGCAGTGCACATGTATTATTCGCAGGAGGG ACCCGGCTGACCGTCCTA | Light chain of MH75 |
| 71 | CAGCCAGGGCTGACTCAGCCACACTCGGTGTCGGTGTCCCAGGACAGACG GCCAGGATCACCTGTGGGGGAGACAACATTGGAAGTAAAAATGTGCACTGG TACCAGCAGAAGCCACCGCAGGCCCCTGTGCTGGTCATCTATGCTGATAGC GAACGGCCCTCAGGGATCCCTGAGCGATTCTCTGGCTCCAACTCCGGGAAC ACGGCCACCCTGACCATCAGCGGGGTCGAGGCCGGGGATGAGGCTGACTAT TACTGTCAGGTGTGGGACAGTAGCAGTAATCATGTGTTATTCGGAGGAGGG ACCCGGCTCACCGTACTA | Light chain of MH76 |
| 72 | GACATTCAGATGTCCCAGTCTCCTTCCTCCCTGTCTGCATCTGTGGGAGAC AAAGTCACCATCACTTGCCAGGCAAGTCAGAGTGTTAGCAGCTGGTTAGCC TGGTATCGGCAGAAACCAGGGAAGGCCCCTAAGCCCCTGATCTATAAGGCA TCCAGTTTGGAAGGTGGGGTCCCCTCAAGGTTCAGCGGCAGTGGATCTGGG ACAGATTTCACTCTCACCATCAACAGCCTGCAGCCTGAAGATTTTGCAACT TATTACTGTCAACAGTATAACAGTGTGCCGTACAGTTTTGGCCACGGGACC AAGGTGGACATCAAG | Light chain of MH77 |

The amino acid sequences of the heavy and the light chains of the antibodies MH1, MH2, MH36, MH49, MH67, MH73, MH74, MH75, MH76 and MH77 are shown in Table 3 below. The complementarity determining regions (CDRs) are shown in underline. A sequence alignment of the amino acid sequences of the above isolated antibodies is shown in FIG. 3 for the heavy chain and in FIG. 4 for the light chain of the antibodies.

TABLE 3

Amino acid sequences of the antibodies' heavy and light chains

| SEQ ID NO. | Sequence | Description |
|---|---|---|
| 73 | QLQLQESGPGLVKPSETLSLTCAVSGGSISGGYGWGWIRQPPGKGLEWVGSIYGSTGNTYYNPSLKSRVTISTDTSKNQLSLKVSSVTAADTAIYYCARARSGTLWFLEFWGQGAPVTASS | Heavy chain of MH1 |
| 74 | EVQLVESGGGLAKPGGSLRLSCAASGFTFSDYYMDWVRQAPGKGLEWVSRISNGGGSKWYADSVKGRFTISRENAKNTLYLQMNSLRAEDTAVYYCAEVPTGYSQGVWGPGVLFTVSS | Heavy chain of MH2 |
| 75 | EVQLVESGGGLVQPGGSLRLSCAASGFTFSNVWMNWVRQTPGKGLEWVARIKVKADGGTADYAASVKGRFTISRDDSKNTLYLQMNSLKTEDTAVYYCTTEEITVARYDYWGQGVLVTVSS | Heavy chain of MH36 |
| 76 | EAQLEESGPGLVKPSETLSLSCAVSGGSFRSYWWGWIRQPPGKGLEWIGSIYGSSGSTEYNPSLKSRATISRDTSKNQFSLKLSSVTAADTAVYYCARQIQFLTDAFDFWGQGLRVTASS | Heavy chain of MH49 |
| 77 | QVQLEQSGPGLVKPSETLSLSCAVSGGSFRSYWWGWIRQPPGKGLEWIGSIYGSSGSTEYNPSLKSRATISRDTSKNQFSLKLSSVTAADTAVYYCARQIQFLTDAFDFWGQGLRVTASS | Heavy chain of MH67 |
| 78 | QVQLQESGPGLVKPSETLSLTCAVSGGSLSSNYWSWIRQAPGKGLEWIGHIFGGGGGTDYNPSLKSRVTISTDTSKNQFSLKLSSLAAADTAVYYCARAAIMYPNRFDVWGPGVLVTASS | Heavy chain of MH73 |
| 79 | EVQLVQSGAEVKRPGESLKISCKTSGYSFTSYWISWVRQMPGKGLEWMGAIDPTDSDTRYNPSFQGQVTISADKSISTAYLQWSRLKASDTATYYCAKSDWSDYYGNSLDVWGRGVLVTASS | Heavy chain of MH74 |
| 80 | QEQLVQSGGGLAKPGGSLRLSCADSGFTFSDHYMDWVRQAPGKGLEWVSRISTGGGTTWYADSVKGRFTISRENANNTLYLQMNSLRGEDTAVYYCAKVPTGYSQGVWGPGVLVTASS | Heavy chain of mH75 |
| 81 | QVQLQESGGGLAKPGGSLRLSCAASGFTFSDYYMDWVRQAPGKGLDWVSRISNGGGTTWYADSVKGRFTISRENAKNTLYLQNMSLRPEDTAVYYCATVPTATSGIGNWGQGVLVTASS | Heavy chain of MH76 |
| 82 | QVQLLESGPGLVKPSETLSLTCTVSGGSFSSSHWWNWIRQAPGKGLEWIGYITTSNGATYYNPSLKSRVTISTDTSKNQFSLKLSSVTAADSAVYFCARGYSNWDNWFDVWGPGVLVTVSS | Heavy chain of MH77 |
| 83 | QPVLTQPRSVSVSPGQTARITCGGDNIGSKSVQWYQQKPPQAPVLVIYADSERPSGIPERFSGSNSGNTATLTVSGVEAGDEADYYCQVWDSSSDHVLFGGGTRLTVLA | Light chain of MH1 |
| 84 | QSVLTQPQSVSVSPGQTARISCGGDNIGSKNVHWYQQKPPQAPVLVIYAGTERPSGIPERFSGSNSGNTATLTISGVEAGDEADYYCQVWDGTREHVLFGGGTRLTVLA | Light chain of MH2 |

TABLE 3-continued

Amino acid sequences of the antibodies' heavy and light chains

| SEQ ID NO. | Sequence | Description |
|---|---|---|
| 85 | QSVLTQPPSASGAPGQSVTISCSGSSSNIRGNGVHWYQQLSGMAPKLLIYNNNQRPSGVPDRFSGSKSGTSASLAITGLQSEDEADYYCEAWDNSLSGGLFGGGTRLTVLA | Light chain of MH36 |
| 86 | QPGLTQPPSASGAPGQSVTISCSGSSSDIGSHDVYWYQQLPGTAPKLLIYYSNQRPSGVPDRISGSKSGTSASLTISGLRSEDEADYYCETWENSLSGPVFGGGTRLTVLA | Light chain of MH49 |
| 87 | DIQLTQSPSSVSASVGDRVTITCRASQAISTYLAWYLQRPGKAPELLIYYATTLHTGVASGLTGSGSGTDFTLTLSALQPVDVGTYYCQQFKTLPYTFGQGTKVKIKA | Light chain of MH67 |
| 88 | ELLMTQSPSSLSASVGDRVTISCRASQNIYSNLAWYQQKPGKTPKLLIYAASILQSGIPSRFSGSGSGTDYTLTITNLQPEDFGTYYCQQGFGIPYTFGQGTKVEFKA | Light chain of MH73 |
| 89 | QSVLTQPPSVSGAPGQRVTISCTGSNSNIGAGYYVQWYQQLPGTAPKLLIYENNKRPSGVSDRFSGSKSGTSASLTITGLQSEDEADYYCQSYDSSLSVVLFGGGTRLTVLA | Light chain of MH74 |
| 90 | QSVLTQPQSVSVSPGQTARITCGGDNIGSKNVHWYQQKPPQAPVLVIYAETERPSGIPERFSGSNSGNTATLTISGVEAGDEADYYCQVWDGSSAHVLFAGGTRLTVLA | Light chain of MH75 |
| 91 | QPGLTQPHSVSVSPGQTARITCGGDNIGSKNVHWYQQKPPQAPVLVIYADSERPSGIPERFSGSNSGNTATLTISGVEAGDEADYYCQVWDSSSNHVLFGGGTRLTVL | Light chain of MH76 |
| 92 | DIQMSQSPSSLSASVGDKVTITCQASQSVSSWLAWYRQKPGKAPKPLIYKASSLEGGVPSRFSGSGSGTDFTLTINSLQPEDFATYYCQQYNSVPYSFGHGTKVDIKA | Light chain of MH77 |

CDRs are shown in underline.

The amino acid sequences of the complementarity determining regions (CDRs) of the heavy and the light chains of the antibodies MH1, MH2, MH36, MH49, MH67, MH73, MH74, MH75, MH76 and MH77 are presented in Table 4 below. The sequences of CDRH1, CDRH2 and CDRH3 are identical in antibodies 49 and 67. These two antibodies have the same heavy chain CDRs with a different light chain, as a result of the combinatorial arrangement of the scFv's. Therefore, the sequences denoted by SEQ ID NO. 102, 103, and 104, are identical to SEQ ID NO. 105, 106, and 107, respectively.

TABLE 4

Amino acid sequences of the antibodies heavy and light chain CDRs

| SEQ ID NO. | Sequence | Description |
|---|---|---|
| 93 | SGGYGWG | MH1 heavy chain CDRH1 |
| 94 | SIYGSTGNTYYNPSLKS | MH1 heavy chain CDRH2 |
| 95 | ARSGTLWFLEF | MH1 heavy chain CDRH3 |
| 96 | SDYYMD | MH2 heavy chain CDRH1 |
| 97 | RISNGGGSKWYADSVKG | MH2 heavy chain CDRH2 |
| 98 | VPTGYSQGV | MH2 heavy chain CDRH3 |
| 99 | SNVWMN | MH36 heavy chain CDRH1 |
| 100 | RIKVKADGGTADYAASVKG | MH36 heavy chain CDRH2 |
| 101 | EEITVARYDY | MH36 heavy chain CDRH3 |

TABLE 4-continued

Amino acid sequences of the antibodies heavy and light chain CDRs

| SEQ ID NO. | Sequence | Description |
|---|---|---|
| 102 | RSYWWG | MH49 heavy chain CDRH1 |
| 103 | SIYGSSGSTEYNPSLKS | MH49 heavy chain CDRH2 |
| 104 | QIQFLTDAFDF | MH49 heavy chain CDRH3 |
| 105 | RSYWWG | MH67 heavy chain CDRH1 |
| 106 | SIYGSSGSTEYNPSLKS | MH67 heavy chain CDRH2 |
| 107 | QIQFLTDAFDF | MH67 heavy chain CDRH3 |
| 108 | SSNYWS | MH73 heavy chain CDRH1 |
| 109 | HIFGGGGGTDYNPSLKS | MH73 heavy chain CDRH2 |
| 110 | AAIMYPNRFDV | MH73 heavy chain CDRH3 |
| 111 | TSYWIS | MH74 heavy chain CDRH1 |
| 112 | AIDPTDSDTRYNPSFQG | MH74 heavy chain CDRH2 |
| 113 | SDWSDYYGNSLDV | MH74 heavy chain CDRH3 |
| 114 | SDHYMD | MH75 heavy chain CDRH1 |
| 115 | RISTGGGTTWYADSVKG | MH75 heavy chain CDRH2 |
| 116 | VPTGYSQGV | MH75 heavy chain CDRH3 |
| 117 | SDYYMD | MH76 heavy chain CDRH1 |
| 118 | RISNGGGTTWYADSVKG | MH76 heavy chain CDRH2 |
| 119 | VPTATSGIGN | MH76 heavy chain CDRH3 |
| 120 | SSSHWWN | MH77 heavy chain CDRH1 |
| 121 | YITTSNGATYYNPSLKS | MH77 heavy chain CDRH2 |
| 122 | GYSNWDNWFDV | MH77 heavy chain CDRH3 |
| 123 | GDNIGSKSVQ | MH1 light chain CDRL1 |
| 124 | ADSERPS | MH1 light chain CDRL2 |
| 125 | QVWDSSSDHVLFGG | MH1 light chain CDRL3 |
| 126 | GDNIGSKNVH | MH2 light chain CDRL1 |
| 127 | AGTERPS | MH2 light chain CDRL2 |
| 128 | QVWDGTREHVLFGG | MH2 light chain CDRL3 |
| 129 | GSSSNIRGNGVH | MH36 light chain CDRL1 |
| 130 | NNNQRPS | MH36 light chain CDRL2 |
| 131 | EAWDNSLSGGLFGG | MH36 light chain CDRL3 |
| 132 | GSSSDIGSHDVY | MH49 light chain CDRL1 |
| 133 | YSNQRPS | MH49 light chain CDRL2 |
| 134 | ETWENSLSGPVFGG | MH49 light chain CDRL3 |
| 135 | ASQAISTYLA | MH67 light chain CDRL1 |
| 136 | YATTLHT | MH67 light chain CDRL2 |
| 137 | QQFKTLPYTFGQ | MH67 light chain CDRL3 |
| 138 | ASQNIYSNLA | MH73 light chain CDRL1 |
| 139 | AASILQS | MH73 light chain CDRL2 |
| 140 | QQGFGIPYTFGQ | MH73 light chain CDRL3 |
| 141 | GSNSNIGAGYYVQ | MH74 light chain CDRL1 |
| 142 | ENNKRPS | MH74 light chain CDRL2 |
| 143 | QSYDSSLSVVLFGG | MH74 light chain CDRL3 |
| 144 | GDNIGSKNVH | MH75 light chain CDRL1 |
| 145 | AETERPS | MH75 light chain CDRL2 |
| 146 | QVWDGSSAHVLFAG | MH75 light chain CDRL3 |
| 147 | GDNIGSKNVH | MH76 light chain CDRL1 |
| 148 | ADSERPS | MH76 light chain CDRL2 |
| 149 | QVWDSSSNHVLFGG | MH76 light chain CDRL3 |
| 150 | ASQSVSSWLA | MH77 light chain CDRL1 |
| 151 | KASSLEG | MH77 light chain CDRL2 |
| 152 | QQYNSVPYSFGH | MH77 light chain CDRL3 |

Example 2

Binding of the Chimeric Antibodies to Ricin

An Elisa assay, or Biolayer Interferometry (Octate$^{red}$; Fortebio) were used in order to assess the binding ability of the various antibodies prepared as described above to ricin and to each of its two subunits, namely the A chain (RTA) and the B chain (RTB). As demonstrated in FIG. 5A, all of the antibodies showed high affinity to ricin and were able to bind variable epitopes on the antigen.

Interestingly, five of the antibodies, namely the antibodies MH1, MH36, MH49, MH67 and MH74 bind the RTA subunit; five antibodies, namely the antibodies MH2, MH73, MH75, MH76 and MH77 bind the RTB subunit. The results concerning MH73 were inconclusive in the ELISA assay but the antibody clearly binds the RTB subunit as measured using Biolayer Interferometry as shown in FIG. 5B.

Example 3

The Chimeric Antibodies Neutralize the Ricin Toxin in vitro

The capability of each of the antibodies MH1, MH2, MH36, MH49, MH67, MH73, MH74, MH75, MH76 and MH77 to neutralize the ricin toxin was studied using an in vitro neutralization assay in Hela Ub-FL cells, as described above.

The amount of antibody required to neutralize 50% of the toxin is shown in Table 5 below for each of the assayed antibodies (ED=effective dose). As demonstrated in the Table, all of the antibodies were capable of neutralizing the toxin.

TABLE 5

Concentration of antibody required to neutralize 50% of the toxin

| Antibody | $ED_{50}$ (ng/ml) |
| --- | --- |
| MH1 | 200 |
| MH2 | 5,200 |
| MH36 | 27,000 |
| MH49 | 1,200 |
| MH67 | 52,000 |
| MH73 | 11,000 |
| MH74 | 83,000 |
| MH75 | 150 |
| MH76 | 10,500 |
| MH77 | 500 |

Remarkably, the antibodies MH75, MH1, MH77 and were highly effective in neutralizing the toxin as compared to the other antibodies. Without wishing to be bound by theory, the differences in neutralization efficiency may result from differences in the affinity of each one of the antibodies to the epitope it binds, and also from differences in the epitopes, where some may be more affective for neutralization than others.

Example 4

The capability of each of the anti-ricin antibodies to neutralize the ricin toxin was studied using an in vivo protection assay, as described above.

Several anti-ricin antibodies of the invention were tested for their ability to neutralize ricin in vivo. The antibodies MH1 and MH36 were chosen as representatives of the anti-RTA group, MH73, MH75 and MH77 for the anti-RTB group and MH2 and MH76 as representatives of antibodies showing lower affinity

TABLE 6

Post exposure treatment efficacy

| Antibody | Survival proportions (%) |
| --- | --- |
| — | 0% |
| MH1 | 100 |
| MH2 | 40 |
| MH36 | 95 |
| MH73 | 83 |
| MH75 | 96 |
| MH76 | 60 |
| MH77 | 100 |

Table 6 shows the survival proportions of mice treated with the different antibodies six hours after intranasal intoxication with $2LD_{50}$ of ricin. Upon intranasal exposure of mice to $2LD_{50}$ of ricin, untreated control animals succumb within 5-9 days (mean time to death of 6.5 days). At six hours post intoxication, mice were treated by intravenous administration of 100 μg of the tested antibody and were monitored for 14 days. It was found that treatment with MH1, MH36, MH75 or MH77 yielded extremely high survival rates of 95-100%. Treatment with antibody MH73 resulted with 83% survival while in those groups treated with MH2 or MH76, 40% and 60%, respectively, have survived.

Example 5

Extended Therapeutic Window for Post-Exposure Treatment of Ricin Intoxication Conferred by the Use of a Combination of High-Affinity Antibodies Experimental Procedures In Vitro Ricin Neutralization Assay Pure ricin was prepared as described previously (8). HeLa Ub-FL cells (7) were cultured in Dulbecco's Modified Eagle's Medium (DMEM, Biological Industries, Beit Haemek, Israel) supplemented with 10% fetal calf serum (FCS). For cytotoxicity studies (11), cells were seeded in 96-well plates ($1.5 \times 10^4$ cells/well) in medium containing ricin (30 ng/ml) and incubated at 37° C. in the presence or absence of the anti-ricin antibody. Six hours later, the medium was removed; the cells were lysed; and the residual intracellular ubiquitin-luciferase fusion protein activity was determined using D-luciferin as a substrate and expressed as percent activity determined for untreated cells.

In Vivo Protection Assay

Female outbred ICR mice (Charles River Laboratories, Canterbury, UK) were maintained at 20-22° C. and a relative humidity of 50±10% on a 12-h light/dark cycle, fed with commercial rodent chow (Koffolk Inc., Rancho Santa Fe, Calif., USA) and tap water ad libitum. Treatment of animals was in accordance with regulations outlined in the U.S. Department of Agriculture (USDA) Animal Welfare Act and the conditions specified in the Guide for Care and Use of Laboratory Animals (National Institute of Health, 2011). Animal studies were approved by the local ethical committee on animal experiments.

Anesthetized mice, 27-30 g, were intoxicated by intranasal instillation (50 μl/mice) of the indicated ricin doses ($LD_{50}$=2.55 μg/kg) that was slowly applied (25 μl/nostril) using a gel-loading tip (12, 13) and treated at the indicated time points after intoxication. For the mono-antibody treatment, each antibody was diluted in PBS to a concentration of 0.5 mg/ml and for the antibody cocktail therapy, the antibodies were diluted to a final concentration of 1, 1.5 or 2 mg/ml (for the cocktail of 2, 3 or 4 antibodies, respectively). At the indicated time points after intoxication, mice were treated with 100 μg of each antibody (alone or in a cocktail) by intravenous injection in a final volume of 200 μl. The mice were monitored for 14 days, and the protection conferred by each antibody was calculated as the percent of surviving mice. Mice intoxicated with ricin without antibody treatment were used as control. Survival plots were calculated using Prism software (Version 5.01, GraphPad Software Inc., La Jolla, Calif., USA, 2007).

Epitope Binning

Binding studies were carried out using the Octet Red system (ForteBio, Version 8.1, Menlo Park, Calif., USA, 2015) that measures biolayer interferometry (BLI), essentially as described in Noy et al (14). All steps were performed at 30° C. with shaking at 1500 rpm in a black 96-well plate containing 200 μl solution in each well. Streptavidin-coated biosensors were loaded with biotinylated antibody (5 μg/ml) for 300 sec followed by a wash. The sensors were then reacted for 300 sec with ricin (10 μg/ml), moved to buffer-containing wells for another wash step and reacted with non-labeled antibody pair (300 sec followed by another short wash). Binding and dissociation were measured as changes over time in light interference after subtraction of parallel measurements from unloaded biosensors.

Results

The treatment efficacy of a cocktail comprising the antibodies MH1, MH73, MH75 and MH77 (100 μg/mouse of each of the antibodies; total 400 μg/mouse) was first tested. 100% of the animals that were treated with the antibody cocktail had survived, while untreated mice succumbed within 7 days (FIG. 6). This treatment conferred full protection to animals that were intoxicated with ricin also at a higher dose of $3LD_{50}$ and high protection rates of 86% and 73% were achieved even when the challenge doses of ricin were increased to $4LD_{50}$ and $5LD_{50}$.

Figure 7A:
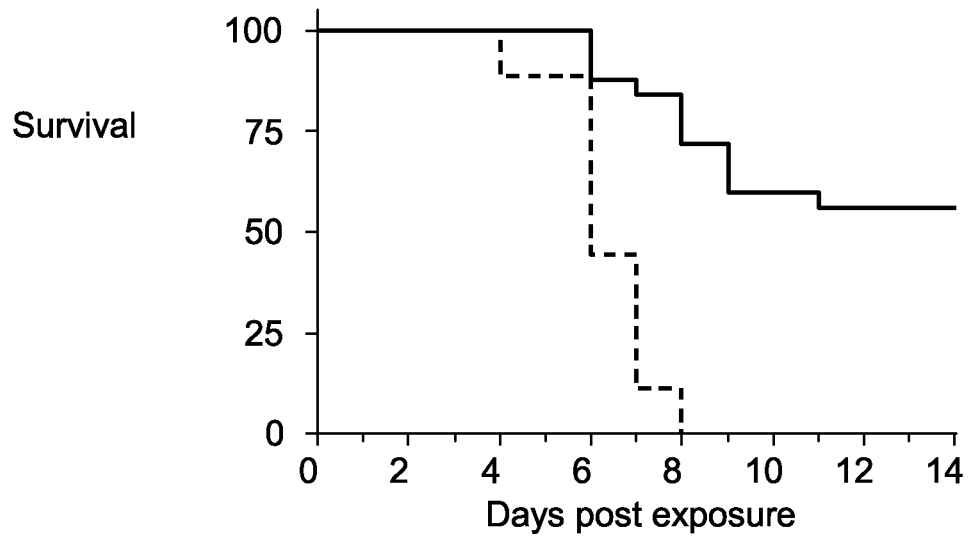
FIGS. 7A and 7B The efficacy of antibody cocktail versus mono-therapy. Ricin intoxicated mice were treated 24 hours post intoxication with either (A) the four antibodies cocktail (solid line, n=25), or (B) with either MH1 (n=32), MH73 (n=30), MH75 (n=29) or MH77 (n=28). Dashed lines represent intoxicated untreated mice (n=10). Animal survival was monitored for 14 days.
Figure 7B:
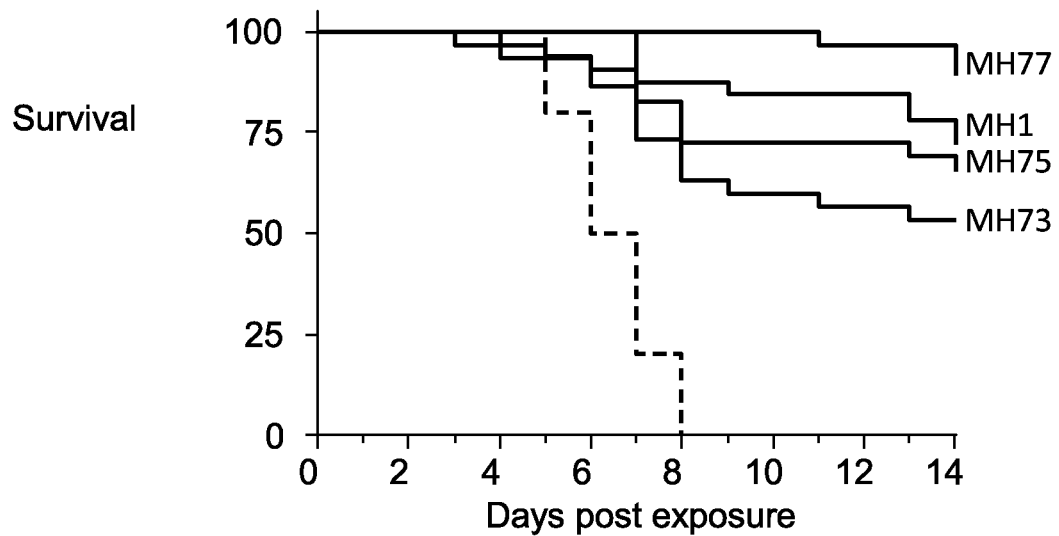

Next, in an attempt to widen the therapeutic window, the efficacy of treatment was measured at significantly later time points after ricin intoxication. To this end, mice were intoxicated with $2LD_{50}$ of ricin and treated with the antibody cocktail (MH1, MH73, MH75 and MH77; 100 μg/mouse of each of the antibodies; total 400 μg/mouse) 24 hours post intoxication. 56% of the treated animals had survived the challenge (FIG. 7A). These results are significantly higher when compared to the treatment efficacy of polyclonal anti-ricin antibodies at this time point, which results in only about 30% survival (8, 9). In order to better understand the contribution of the different antibodies in the antibody cocktail, the protection efficacy of the individual antibodies at 24 hours post exposure was compared to that of the antibody cocktail. Interestingly, it was found that when administered alone, most of the antibodies provided better protection than the cocktail of four antibodies. In fact, treatment with antibodies MH1, MH75 and MH77 resulted in survival rates of 72%, 62% and 89%, respectively (FIG. 7B). In comparison, 53% of the animals treated with antibody MH73 survived, a value that is similar to that achieved when animals were treated with the antibody cocktail (56%).

In order to explore the possibility of interference within the antibody cocktail, two approaches were taken: (1) the neutralization efficacy of each pair of the antibodies was tested in vitro and compared to the neutralization efficacy of each antibody in itself and to that of the cocktail of the four antibodies, and (2) the binding profiles of different combinations of the antibodies to the toxin, was tested.

Figure 8A:
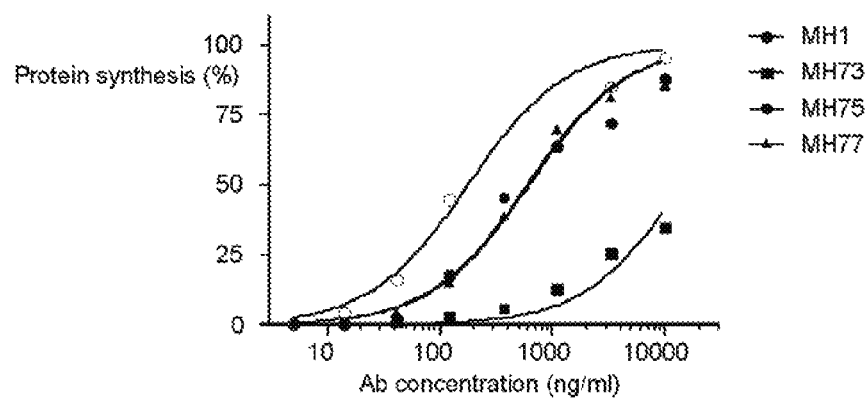
FIG. 8A and 8B In vitro neutralization of ricin. Cultured Ub-FL cells were incubated for 6 hours with ricin (30 ng/ml) and increasing concentrations of the indicated anti-ricin monoclonal antibodies (A) or of the indicated antibodies combinations (B). The residual activity of the intracellular luciferase was determined and expressed as percent activity determined for untreated cells.
Figure 8B:
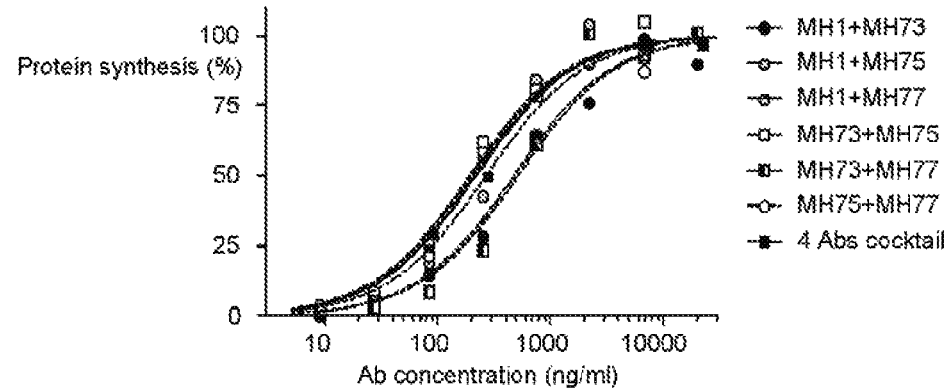

The neutralization efficacy of the antibodies was evaluated by determining their ability to inhibit the toxin activity in the HeLa Ub-FL cells based assay (FIG. 8). The presented values express the antibody concentration needed to neutralize 50% of ricin activity ($PD_{50}$). The rank order of the neutralization efficacies of the individual antibodies was found to be MH75>MH1=MH77>MH73 with $PD_{50}$ values of 180, 620, 600 and 14,200 ng/ml, respectively (Table 7). When combined, the $PD_{50}$ value of the antibody cocktail was 220 ng/ml, similar to the $PD_{50}$ value of the best-neutralizing antibody, namely MH75.

TABLE 7

$PD_{50}$ values of anti-ricin antibodies, alone, in pairs or as a cocktail.

| $1^{st}$ Antibody | $2^{nd}$ Antibody | $PD_{50}$ (ng/ml)[a] |
| --- | --- | --- |
| MH1 | — | 620 |
| MH73 | — | 14,200 |
| MH75 | — | 180 |
| MH77 | — | 600 |
| MH1 | MH73 | 520 |
| MH1 | MH75 | 200 |
| MH1 | MH77 | 270 |
| MH73 | MH75 | 190 |
| MH73 | MH77 | 480 |
| MH75 | MH77 | 210 |
| 4 Abs cocktail | | 220 |

[a]Values are calculated from the in vitro neutralization assay

Without wishing to be bound by theory, it appears that one (or more) of the four antibodies in the cocktail interferes with the activity of the other antibodies.

Figures 9A, 9B, 9C:
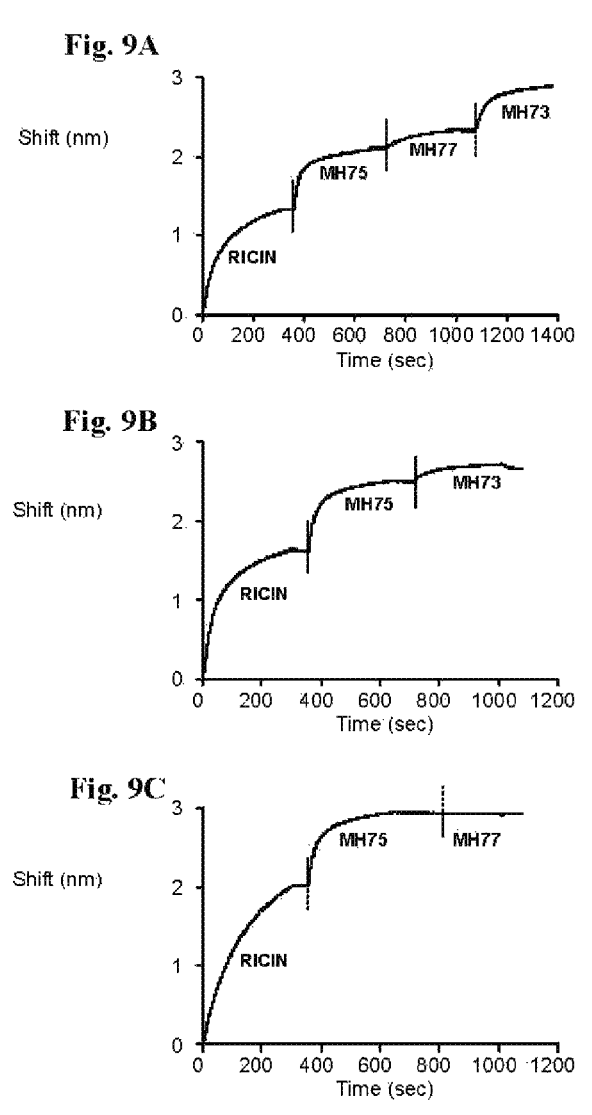

The binding profile of the antibody cocktail to ricin was studied next, using the Octet system, where protein-protein interactions can be monitored online in a label-free manner. Antibody MH1 was immobilized to the biosensor and then submerged in a ricin-containing well and the formation of the antibody-toxin complex induced a wavelength shift (FIG. 9A). Submerging of the MH1-ricin complex in MH75-containing well induced an additional wavelength shift, testifying that both antibodies bind to distinct epitopes. Likewise, the new-formed complex further interacted with antibodies MH77 and MH73, thus indicating that the four antibodies can bind simultaneously to ricin. Yet, it was noted that the wavelength shift that was induced by MH77 was much lower than expected. Therefore, MH77 was immobilized to a sensor and its interaction with the other anti-RTB antibodies was tested. In this setup, it was found that while MH75 binds well with MH77, the binding of MH73 to the pre-formed complex was impaired (FIG. 9B). It was further shown that once a complex of the antibodies MH73 (as the immobilized moiety) and MH75 was formed, antibody MH77 could not bind the toxin (FIG. 9C). It was thus concluded that there is some kind of steric hindrance when the three anti-RTB antibodies bind to ricin, and while this interference cannot be detected in vitro, in the in vivo model, under harsher conditions, it does appear to impair the antibody-cocktail activity.

Figure 10:
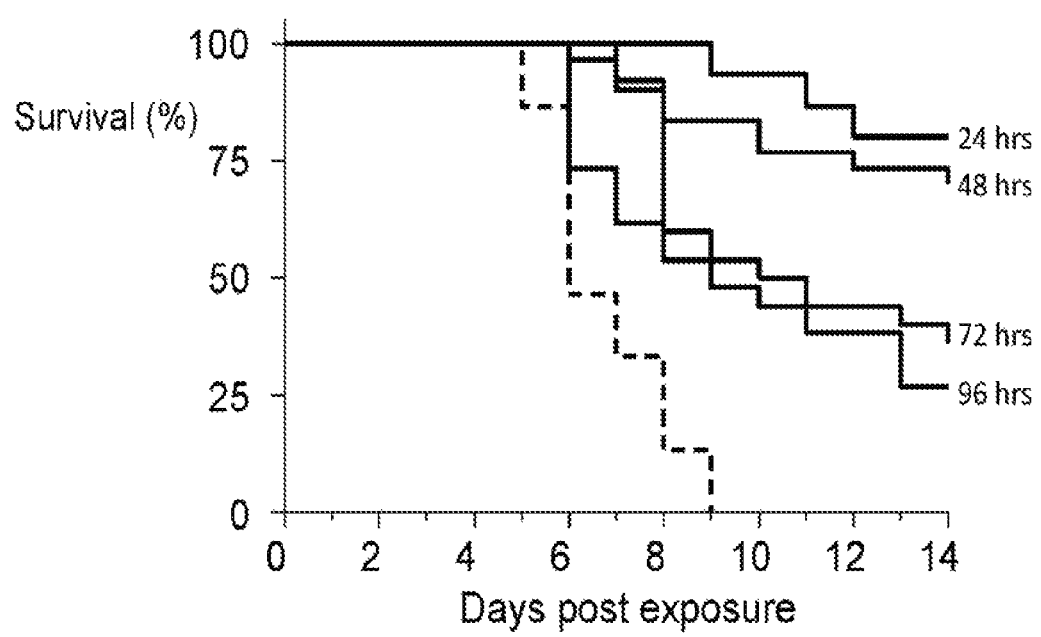
FIG. 10 Post-exposure treatment of ricin-intoxicated mice using the three antibodies-cocktail. Ricin intoxicated mice were treated with the antibody cocktail comprised of three antibodies at either 24 hours (n=15), 48 hours (n=30), 72 hours (n=25) or 96 hours (n=26) post exposure. Dashed lines: Untreated animals (n=15). Animal survival was monitored for 14 days.

The binding-profile of the antibody sets suggest that the main interference arises from the simultaneous binding of MH73 and MH77. As antibody MH73 was shown to provide the lowest protection efficacy as compared to the other three antibodies (FIG. 7B), it was decided to exclude it from the cocktail. Indeed, when tested in vivo, the three-antibodies based cocktail (MH1+MH75+MH77) was able to induce very high protection rates (80%) when given to ricin-intoxicated mice, 24 hours post exposure (FIG. 10).

Next, the possibility to initiate treatment at even later time-points (longer than 24 hours post intoxication) was evaluated. To this end, mice were intoxicated with ricin and treated with the antibody-cocktail (three antibodies: MH1+MH75+MH77; 100 g/mouse of each of the antibodies; total 300 μg/mouse) at 48-96 hours post exposure. It was found that very high cure rates were obtained (73%) when treatment was performed 48 hours post intoxication and a significant proportion (36%) of the intoxicated mice that were treated as late as 72 hours post exposure also survived (FIG. 10). Only by 96 hours post intoxication, the antibody-treatment ceased to provide a significant protection. These results are quite remarkable, especially in light of the fact that at this time point, the ricin-intoxicated mice suffer from extensive damage to the lung tissue (8, 15).

The invention claimed is:

1. A pharmaceutical composition comprising as an active ingredient a combination of at least two isolated monoclonal antibodies or any antigen-binding fragment thereof which bind to ricin toxin, and a pharmaceutically acceptable carrier, excipient or diluent, wherein said antibodies are selected from the group consisting of:
   a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125;
   b. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146; and
   c. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152.

2. The pharmaceutical composition according to claim 1, wherein said isolated monoclonal antibodies are selected from a group consisting of:
   a. a monoclonal antibody comprising a heavy chain variable region comprising the amino acid sequence denoted by SEQ ID NO. 73 and a light chain variable region comprising the amino acid sequence denoted by SEQ ID NO. 83;
   b. a monoclonal antibody comprising a heavy chain variable region comprising the amino acid sequence denoted by SEQ ID NO. 80 and a light chain variable region comprising the amino acid sequence denoted by SEQ ID NO. 90; and
   c. a monoclonal antibody comprising a heavy chain variable region comprising the amino acid sequence denoted by SEQ ID NO. 82 and a light chain variable region comprising the amino acid sequence denoted by SEQ ID NO. 92.

3. The pharmaceutical composition according to claim 1, wherein said composition comprises the isolated monoclonal antibodies:
   a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125;
   b. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146; and
   c. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152
and a pharmaceutically acceptable carrier, excipient or diluent.

4. The pharmaceutical composition according to claim 1, wherein said composition consists of the isolated monoclonal antibodies
   a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125;
   b. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146; and c. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152 and a pharmaceutically acceptable carrier, excipient or diluent.

5. The pharmaceutical composition according to claim 1, wherein said isolated monoclonal antibodies are chimeric, humanized or human antibodies.

6. The pharmaceutical composition according to claim 1, wherein said isolated monoclonal antibodies are chimeric antibodies.

7. The pharmaceutical composition according to claim 1, wherein said isolated monoclonal antibodies are antibody fragments selected from the group consisting of Fv, single chain Fv (scFv), heavy chain variable region, light chain variable region, Fab, F(ab)2' and any combination thereof.

8. The pharmaceutical composition according to claim 1, wherein said isolated monoclonal antibodies are neutralizing antibodies.

9. The pharmaceutical composition according to claim 1, wherein said composition further comprising an adjuvant.

10. The pharmaceutical composition according to claim 1, wherein said composition further comprises an additional anti-ricin agent.

11. A method of prophylaxis, treatment or amelioration of ricin toxin poisoning comprising administering to a subject in need thereof a therapeutically effective amount of the pharmaceutical composition according to claim 1.

12. The method according to claim 11, wherein said method further comprises administering to a subject in need thereof an additional anti-ricin agent.

13. The method according to claim 11, wherein said pharmaceutical composition is administered to said subject prior to or after exposure to ricin toxin.

14. The method according to claim 13, wherein said pharmaceutical composition is administered to said subject immediately after exposure to ricin toxin or between about 1 to about 96 hours after exposure to ricin toxin.

15. The method according to claim 11, wherein said isolated monoclonal antibodies in the pharmaceutical composition are administered at a therapeutically effective amount of 10-50,000 µg/kg.

16. The method according to claim 11 wherein said pharmaceutical composition is administered to said subject as a single dose or as multiple doses.

* * * * *